(12) United States Patent
Safe et al.

(10) Patent No.: US 8,389,573 B2
(45) Date of Patent: Mar. 5, 2013

(54) GLYCYRRHETINIC ACID DERIVATIVES

(75) Inventors: Stephen H. Safe, College Station, TX (US); Sudhakar Chintharlapalli, College Station, TX (US); Alan McAlees, Guelph (CA); Robert McCrindle, Cambridge (CA)

(73) Assignees: Wellington Laboratories Inc., Guelph, Ontario (CA); The Texas A&M University System, College Station, TX (US)

( * ) Notice: Subject to any disclaimer, the term of this patent is extended or adjusted under 35 U.S.C. 154(b) by 716 days.

(21) Appl. No.: 12/308,798

(22) PCT Filed: Jun. 27, 2007

(86) PCT No.: PCT/CA2007/001127
§ 371 (c)(1),
(2), (4) Date: Nov. 2, 2009

(87) PCT Pub. No.: WO2008/000070
PCT Pub. Date: Jan. 3, 2008

(65) Prior Publication Data
US 2010/0099760 A1    Apr. 22, 2010

Related U.S. Application Data

(60) Provisional application No. 60/816,590, filed on Jun. 27, 2006.

(51) Int. Cl.
*A61K 31/215* (2006.01)
*C07C 69/753* (2006.01)

(52) U.S. Cl. ...................................... 514/510; 560/116

(58) Field of Classification Search .................. 552/510; 560/116; 514/510
See application file for complete search history.

(56) References Cited

FOREIGN PATENT DOCUMENTS

| EP | 009801 | 4/1980 |
|---|---|---|
| GB | 887011 | 1/1962 |
| GB | 1024802 | 4/1966 |
| WO | WO2008/000068 | 1/2008 |

OTHER PUBLICATIONS

Pitzele "Synthesis of 2-oxygenated glycyrrhetic acid derivatives", J. Med. Chem., 17(2), p. 191-194, 1974.
Elgamal, et al., Glycyrrhetic acid derivatives with modified ring A:, J. Pharm. Sci., 62(9), p. 1557-1558, 1973.
Kim, et al., "Synthesis of new A-nor-derivatives of glycyrrhetic acid", Zhurnal Obshchei Kimii, 48(9), p. 2146-2147, 1978.
Ribo, et al., "Synthesis of 1, 11-dioxo-olean-2, 12-dien-30-oic acid methyl ester and its 24-nor derivative", Afinidad, 38 (373), p. 197-200, 1981.
STN Search Transcript, Mar. 28, 2006, 11:41 AM "Biological Study".
STN Search Transcript, Mar. 24, 2006, 3:26pm.
STN Search Transcript, Mar. 28, 2006, 11:41 AM, "Preparation".
STN Search Transcript, Mar. 24, 2006 3:42pm.
Chintharalapalli S. et al., Mol. Cancer Res. 2007, 6(5), 1-11.
Whorwood, CB et al., "Licorice inhibits 11b-hydroxysteriod dehydrogenase messenger ribonucleic acid levels and potentiates glucocorticoid hormone action", Endrocrinology, 132:2287-2292, 1993.
Horigome, H et al., "Glycyrrhetinic acid induced apoptosis in murine splenocytes" Biol Pharm Bull, 24:54-58, 2001.
Horigome, H et al., Glycyrrhetinic acid-induced apoptosis in thymocytes: impact of 11b-hydroxysteriod dehydrogenase inhibition:, Am J Physiol, 277:E624-E630, 1999.
Armanini, D et al., "Effect of Licorice on the reduction of body fat mass in healthy subjects" J Endocrinol Invest 26:646-650, 2003. (Abstract only).
Armanini, D et al., "Glycyrrhetinic acid, the active principle of licorice, can reduce the thickness of subcutaneous thigh fat through topical fat", Steriods, 70:538-542, 2005.
Salvi, M. et al., "Glycyrrhetinic acid-inducded permeability transition in rat liver mitochondria", Biochem Pharmacol, 66:2375-2379, 2003.
Fiore, C. et al., "On the mechanism of mitochondrial permeability transition induction by glycyrrhetinic acid", Diochim Biophys Acta 1658:195-201, 2004.
Salvi, M. et al., "Carbenoxolone induces oxidative stress in liver mitochondria, which is responsible for transition pore opening", Endocrinology, 146:2306-2312, 2005.
Baltina LA., "Chemical modification of glycyrrhizic acid as a route to new bioactive compounds for medicine", Curr Med Chem, 10:155-171, 2003.
Ablise M. et al., "Synthesis and in vitro antioxidant activity of glycyrrhetinic acid derivatives tested with the cytochorme P450/NADPH system", Chem Pharm Bull (Toyoko) 52:1436:1439 (2004).
Honda T. et al., "New enone derivatives of oleanolic acid and ursolic acid as inhibitors of nitric oxide production in mouse macrophages", Bioorg Med Chem Lett 7:1623-1628, 1997.
Honda T. et al., "Novel synthetic oleanane and ursane triterpenoids with various enone functionalities in ring A as inhibitors of nitric oxide production in mouse macrophages", J Med Chem 43:1866-1877, 2000.
Honda T. et al., "Design and synthesis of 2-cyano-3, 12-dioxoolean-1,9-dien-28-oic acid, a novel and highly active inhibitor of nitric oxide production in mouse macrophages", Bioorg Med Chem Lett 8:2711-2714 (1998).
Couch RD. et al., "Studies on the reactivity of CDDO, a promising new chemopreventive and chemotherapeutic agent: implication for a molecular mechanism of action", Bioorg Med Chem Lett, 15:2215-2219, 2005.
Dinkova-Kostova AT, et al., "Extermely potent triterpenoid inducers of the phase 2 response: correlations of protection against oxidant and inflammatory stress", Proc Natl Acad Sci USA 102:4584-4589 (2005).

(Continued)

*Primary Examiner* — Barbara P Badio
(74) *Attorney, Agent, or Firm* — Richard S. Echler; Michael Fenwick; Patricia L. Folkins

(57) ABSTRACT

The present invention relates to novel derivatives of glycyrrhetinic acid, compositions comprising said derivatives and their use in the treatment of conditions or diseases that benefit from an upregulation of PPAR&ggr; and/or a downregulation of the expression or activity of one or more specificity (Sp) proteins, such as cancer, diabetes and Huntington's disease.

14 Claims, 21 Drawing Sheets

OTHER PUBLICATIONS

Wang, Y. et al., "A synthetic triterpeniod, 2-cyano-3, 12-dioxooleana-1, 9-dien-28-olic acid (CDDO), is a ligand for the peroxisome proliferator-activated receptor g", Mol Endorincol 14:1550-1556, (2000).

Lappillone H., et al., "Activation of peroxisome proliferator-activated receptor gamma by a novel synthetic triterpenoid 2-cyano-3, 12-dioxooleana-1,9-dien-28-oic acid induces growth arrest and apoptosis in breast cancer cells", Cancer Res 63:5926-5939, (2003).

Chintharlapalli S. et al., "2-Cyano-3, 12-dioxoolean-1, 9-dien-28-oic acid and related compounds inhibit growth of colon cancer cells through peroxisome proliferator-activated receptor gamma-dependent and-independent pathways" Mol Pharmacol 68:119-128 (2005).

Chintharlapalli S, et al., "Betulinic Acid Inhibits prostate cancer growth through inhibitors of specificity protein transcription factors", Cancer Res. 67:(c) Mar. 15, 2007. 2816-2822.

K.C. Nicolauo, et al., J. Am. Chem. Soc., 124. 2221-2232 (2002).

Chen, Zy et al., "15-deoxy-12,14, Prostaglandin J2 up regulates Kruppel-like factor 4 expression independent of peroxisome proliferator-activated receptor gamma by activating the mitogen-activated protein kinase kinase/extracelluar signal-regualted kinase signal transduction pathyway in HT-29 colon cancer cells" Mol Pharmacol, 68:1203-1213 (2005).

Chintharlapalli, S. et al., Mol. Cancer Thera. 2007, 6:1588-1598.

Samudio, I et al., "2-Cyano-3, 12 dioxoolean-1,9 diene-28-imidazolide (CDDO-Im) directly targets mitochondrial glutathione to induce apoptosis in pancreatic cancer", J Biol Chem, 280:36273-36282 (2005).

Konopleva, M et al., "Peroxisome proliferator-activated receptor gamma and retinoid X receptor ligands are potent inducers of differentiation and apoptosis in leukemias" Mol. Cancer Ther, 3:1249-1262 (2004).

Ito, Y et al., "The novel triterpenoid 2-cyano-3, 12-dioxolean-1, 9-dien-28-oci acid induces apoptosis of human myeloid leukaemia cells by a caspase-8-dependent mechanism" Cell Growth Differ, 11:261-267 (2000).

International Search Report for PCT/CA2007/001127, 2007.

International Preliminary Report on Patentability for PCT/CA2007/001127, 2009.

Japanese Examination Report, dated Aug. 9, 2012, for Application No. 2009-516837, Japanese equivalent of the present Application; (English Translation).

Japanese Examination Report, dated Aug. 9, 2012, for Application No. 2009-516837, Japanese equivalent of the present Application; (Japanese).

European Search Report, dated Aug. 2, 2012, for Application 07 720 042.6; European equivalent of the present Application.

Schiller, et al.,"Inhibition of Gap-Junctional Communication Induces the Trans-differentiation of Osteoblasts to an Adipocytic Phenotype in Vitro," J. Biological Chem. vol. 276, No. 17, Issue of Apr. 27, 2001, pp. 14133-14138.

GLYCYRRHETINIC ACID DERIVATIVES

CROSS-REFERENCE TO RELATED APPLICATIONS

The present application is a National Phase Application of International Application No. PCT/CA2007/001127, filed Jun. 27, 2007, which claims priority to U.S. Provisional Patent Application No. 60/816,590 filed Jun. 27, 2006, which applications are incorporated herein fully by this reference.

FIELD OF THE INVENTION

The present invention relates to novel glycyrrhetinic acid derivatives, pharmaceutical compositions comprising said derivatives and their use as therapeutics, in particular as a new class of anticancer drugs that act through multiple pathways.

BACKGROUND OF THE INVENTION

Licorice root extracts have been extensively used for their therapeutic properties which include the potentiation of cortisol action, inhibition of testosterone biosynthesis, reduction in body fat mass and other endocrine effects (1-4). The activities of these extracts are linked to different classes of phytochemicals particularly the major water soluble constituent glycyrrhizin and its hydrolysis product 18β-glycyrrhetinic acid (GA):

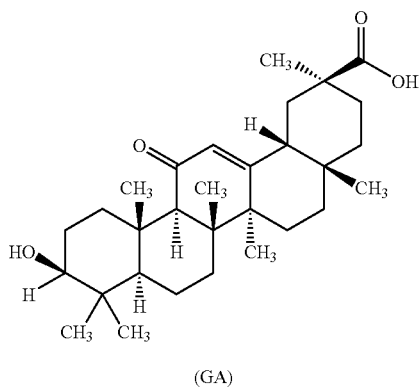

(GA)

Glycyrrhizin is a pentacyclic triterpenoid glycoside which is hydrolyzed in the gut to GA and many of the properties of licorice root can be attributed to GA. For example, GA inhibits 11β-hydroxysteroid dehydrogenase activity increasing corticosterone levels and this has been linked to apoptosis in murine thymocytes, splenocytes and decreased body fat index in human studies (5-9). GA also directly acts on mitochondria to induce apoptosis through increased mitochondrial swelling, loss of mitochondrial membrane potential and release of cytochrome C (10, 11).

GA has also been used as a template to synthesize bioactive drugs. For example carbenoxolone is the 3-hemisuccinate derivative of GA and this compound has been used for the treatment of gastritis and ulcers (12). Some of the activity of carbenoxolone may be due to hydrolysis to GA however carbenoxolone itself induced oxidative stress in liver mitochondria and decreased mitochondrial membrane potential. Other carboxyl and hydroxyl derivatives of glycyrrhetinic acid inhibit HIV and exhibit anti-inflammatory and immunomodulatory activities (13). In addition, GA derivatives containing a reduced carboxylic acid group ($CH_2OH$) at C-30 and some additional functional changes exhibited strong antioxidant activity (14).

GA is an oleanane derivative and there have been extensive structure-activity studies on the anti-inflammatory activities of oleanolic and ursolic acids derivatives (15-19). Two examples that have been prepared and studied are 2-cyano-3, 12-dioxo-oleana-1, 9(11)-diene-28-oic acid (CDDO) and its methyl ester (CDDO-Me) which contain major structural differences in the E-ring compared to GA:

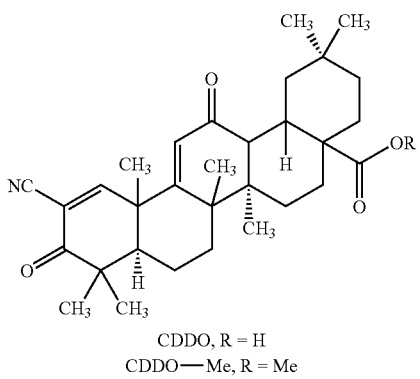

CDDO, R = H
CDDO—Me, R = Me

Subsequent studies have demonstrated that CDDO activates peroxisome proliferator-activated receptor γ (PPARγ) (20-22).

PPAR is a member of the nuclear receptor (NR) family of transcription factors (23-27), and the three members of this subfamily serve as regulators of lipid and carbohydrate metabolism and play a critical role in multiple diseases including diabetes, atherosclerosis and cancer. Ligand activation of PPARγ results in formation of a DNA-bound heterodimer with the retinoic acid X receptor (RXR) and after recruitment of the appropriate nuclear factors, transcriptional activation of target gene expression is observed. The assembly of a transcriptionally-active PPAR/RXR complexes may be highly variable and dependent on expression of coregulatory proteins, and this may dictate, in part, the tissue-specific and ligand structure-dependent activation of PPAR-mediated gene expression and responses.

PPARγ agonists have been developed for treatment of metabolic diseases, and thiazolidinediones (TZDs) are PPARγ agonists and are used by millions of patients in the United States for treatment of insulin-resistant Type II diabetes. PPARγ is overexpressed in multiple tumor-types (28), and there is evidence that various structural classes of PPARγ agonists inhibit growth and induce apoptosis in both pancreatic and colon cancer cells and tumors (29-50). However, it is clear from studies with PPARγ agonists that their effects in colon, pancreatic and other cancer cell lines and tumors are highly variable and can be mediated through receptor-dependent and -independent pathways. Nevertheless, this characteristic of multiple mechanisms can be advantageous for cancer chemotherapy by targeting several pathways that inhibit tumor growth and metastasis.

Specificity protein 1 (Sp1) was the first transcription factor identified (51), and the Sp/Krüppel-like factor (KLF) family of zinc finger transcription factors exhibit a broad range of tissue-specific and overlapping functions (52-56). Sp1 and Sp3 proteins are ubiquitously expressed and have been extensively investigated. For example, $Sp1^{-/-}$ embryos exhibit multiple abnormalities, retarded development and embryolethality on day 11 of gestation (57). Sp3$^{-/-}$ mice also exhibit growth retardation, defects in late tooth development, and the animals die at birth (58, 59). The critical requirement for Sp proteins during embryonic and postnatal development is in contrast to decreased expression in mature tissue/organs which are relatively quiescent. In contrast, there is increasing evidence that Sp1 (the major focus of most studies) and other Sp proteins such as Sp3 and Sp4 are overexpressed in tumors compared to most other tissues/organs (60-65). For example, a recent study compared the expression of Sp1, Sp3 and Sp4 in prostate and pancreatic tumors in xenograft or orthotopic mouse models, and results illustrated the high expression in LNCaP prostate tumor xenografts vs. normal mouse liver from the same animals (66, 67). Levels of Sp1, Sp3 and Sp4 expression were barely detectable in liver and other tissues compared to high levels of Sp1, Sp3 and Sp4 in tumors, and several studies report that Sp proteins are overexpressed in multiple tumors (60-65). Lou and coworkers (68) reported that transformation of fibroblasts resulted in an 8- to 18-fold increase in Sp1 expression, and these transformed cells formed highly malignant tumors in athymic nude mouse xenograft models, whereas untransformed fibroblasts expressing low levels of Sp1 did not form tumors. In addition, ribozyme-dependent knockdown of Sp1 in the transformed cells decreased VEGF expression and increased apoptosis. Recent studies in this laboratory using RNA interference and other techniques have demonstrated that knockdown of Sp1, Sp3, Sp4 and their combinations decreases cell cycle progression, increases p27 expression, decreases levels of the anti-apoptotic protein survivin, and downregulates expression of VEGF, VEGF receptor 1 (VEGFR1) and VEGFR2 (KDR) (66, 67, 69-72).

Since Sp proteins are overexpressed in tumors/cancer cells and play an important role in regulating expression of growth, angiogenic and survival genes, agents that target Sp protein degradation will be highly effective anticancer drugs. For example, the COX-2 inhibitor celecoxib decreased the expression of Sp1 and VEGF by inducing degradation of Sp1 in pancreatic cancer cells (73), and studies showed that COX-2 inhibitors decrease VEGF expression in colon cancer cells by decreasing the level of Sp1 and Sp3 (69). Further, a series of nonsteroidal anti-inflammatory drugs were screened for activity in decreasing Sp protein expression in pancreatic cancer cells (66). The results showed that only tolfenamic acid and structurally related analogs decreased Sp1, Sp3 and Sp4 expression in Panc1 and L3.6pl pancreatic cancer cells through activation of the proteasome pathway, and this was accompanied by decreased VEGF and VEGFR1 expression, increased apoptosis, and decreased cell growth. Moreover, in an orthotopic model for pancreatic cancer, tolfenamic acid decreased Sp protein expression in tumors, decreased tumor growth, decreased angiogenesis (and VEGF), and inhibited liver metastasis. Similar results were also observed using the triterpenoid natural product betulinic acid using LNCaP prostate cancer cells and tumors in a xenograft model (67). These results demonstrate that drugs that target Sp proteins constitute a highly effective and important class of mechanism-based anticancer drugs.

SUMMARY OF THE INVENTION

Certain novel derivatives of glycyrrhetinic acid (GA) have been prepared and shown to inhibit colon, pancreatic and prostate cancer cell growth and to induce peroxisome proliferator-activated receptor γ (PPARγ) transactivation as well as to induce specificity (Sp) protein degradation. The present invention therefore includes a novel class of new mechanism-based anticancer drugs that act as PPARγ agonists and by decreasing expression of Sp proteins in various tumor cells.

Accordingly, one aspect of the present invention includes a compound selected from a compound of formula (I):

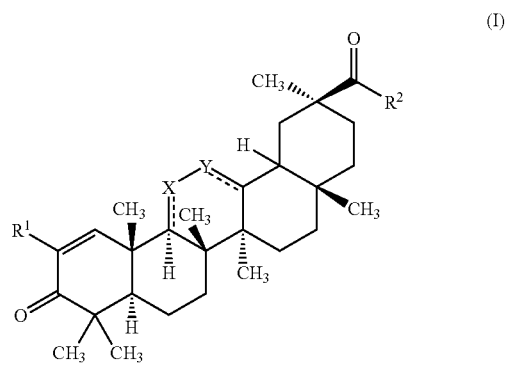

wherein
$R^1$ is selected from CN, halo, $NO_2$, $CO_2R^3$, $C_{1-6}$ alkyl, fluoro-substituted $C_{1-6}$alkyl, $C_{2-6}$alkenyl, $C_{2-6}$alkynyl, $OR^3$, $SR^3$, $SOR^3$, $SO_2R^3$, $NR^3R^4$, $C(O)NR^3R^4$, $C(O)R^3$, $OC(O)R^3$, $NHC(O)R^3$, $P(O)R^3R^4$, —C≡C—$R^3$, —$CR^3$=$CR^4R^5$, aryl and heteroaryl;
$R^2$ is selected from $OC_{1-6}$alkyl, fluoro-substituted $OC_{1-6}$alkyl, $NH_2$, $NHC_{1-6}$alkyl, $N(C_{1-6}$alkyl)($C_{1-6}$alkyl), SH and $SC_{1-6}$alkyl;
$R^3$, $R^4$ and $R^5$ are independently selected from H, $C_{1-6}$alkyl, fluoro-substituted $C_{1-6}$alkyl, aryl and heteroaryl; and
one of X and Y is C=O while the other is $CH_2$, and if X is C=O then === adjacent to X represents a single bond and === adjacent to Y represents a double bond and if Y is C=O then === adjacent to Y represents a single bond and === adjacent to X represents a double bond;
and pharmaceutically acceptable salts, solvates and prodrugs thereof.

The present invention also includes a pharmaceutical composition comprising a compound of the invention and a pharmaceutically acceptable carrier.

The present invention also includes a use of a compound of the invention as a medicament or as a diagnostic.

A further aspect of the present invention is a use of a compound of the invention to treat a condition or disease that benefits from an upregulation of PPARγ and/or a downregulation of the expression or activity of one or more specificity (Sp) proteins. In particular embodiments the condition or disease that benefits from an upregulation of PPARγ and/or a downregulation of the expression or activity of one or more specificity Sp proteins is cancer. Accordingly, also included within the scope of the present invention is a method of treating cancer comprising administering an effective amount of a compound of the invention to a subject in need thereof. Further the invention includes a use of a compound of the invention to treat cancer, as well as a use of a compound of the invention to prepare a medicament to treat cancer.

The present invention also includes a method of treating diabetes, comprising administering an effective amount of PPARγ-upregulating effective amount of a compound of the invention to a subject in need thereof. The invention also includes a use of a PPARγ-upregulating compound of the invention to treat diabetes as well as a use of a PPARγ-upregulating compound of the invention to prepare a medicament to treat diabetes.

A further aspect of the present invention is a method of treating Huntington's disease comprising administering an Sp protein-down-regulating effective amount of a compound of the invention to a subject in need thereof. Also included in the present invention is a use of an Sp protein-downregulating compound of the invention to treat Huntington's disease as well as a use of an Sp protein-downregulating compound of the invention to prepare a medicament to treat Huntington's disease.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

Definitions

Figure 1:
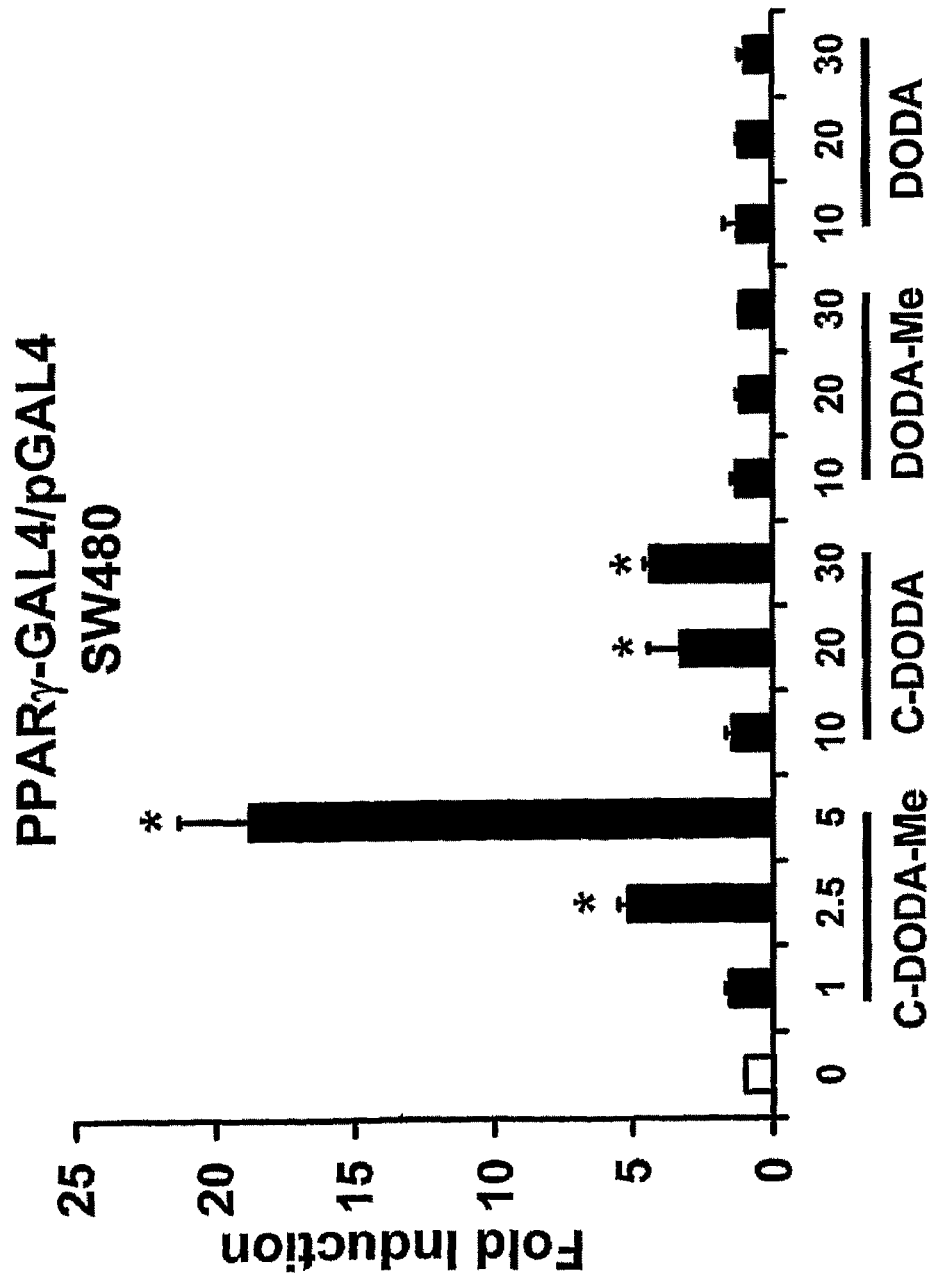
FIG. 1 shows ligand-dependent activation of PPARγ-GAL4/pGAL4 in SW480 cells. Cells were transfected with PPARγ-GAL4/pGAL4, treated with different concentrations of the triterpenoids, and luciferase activity was determined as described in the Examples. Results of all transactivation studies in this Figure are presented as means±SE for at least 3 separate determinations for each treatment group and significant ($p<0.05$) induction compared to solvent (DMSO) control is indicated by an asterisk.

The "compounds of the invention" include compounds of Formula I as hereinbefore defined, including all polymorphs and crystal habits thereof, salts, prodrugs and isomers thereof (including optical, geometric and tautomeric isomers) as hereinafter defined and isotopically-labeled compounds of Formula I.

Unless specified otherwise, the term "alkyl", when used alone or in combination with other groups or atoms, refers to a saturated straight or branched chain consisting solely of 1 to 6 hydrogen-substituted carbon atoms, suitably 1 to 4 hydrogen-substituted carbon atoms, and includes methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like.

Unless specified otherwise, the term "alkenyl" refers to a partially unsaturated straight or branched chain consisting solely of 2 to 6 hydrogen-substituted carbon atoms that contains at least one double bond, and includes vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like.

Unless specified otherwise, the term "alkynyl" refers to a partially unsaturated straight or branched chain consisting solely of 2 to 8 hydrogen-substituted carbon atoms that contains at least one triple bond, and includes ethynyl, 1-propynyl, 2-propynyl, 2-methylprop-1-ynyl, 1-butynyl, 2-butynyl, 3-butynyl, 1,3-butadiynyl, 3-methylbut-1-ynyl, 4-methylbutynyl, 4-methylbut-2-ynyl, 2-methylbut-1-ynyl, 1-pentynyl, 2-pentynyl, 3-pentynyl, 4-pentynyl, 1,3-pentadiynyl, 1,4-pentadiynyl, 3-methylpent-1-ynyl, 4-methylpent-2-ynyl, 4-methylpent-2-ynyl, 1-hexynyl and the like.

Unless specified otherwise, as used herein, the term aryl refers to an aromatic mono- or bicyclic group containing from 6 to 14 carbon atoms that may be optionally fused with a fully or partially saturated carbocyclic ring and may optionally be substituted with one or more substituents, suitably one to three substituents, independently selected from $C_{1-4}$alkyl, fluoro-substituted $C_{1-4}$alkyl, halo, $OC_{1-4}$alkyl, fluoro-substituted $OC_{1-4}$alkyl, $NO_2$ and CN. Examples of aryl groups include phenyl, naphthyl, indanyl and the like.

Unless specified otherwise, as used herein, the term heteroaryl refers to an aromatic mono- or bicyclic group containing from 5 to 14 carbon atoms, of which one to five is replaced with a heteroatom selected from N, S and O, that may optionally be substituted with one or more substituents, suitably one to three substituents, independently selected from $C_{1-4}$alkyl, fluoro-substituted $C_{1-4}$alkyl, halo, $OC_{1-4}$alkyl, fluoro-substituted $OC_{1-4}$alkyl, $NO_2$ and CN. Examples of aryl groups include thienyl, benzimidazolyl, benzo[b]thienyl, furanyl, benzofuranyl, pyranyl, isobenzofuranyl, chromenyl, xanthenyl, pyrrolyl, imidazolyl, pyrazolyl, pyridyl, pyrazinyl, pyrimidinyl, pyridazinyl, indolizinyl, isoindolyl, indolyl, indazolyl, purinyl, quinolizinyl, isoquinolyl, quinolyl, and the like.

Unless specified otherwise, the term "fluoro-substituted" as used herein means that, in the group being described, one or more, including all, of the hydrogen atoms has been replaced by F. For example, a fluoro-substituted alkyl includes trifluoromethyl, trifluoroethyl, pentafluoroethyl and the like.

Unless specified otherwise, as used herein, the terms "halogen" and "halo" include F, Cl, Br, and I.

Under standard nomenclature rules used throughout this disclosure, the point of attachment of the designated side chain is described first followed by the adjacent functionality toward the terminal portion. A substituent's point of attachment may also be indicated by a dashed line to indicate the point(s) of attachment, followed by the adjacent functionality and ending with the terminal functionality.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "pharmaceutically acceptable" means compatible with the treatment of animals, in particular, humans.

The term "pharmaceutically acceptable salt" includes both pharmaceutically acceptable acid addition salts and pharmaceutically acceptable basic addition salts.

The term "pharmaceutically acceptable acid addition salt" as used herein means any non-toxic organic or inorganic salt of any base compound of the disclosure, or any of its intermediates. Basic compounds of the disclosure that may form an acid addition salt include, for example, where the $R^1$ and/or $R^2$ is substituted with $NH_2$, $NHC_1$-$C_6$alkyl or $N(C_1$-$C_6$alkyl)($C_1$-$C_6$alkyl). Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of the compounds of the disclosure are more soluble in water and various hydrophilic organic solvents, and generally demonstrate higher melting points in comparison to their free base forms. The selection of the appropriate salt will be known to one skilled in the art. Other non-pharmaceutically acceptable acid addition salts, e.g. oxalates, may be used, for example, in the isolation of the compounds of the disclosure, for laboratory use, or for subsequent conversion to a pharmaceutically acceptable acid addition salt.

The term "pharmaceutically acceptable basic salt" as used herein means any non-toxic organic or inorganic basic addition salt of any acid compound of the invention, or any of its intermediates, which are suitable for or compatible with the treatment of animals, in particular humans. Acidic compounds of the invention that may form a basic addition salt include, for example, those where $R^1$ is C(O)OH. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art. Other non-pharmaceutically acceptable basic addition salts, may be used, for example, in the isolation of the compounds of the invention, for laboratory use, or for subsequent conversion to a pharmaceutically acceptable acid addition salt. The formation of a desired compound salt is achieved using standard techniques. For example, the neutral compound is treated with a base in a suitable solvent and the formed salt is isolated by filtration, extraction or any other suitable method.

The term "cancer" as used herein refers to a class of diseases or disorders characterized by uncontrolled division of cells and the ability of these cells to invade other tissues, either by direct growth into adjacent tissue through invasion or by implantation into distant sites by metastasis. Metastasis is defined as the stage in which cancer cells are transported through the bloodstream or lymphatic system. Examples of cancer that may be treated using the compounds of the invention include those that benefit from an up-regulation of the activity of PPARγ relative to normal cells and/or that benefit from a downregulation of the expression and/or activity of specificity proteins (Sp), in particular Sp1, Sp3 and/or Sp4. Examples of such cancers include, but are not limited to, prostate cancer, colon cancer, breast cancer, bladder cancer, lung cancer, ovarian cancer, endometrial cancer renal cancer and pancreatic cancer. Suitably the cancer is prostate cancer, colon cancer or pancreatic cancer.

The term a "therapeutically effective amount", "effective amount" or a "sufficient amount" of a compound of the present invention is a quantity sufficient to, when administered to the subject, including a mammal, for example a human, effect beneficial or desired results, including clinical results, and, as such, an "effective amount" or synonym thereto depends upon the context in which it is being applied. For example, in the context of upregulating PPARγ, for example, it is an amount of the compound sufficient to achieve such an upregulation of PPARγ activity as compared to the response obtained without administration of the compound. In the context of downregulating the expression and/or activity of Sp proteins, for example, it is an amount of the compound sufficient to achieve such a downregulation as compared to the response obtained without administration of the compound. In the context of disease, therapeutically effective amounts of the compounds of the present invention are used to treat, modulate, attenuate, reverse, or affect a disease or conditions that benefits from an upregulation of PPARγ activity and/or downregulation of the expression and/or activity of Sp proteins, for example, cancer in a subject. An "effective amount" is intended to mean that amount of a compound that is sufficient to treat, prevent or inhibit such diseases or conditions. The amount of a given compound of the present invention that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, a "therapeutically effective amount" of a compound of the present invention is an amount which prevents, inhibits, suppresses or reduces a disease or conditions that benefits from an upregulation of PPARγ activity and/or downregulation of the expression and/or activity of Sp proteins, for example, cancer as determined by clinical symptoms or the amount of cancer cells, in a subject as compared to a control. As defined herein, a therapeutically effective amount of a compound of the present invention may be readily determined by one of ordinary skill by routine methods known in the art.

In an embodiment, a therapeutically effective amount of a compound of the present invention ranges from about 0.1 to about 40 mg/kg body weight, suitably about 1 to about 10 mg/kg body weight, and more suitably, from about 2 to about 5 mg/kg body weight. The skilled artisan will appreciate that certain factors may influence the dosage required to effectively treat a subject, or prevent a subject, suffering from a disease or conditions that benefits from an upregulation of PPARγ activity and/or downregulation of the expression and/or activity of Sp proteins, for example cancer, and these factors include, but are not limited to, the severity of the disease or disorder, previous treatments, the general health and/or age of the subject and other diseases present.

Moreover, a "treatment" or "prevention" regime of a subject with a therapeutically effective amount of the compound of the present invention may consist of a single administration, or alternatively comprise a series of applications. For example, the compound of the present invention may be administered at least once a week. However, in another embodiment, the compound may be administered to the subject from about one time per week to about once daily for a given treatment. The length of the treatment period depends on a variety of factors, such as the severity of the disease, the age of the patient, the concentration and the activity of the compounds of the present invention, or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required.

As used herein, "administered contemporaneously" means that two substances are administered to a subject such that they are both biologically active in the subject at the same time. The exact details of the administration will depend on the pharmacokinetics of the two substances in the presence of each other, and can include administering one substance within 24 hours of administration of the other, if the pharmacokinetics are suitable. Designs of suitable dosing regimens are routine for one skilled in the art. In particular embodiments, two substances will be administered substantially simultaneously, i.e. within minutes of each other, or in a single composition that comprises both substances.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with cancer or manifesting a symptom associated with cancer.

To "inhibit" or "suppress" or "reduce" or "downregulate" a function or activity, such Sp protein expression or activity, is to reduce the function or activity when compared to otherwise same conditions except for a condition or parameter of interest, or alternatively, as compared to another conditions.

To "increase" or "upregulate" a function or activity, such as PPARγ activity, is to increase the function or activity when compared to otherwise same conditions except for a condition or parameter of interest, or alternatively, as compared to another conditions.

The term "subject" or "patient" or synonym thereto, as used herein includes all members of the animal kingdom, especially mammals, including human. The subject or patient is suitably a human.

The term "a cell" as used herein includes a plurality of cells. Administering a compound to a cell includes in vivo, ex vivo and in vitro treatment.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Unless otherwise indicated, the terms "a", "an" and "the" as used herein mean one or more that one.

Compounds of the Invention

A new class of compounds derived from glycyrrhetinic acid (GA), the active component of licorice which has been widely used for medicinal purposes, has been identified as anticancer drugs that inhibit tumor growth, metastasis and survival. Results show that a 2-cyano derivative of GA, namely methyl 2-cyano-3,11-dioxo-18β-olean-1,12-dien- 30-oate (β-CDODA-Me) and the corresponding 18α isomer (α-CDODA-Me), along with structurally related analogs, both activate PPARγ and induce Sp protein degradation in colon and pancreatic cancer cells. Accordingly, CDODA-Me and related compounds are a novel class of new mechanism-based anticancer drugs that act as PPARγ agonists and by decreasing expression of Sp proteins in pancreatic and colon cancer.

Accordingly, in one of its aspect, the present invention includes a compound selected from a compound of Formula (I):

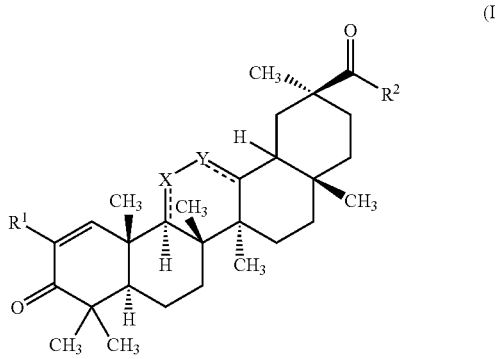

(I)

wherein
$R^1$ is selected from CN, halo, $NO_2$, $CO_2R^3$, $C_{1-6}$alkyl, fluoro-substituted $C_{1-6}$alkyl, $C_{2-6}$alkenyl, $C_{2-6}$alkynyl, $OR^3$, $SR^3$, $SOR^3$, $SO_2R^3$, $NR^3R^4$, $C(O)NR^3R^4$, $C(O)R^3$, $OC(O)R^3$, $NHC(O)R^3$, $P(O)R^3R^4$, —C≡C—$R^3$, —$CR^3$=$CR^4R^5$, aryl and heteroaryl;
$R^2$ is selected from $OC_{1-6}$alkyl, fluoro-substituted $OC_{1-6}$alkyl, $NH_2$, $NHC_{1-6}$alkyl, $N(C_{1-6}$alkyl$)(C_{1-6}$alkyl$)$, SH and $SC_{1-6}$alkyl;
$R^3$, $R^4$ and $R^5$ are independently selected from H, $C_{1-6}$alkyl, fluoro-substituted $C_{1-6}$alkyl, aryl and heteroaryl; and
one of X and Y is C=O while the other is $CH_2$, and if X is C=O then ═ adjacent to X represents a single bond and ═ adjacent to Y represents a double bond and if Y is C=O then ═ adjacent to Y represents a single bond and ═ adjacent to X represents a double bond;
and pharmaceutically acceptable salts, solvates and prodrugs thereof.

In an embodiment of the present invention, $R^1$ is selected from CN, halo, $NO_2$, $CO_2H$, $CO_2C_{1-6}$alkyl, $C_{1-6}$alkyl, fluoro-substituted $C_{1-6}$alkyl, $C_{2-6}$alkenyl, $C_{2-6}$alkynyl, $OC_{1-6}$alkyl, fluoro-substituted $OC_{1-6}$alkyl, OH, SH, $SC_{1-6}$alkyl, $SOC_{1-6}$alkyl, $SO_2C_{1-6}$alkyl, $NH_2$, $NHC_{1-6}$alkyl, $N(C_{1-6}$alkyl$)(C_{1-6}$alkyl$)$, $C(O)NH_2$, $C(O)NHC_{1-6}$alkyl, $C(O)N(C_{1-6}$alkyl$)(C_{1-6}$alkyl$)$, $C(O)C_{1-6}$alkyl, $OC(O)C_{1-6}$alkyl and $NHC(O)C_{1-6}$alkyl. In a further embodiment of the invention, $R^1$ is selected from CN, halo, $NO_2$, $CO_2H$, $CO_2C_{1-4}$alkyl, $C_{1-4}$alkyl, fluoro-substituted $C_{1-4}$alkyl, $C_{2-4}$alkenyl, $C_{2-4}$alkynyl, $OC_{1-4}$alkyl, fluoro-substituted $OC_{1-4}$alkyl, OH, SH, $SC_{1-4}$alkyl, $SOC_{1-4}$alkyl, $SO_2C_{1-4}$alkyl, $NH_2$, $NHC_{1-4}$alkyl, $N(C_{1-4}$alkyl$)(C_{1-4}$alkyl$)$, $C(O)NH_2$, $C(O)NHC_{1-4}$alkyl, $C(O)N(C_{1-4}$alkyl$)(C_{1-4}$alkyl$)$, $C(O)C_{1-4}$alkyl, $OC(O)C_{1-4}$alkyl and $NHC(O)C_{1-4}$alkyl. In another embodiment of the present invention $R^1$ is selected from CN, halo, $CO_2H$, $CO_2C_{1-4}$alkyl, $C_{1-4}$alkyl, fluoro-substituted $C_{1-4}$alkyl, $OC_{1-4}$alkyl, fluoro-substituted $OC_{1-4}$alkyl and OH. In further embodiments of the invention, $R^1$ is selected from CN, Cl, Br, I, F, $CO_2H$, $CO_2CH_3$, $CH_3$, $CF_3$, $OCH_3$, $OCF_3$ and OH. In still further embodiments of the invention, $R^1$ is CN, $CF_3$ or I.

In an embodiment of the invention $R^2$ is selected from $OC_{1-4}$alkyl, fluoro-substituted $OC_{1-4}$alkyl, $NH_2$, $NHC_{1-4}$alkyl, $N(C_{1-4}$alkyl$)(C_{1-4}$alkyl$)$, SH and $SC_{1-4}$alkyl. In further embodiments of the invention $R^2$ is selected from $OC_{1-4}$alkyl and fluoro-substituted $OC_{1-4}$alkyl. In still further embodiments of the invention, $R^2$ is selected from $OCH_2CH_3$, $OCH_3$ and $OCF_3$. In still further embodiments of the invention, $R^2$ is $OCH_3$.

In an embodiment of the invention $R^3$, $R^4$ and $R^5$ are independently selected from H, $C_{1-4}$alkyl, fluoro-substituted $C_{1-4}$alkyl and phenyl. In a further embodiment, $R^3$, $R^4$ and $R^5$ are independently selected from H, methyl and $CF_3$.

In an embodiment of the invention one of X is C=O and Y is $CH_2$, ═ adjacent to X represents a single bond and ═ adjacent to Y represents a double bond providing the following compounds of Formula I:

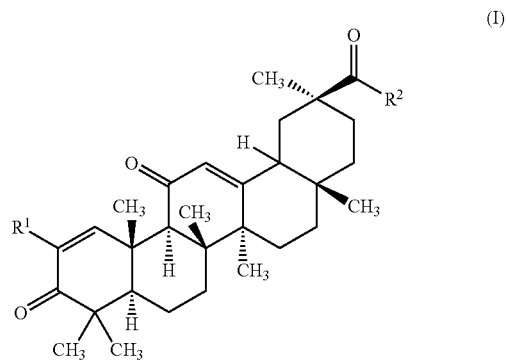

(I)

The compounds of Formula I include those having either the α or β configuration at carbon 18 or mixtures thereof in any ratio. Accordingly, in an embodiment of the invention, the compound of Formula I is selected from:

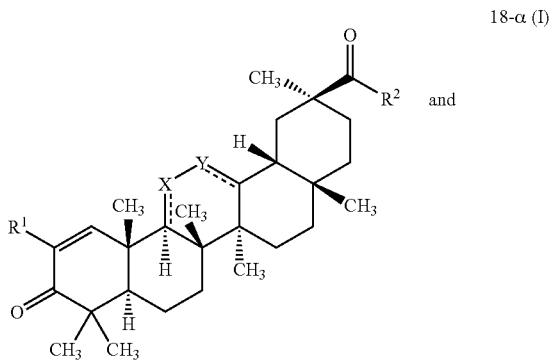

18-α (I) and

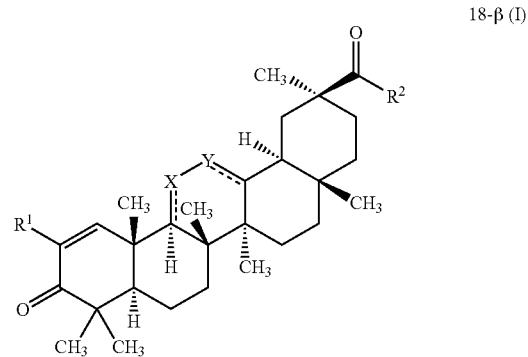

18-β (I)

and mixtures thereof in any ratio. It is to be understood that while the stereochemistry of the compounds of the invention may be as shown above in any given compound listed herein, such compounds of the invention may also contain certain amounts (e.g. less than 20%, preferably less than 10%, more preferably less than 5%) of compounds of the invention having alternate stereochemistry.

In an embodiment of the invention, the compound of Formula I is selected from:
2-cyano-3,11-dioxo-18β-oleana-1,12-dien-30-oic acid methyl ester;
2-cyano-3,11-dioxo-18α-oleana-1,12-dien-30-oic acid methyl ester;
2-iodo-3,11-dioxo-18β-oleana-1,12-dien-30-oic acid methyl ester;
2-iodo-3,11-dioxo-18α-oleana-1,12-dien-30-oic acid methyl ester;
2-trifluoromethyl-3,11-dioxo-18β-oleana-1,12-dien-30-oic acid methyl ester; and
2-trifluoromethyl-3,11-dioxo-18α-oleana-1,12-dien-30-oic acid methyl ester.

In a further embodiment of the invention, the compound of Formula I is 2-cyano-3,11-dioxo-18β-oleana-1,12-dien-30-oic acid methyl ester.

The compounds of the invention may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

The compounds of the invention may also exist in unsolvated and solvated forms. The term "solvate" is used herein to describe a molecular complex comprising the compound of the invention and one or more pharmaceutically acceptable solvent molecules, for example, ethanol. The term "hydrate" is employed when said solvent is water. A currently accepted classification system for organic hydrates is one that defines isolated site, channel, or metal-ion coordinated hydrates (see Polymorphism in Pharmaceutical Solids by K. R. Morris, Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Herein all references to compounds of Formula I include references to salts, solvates, prodrugs and multi-component complexes thereof.

The compounds of Formula I can be prepared using methods known in the art, for example, 18α- and 18β-glycyrrhetinic acid and their methyl esters may be converted into the corresponding dienones by reaction with 2-iodoxybenzoic acid as per a reported method (74). The corresponding 1-saturated-2-cyano 18β-glycyrrhetinic acid and 1-saturated-2-cyano 18α-glycyrrhetinic acid and their methyl esters are known (75) and may be reacted with 2,3-dichloro-5,6-dicyano-1,4-benzoquinone (DDQ) to give the corresponding 2-cyano-dienones. Further, dienones of 18α- and 18β-glycyrrhetinic acid and their methyl esters may be iodinated at position 3 by reacting with iodine and pyridine in an ether solvent as described in the Examples herein.

The present invention includes radiolabeled forms of the compounds of the invention, for example, compounds of the invention labeled by incorporation within the structure $^3$H, $^{11}$C or $^{14}$C or a radioactive halogen such as $^{125}$I and $^{18}$F. A radiolabeled compound of the invention may be prepared using standard methods known in the art. For example, tritium may be incorporated into a compound of the invention using standard techniques, for example by hydrogenation of a suitable precursor to a compound of the invention using tritium gas and a catalyst. Alternatively, a compound of the invention containing radioactive iodo may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, for example hexamethylditin in the presence of tetrakis(triphenylphosphine) palladium (0) in an inert solvent, such as dioxane, and at elevated temperatures, suitably 50-100° C. Further, a compound of the invention containing a radioactive fluorine may be prepared, for example, by reaction of K[$^{18}$F]/K222 with a suitable precursor compound, such as a compound of Formula I comprising a suitable leaving group, for example a tosyl group, that may be displaced with the $^{18}$F anion.

Methods and Compositions

The present invention relates to novel compounds of Formula I, accordingly the present invention includes all uses of these compounds including, for example, in therapeutic and diagnostic applications.

The present invention accordingly includes the use of a compound of the invention as a medicament or as a diagnostic.

In their ability to upregulate PPARγ, certain compounds of the invention are useful for treating any condition or disease that benefits from an upregulation of PPARγ. In an embodiment of the invention, the condition or disease that that benefits from an upregulation of PPARγ is diabetes and cancer.

Accordingly, the present invention includes a method of treating cancer comprising administering an effective amount of a compound of the invention to a subject in need thereof. The invention also includes a use of a compound of the invention to treat cancer and a use of a compound of the invention to prepare a medicament to treat cancer. In embodiments of the invention the cancer is selected from prostate cancer and gastrointestinal cancers, for example, colon cancer and pancreatic cancer.

The present invention also includes a method of treating cancer comprising administering an effective amount of a compound of the invention to a subject in need thereof. Further the invention includes a use of a compound of the invention to treat cancer, as well as a use of a compound of the invention to prepare a medicament to treat cancer.

In an embodiment of the invention, there is included a method of treating diabetes, in particular insulin dependent type II diabetes, comprising administering an effective amount of PPARγ-upregulating effective amount of a compound of the invention to a subject in need thereof. The present invention also includes a use of a PPARγ-upregulating compound of the invention to treat diabetes as well as a use of a PPARγ-upregulating compound of the invention to prepare a medicament to treat diabetes. In an embodiment of the invention the PPARγ-upregulating compound is 2-cyano-3,11-dioxo-18β-oleana-1,12-dien-30-oic acid methyl ester. A person skilled in the art would be able to identify PPARγ-upregulating compounds of the invention using, for example, using cell lines transfected with PPARγ-GAL4 as described in the Examples hereinbelow and in Chintharlapalli, S. et al. Mol. Cancer. Therap. 6:1588, 2007.

In their ability to downregulate the expression or activity of Sp proteins, the compounds of the invention are useful for treating any condition or disease that benefits from a downregulation in the expression or activity of Sp proteins. In an embodiment of the invention, the condition or disease that that benefits from a downregulation in the expression or activity of Sp proteins, in particular Sp1, is Huntington's disease. The benefit provided to the pathology of Huntington's disease by suppressing the expression and/or activity of Sp1 has been reported by Qiu, Z. et al. J. Biol. Chem. 281:16672, 2006.

Accordingly, in a further embodiment of the present invention, there is included a method of treating Huntington's disease comprising administering an Sp protein-downregulating effective amount of a compound of the invention to a subject in need thereof. The present invention also includes a use of an Sp protein-downregulating compound of the invention to treat diabetes as well as a use of an Sp protein-downregulating compound of the invention to prepare a medicament to treat diabetes. In an embodiment of the invention the Sp protein is Sp 1, Sp3 and/or Sp4. A person skilled in the art would be able to identify Sp protein-downregulating compounds of the invention by contacting one or more cells with a compound of the invention and assaying for the presence of one or more of the Sp proteins and comparing the levels of Sp proteins in the one or more cells with that of controls. Such methods are known in the art (66, 67) and are described in the Examples hereinbelow.

The compounds of the invention are suitably formulated into pharmaceutical compositions for administration to human subjects in a biologically compatible form suitable for administration in vivo. Accordingly, in another aspect, the present invention includes a pharmaceutical composition comprising a compound of the invention and a pharmaceutically acceptable carrier or diluent.

The compositions containing the compounds of the invention can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (2003-20th edition) and in The United States Pharmacopeia: The National Formulary (USP 24 NF 19) published in 1999. On this basis, the compositions include, albeit not exclusively, solutions of the substances in association with one or more pharmaceutically acceptable vehicles or diluents, and contained in buffered solutions with a suitable pH and iso-osmotic with the physiological fluids.

In accordance with the methods of the invention, the described compounds, salts or solvates thereof may be administered to a patient in a variety of forms depending on the selected route of administration, as will be understood by those skilled in the art. The compositions of the invention may be administered, for example, by oral, parenteral, buccal, sublingual, nasal, rectal, patch, pump or transdermal (topical) administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations.

The pharmaceutical forms suitable for injectable use include sterile aqueous solutions or dispersion and sterile powders for the extemporaneous preparation of sterile injectable solutions or dispersions. In all cases the form must be sterile and must be fluid to the extent that easy syringability exists. Ampoules are convenient unit dosages.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Compositions for topical administration may include, for example, propylene glycol, isopropyl alcohol, mineral oil and glycerin. Preparations suitable for topical administration include liquid or semi-liquid preparations such as liniments, lotions, applicants, oil-in-water or water-in-oil emulsions such as creams, ointments or pastes; or solutions or suspensions such as drops. In addition to the aforementioned ingredients, the topical preparations may include one or more additional ingredients such as diluents, buffers, flavouring agents, binders, surface active agents, thickeners, lubricants, preservatives, e.g. methyl hydroxybenzoate (including antioxidants), emulsifying agents and the like.

Sustained or direct release compositions can be formulated, e.g. liposomes or those wherein the active compound is protected with differentially degradable coatings, such as by microencapsulation, multiple coatings, etc. It is also possible to freeze-dry the compounds of the invention and use the lypolizates obtained, for example, for the preparation of products for injection.

The compounds of the invention may be administered to a subject alone or in combination with pharmaceutically acceptable carriers, as noted above, and/or with other pharmaceutically active agents for the treatment of psychosis, the proportion of which is determined by the solubility and chemical nature of the compounds, chosen route of administration and standard pharmaceutical practice.

The dosage of the compounds of Formula I and/or compositions of the invention can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. The compounds of Formula I may be administered initially in a suitable dosage that may be adjusted as required, depending on the clinical response. For ex vivo treatment of cells over a short period, for example for 30 minutes to 1 hour or longer, higher doses of compound may be used than for long term in vivo therapy.

The compounds of Formula I, or salts or solvates thereof, can be used alone or in combination with other agents or therapies, for example other agents or therapies that treat cancer, for example, but not limited to, cytotoxic drugs, kinase inhibitors, antibodies and immunotherapy, selective receptor modulators, non-steroidal anti-inflammatory drugs (NSAIDS) and enzyme modulators While the following Examples illustrate the invention in further detail, it will be appreciated that the invention is not limited to the specific Examples.

EXAMPLES

Materials and Methods for Examples 1-6

Melting points were determined with a Kofler hot-stage apparatus. $^1$H NMR spectra were run in CDCl$_3$ on a Bruker Avance-400 spectrometer using Me$_4$Si as an internal standard. For analytical and preparative use, TLC plates were spread with Silica Gel 60 GF (Merck). Silica for column chromatography was obtained from Selecto Scientific. Elemental microanalyses were carried out by Guelph Chemical Laboratories Ltd. 18β-Glycyrrhetinic acid was purchased from Aldrich.

Example 1(a)

3,11-Dioxo-18β-oleana-1,12-dien-30-oic acid

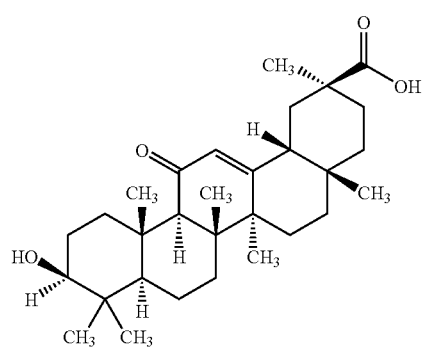

-continued

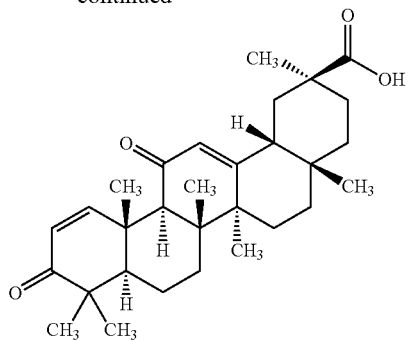

A mixture of 18β-glycyrrhetinic acid (157 mg, 0.3333 mmol) and 2-iodoxybenzoic acid (24) (373.4 mg, 1.333 mmol, 4 equiv) in dimethyl sulfoxide (7 mL, freshly distilled from CaH$_2$) was stirred with heating at 85° C. for 21 h. After cooling, the solution was poured into water (100 mL) giving a white precipitate. This precipitate did not dissolve when Et$_2$O (50 mL) was added. It was collected and washed with water and the ether layer recovered, dried and evaporated. After drying, the precipitate was washed thoroughly with MeOH/CH$_2$Cl$_2$ (1:9). The solution obtained was evaporated and the resulting solid combined with that recovered earlier from the ether extract. This material (381.6 mg) was triturated with EtOAc (5 mL) to give a free-flowing fine white suspension that was filtered off and washed several times with EtOAc. The combined filtrates when evaporated, in vacuo, gave a white solid (176.1 mg) which was subjected to preparative scale TLC using MeOH/CH$_2$Cl$_2$ (1:19) as eluant. The main band gave the title compound as a white solid (133.1 mg, 85.5%) which, on crystallization from MeOH, gave colorless prisms (104.7 mg), mp 270-5° C. $^1$H NMR δ 7.746 (1H, d, J=10.4 Hz, C1-H), 5.816 (1H, d, J=10.4 Hz, C2-H), 5.817 (1H, s, C12-H), 2.691 (1H, s, C9-H), 1.422, 1.401, 1.245, 1.191, 1.169, 1.118, 0.872 (all 3H, s, CMe). Anal C$_{30}$H$_{42}$O$_4$ (C, H).

(b) 3,11-Dioxo-18α-oleana-1,12-dien-30-oic acid

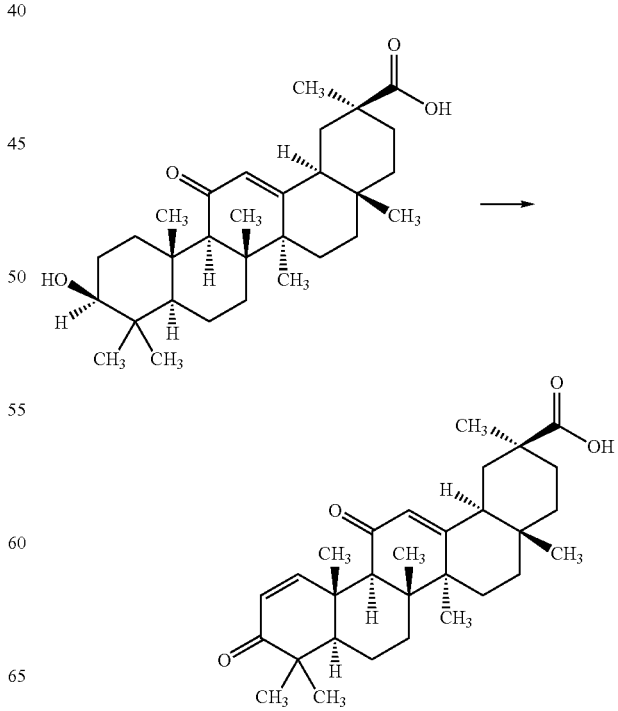

In a like manner, 3,11-dioxo-18α-oleana-1,12-dien-30-oic acid was prepared from 18α-glycyrrhetinic acid (which was purchased from Sigma-Aldrich).

Example 2(a)

Methyl 3,11-dioxo-18β-oleana-1,12-dien-30-oate

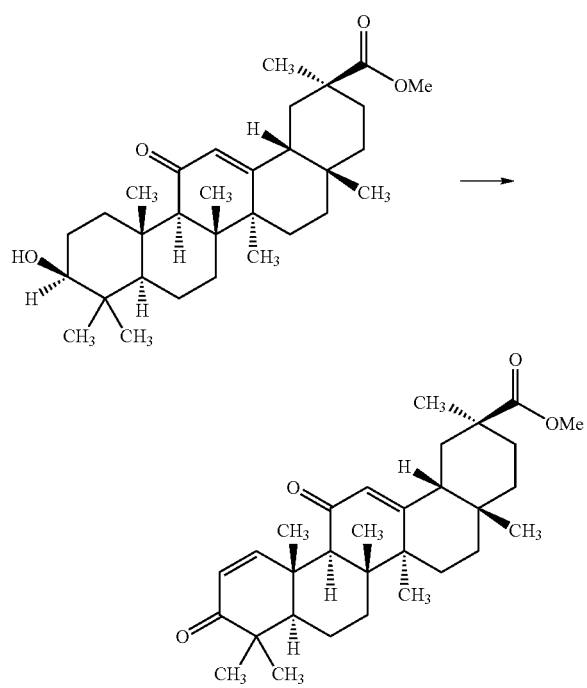

Methyl 18β-glycyrrhetinate was prepared by diazomethylation of 18β-glycyrrhetinic acid and a sample (161.6 mg, 0.3333 mmol) reacted with the IBX reagent (373.4 mg, 1.333 mmol, 4 equiv) as described in Example 1 for the parent acid. After a similar work-up, the recovered product (375.7 mg) was triturated with EtOAc, the derived suspension filtered off and washed with more solvent. Evaporation of the combined filtrates gave an off-white solid (256.7 mg) which showed one major band on preparative TLC (MeOH/CH$_2$Cl$_2$; 1:19). This band gave the title compound as a colorless solid (155.3 mg, 96.9%), which on crystallization from MeOH/H$_2$O (4:1) and washing with fresh solvent (3×0.5 mL, rather soluble), gave clear, flat needles (140.2 mg), mp 192-4° C. $^1$H NMR δ 7.745 (1H, d, J=10.0 Hz, C1-H), 5.812 (1H, d, J=10.0 Hz, C2-H), 5.770 (1H, s, C12-H), 3.078 (3H, s, OMe), 2.681 (1H, s, C9-H), 1.419, 1.390, 1.184, 1.166, 1.159, 1.118, 0.833 (all 3H, s, CMe). Anal C$_{31}$H$_{44}$O$_4$ (C, H).

(b) Methyl 3,11-dioxo-18α-oleana-1,12-dien-30-oate

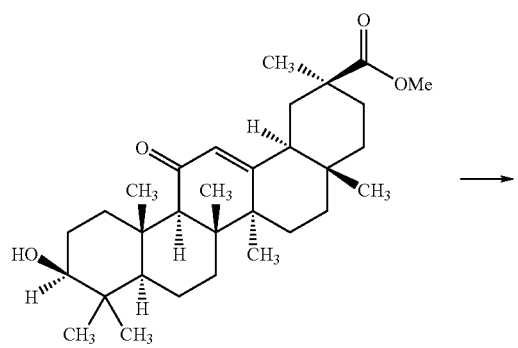

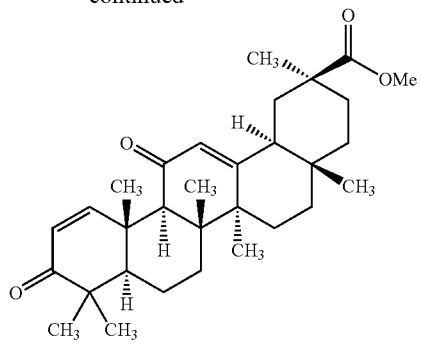

In a like manner methyl 3,11-dioxo-18α-oleana-1,12-dien-30-oate was prepared from methyl 18α-glycyrrhetinate.

Example 3(a)

2-cyano-3,11-dioxo-18β-oleana-1,12-dien-30-oic acid

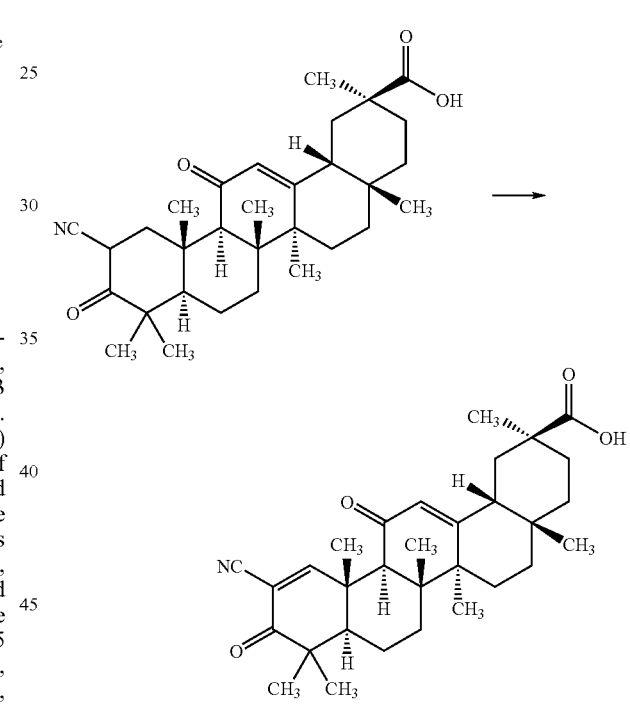

2-Cyano-3,11-dioxo-18β-oleana-12-en-30-oic acid was prepared from 18β-glycyrrhetinic acid as previously described (25) of this compound and DDQ (16) (247.0 mg, 1.088 mmol) in dry benzene (55 mL) was heated to reflux, with stirring, for 6 h. Upon cooling, the reaction mixture was filtered and the collected solid washed with benzene. The orange filtrate and washings were combined and evaporated to give a dark gum that showed one major, but many minor products on TLC (MeOH/CH$_2$Cl$_2$, 1:19; or EtOAc/hexane, 1:1, run twice). Preparative TLC, using the latter conditions, and recovery of the material from the main band gave the title compound (149.2 mg, 33.7%) as a yellow gum which solidified on standing. This material was crystallized twice from EtOAc/hexane to afford a granular pale yellow solid (55.5 mg), mp 195-7° C., which appeared to be essentially pure (by TLC and $^1$H NMR). $^1$H NMR δ 8.550 (1H, s, C1-H), 5.846 (1H, s, C12-H), 2.2.715 (1H, s, C9-H), 1.455, 1.404, 1.255, 1.225, 1.200, 1.162, 0.876 (all 3H, s, CMe). Anal C$_{31}$H$_{41}$NO$_4$ (C, H, N).

(b) 2-cyano-3,11-dioxo-18α-oleana-1,12-dien-30-oic acid

In a like manner, 2-cyano-3,11-dioxo-18α-oleana-1,12-dien-30-oic acid was prepared from 18α-glycyrrhetinic acid.

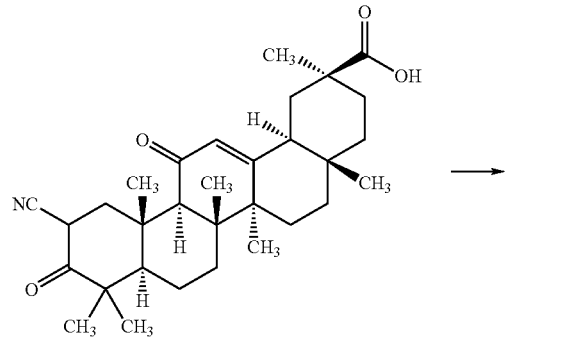

Example 4(a)

Methyl 2-cyano-3,11-dioxo-18β-oleana-1,12-dien-30-oate

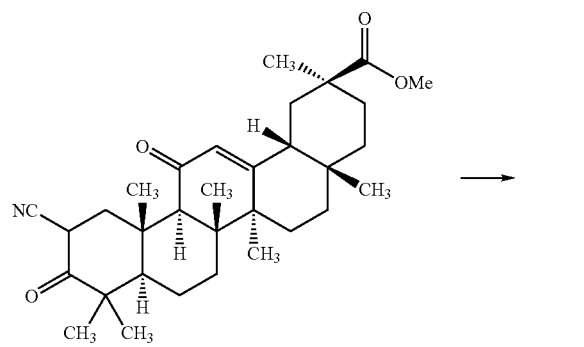

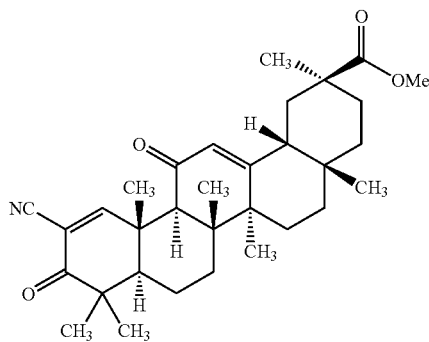

Methyl 2-cyano-3,11-dioxo-18β-oleana-12-en-30-oate was also prepared from methyl 18β-3-glycyrrhetinate as previously described (25) and a solution of the ester (246.9 mg, 0.4863 mmol) and DDQ (134.1 mg, 0.5905 mmol) in dry benzene (20 mL) was heated to reflux for 5 h. The resulting clear solution, on cooling, deposited a fine rust-colored solid, which was filtered off. Evaporation of the filtrate, in vacuo, left a clear orange gum showing one major spot on TLC (EtOAc/hexane; 1:3). Preparative TLC of this gum using the same eluant afforded two bands: a main band, containing essentially pure ($^1$H NMR) title compound (156.9 mg, 63.8%) and a slightly more polar band containing some of the title compound ($^1$H NMR) and other unidentified material (55.5 mg). Crystallization of the former from EtOAc/hexane gave tight clumps of small white crystals (137.9 mg), mp 243-5° C. $^1$H NMR δ 8.553 (1H, s, C1-H), 5.805 (1H, s, C12-H), 3.716 (3H, s, OMe), 2.706 (1H, s, C9-H), 1.454, 1.393, 1.223, 1.194, 1.168, 1.161, 0.834 (all 3H, s, CMe). Anal $C_{32}H_{43}NO_4$ (C, H, N).

(b) Methyl 2-cyano-3,11-dioxo-18α-oleana-1,12-dien-30-oate

In a like manner, methyl 2-cyano-3,11-dioxo-18α-oleana-1,12-dien-30-oate was prepared from methyl 18α-glycyrrhetinate

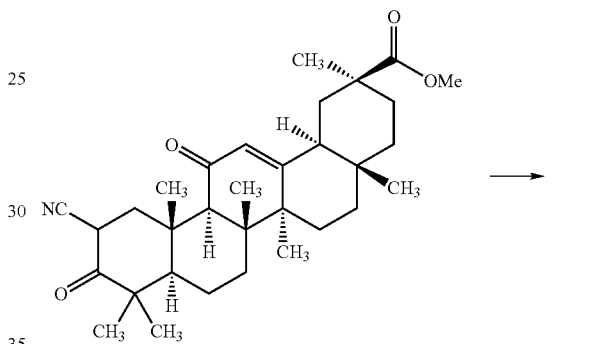

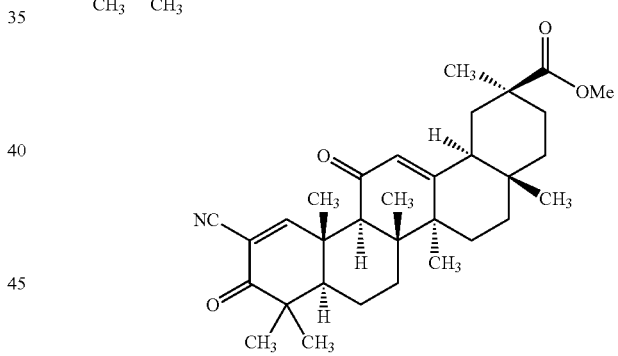

Example 5

Methyl 2-iodo-3,11-dioxo-18β-oleana-1,12-diene-30-oate

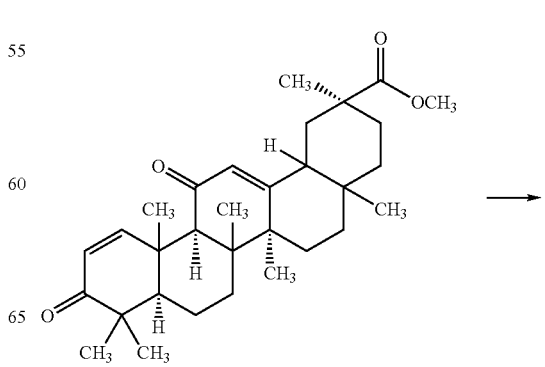

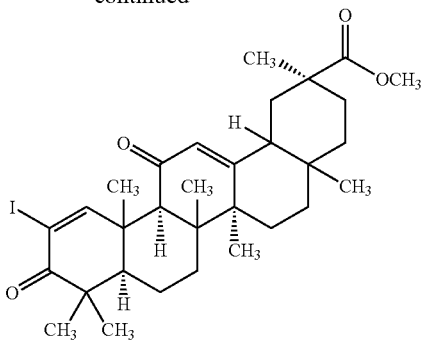

A mixture of methyl 3,11-dioxo-18β-oleana-1,12-diene-30-oate (437.6 mg, 0.9104 mmol), iodine (462.2 mg, 1.821 mmol) and pyridine (216 mg, 2.73 mmol) in tetrahydrofuran (10 mL) was stirred and heated at reflux for 5 h. The solvent was then removed in vacuo and the resulting dark gum dissolved in $CH_2Cl_2$ (25 mL). This solution was washed, successively, with aqueous sodium hydroxide (2 g in 20 mL), water (10 mL), hydrochloric acid (7.5 mL conc. HCl, 12.5 mL water), water (10 mL) and brine (20 mL). The solution was then dried over sodium sulfate. An analytical TLC of this solution ($MeOH/CH_2Cl_2$, 1:49) showed one major spot and a minor, more polar, spot corresponding to substrate. The solution was evaporated in vacuo to give an amber residue (607.7 mg) which was dissolved in $CH_2Cl_2$ and subjected to column chromatography ($SiO_2$, 32-63 mm, 20 g). Traces of residual iodine were washed off with $CH_2Cl_2$ and the product (534.0 mg) was recovered by washing with $MeOH/CH_2Cl_2$ (3:47). Crystallization of this white solid from hexane afforded colorless needles (512.9 mg, 92.9%) of the title compound. $^1H$ NMR δ 8.538 (1H, s, C1-H), 5.782 (1H, s, C12-H), 3.711 (3H, s, OMe), 2.722 (1H, s, C9-H), 1.454, 1.429, 1.400, 1.249, 1.167, 0.828 (all 3H, s, CMe), 1.172 (6H, s, 2×CMe).

Example 6

Preparation of methyl 3,11-dioxo-2-trifluoromethyl-18β-oleanana-1,2-diene-30-oate

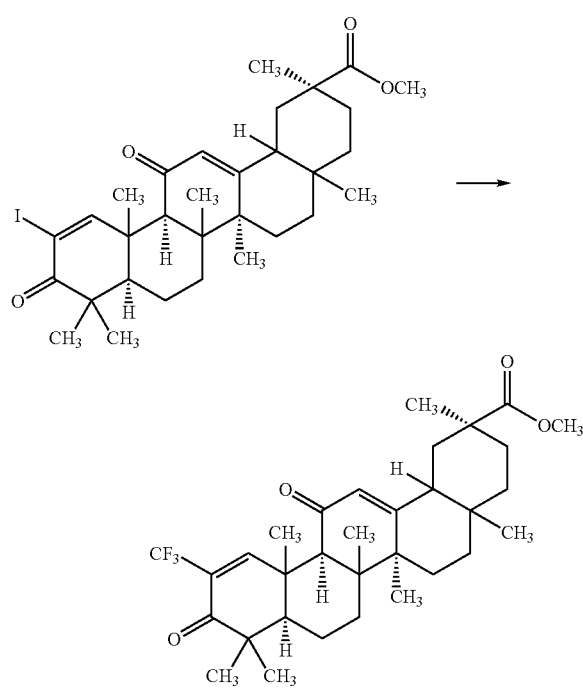

Dimethyl formamide (ca 15 mL; dried by stirring over $CaH_2$ overnight under $N_2$) was vacuum-transferred into a dry Schlenk tube containing methyl 3,11-dioxo-2-iodo-18β-oleanana-1,2-dien-30-oate (Example 5, 216.8 mg, 0.3574 mmol) and cuprous iodide (166.6 mg, 0.8744 mmol). This mixture was allowed to warm up to ambient temperature under vacuum and then $N_2$ was admitted. The resulting solution, containing some suspended solid, was heated to 70° C. with stirring under $N_2$, and methyl fluorosulfonyldifluoroacetate (0.66 mL, 1.0 g, 5.2 mmol) and then hexamethylphosphoramide (1.0 mL) were added by syringe. Stirring of the resulting somewhat cloudy solution, was continued, with heating, under $N_2$ for 20 h.

The reaction solution containing a fine suspension of a rust-coloured solid, was allowed to cool and then a saturated aqueous ammonium chloride solution (30 mL) was added. The resulting solution was extracted with diethyl ether three times (30, 15, and 15 mL); the rust-coloured solid adhered to the walls of the separating funnel. The combined ether extracts were dried over anhydrous sodium sulphate.

Evaporation of the dried extracts in vacuo left a colourless oily solid which was subjected to preparative TLC (Merck silica, eluant $MeOH/CH_2Cl_2$, 1:99). The resulting plates showed one major band along with a minor very polar one. The main band was recovered and eluted with $MeOH/CH_2Cl_2$ (1:19). Evaporation of the solvent in vacuo left a colorless, crystalline solid (172.0 mg) which was crystallized from hexane to give clear stout needles (150.4 mg) of methyl 3,11-dioxo-2-trifluoromethyl-18β-oleanana-1,2-diene-30-oate: mp 221-223° C. (with sublimation from 208° C.). $^1H$ NMR spectrum, δ 8.212 (1H, s, C-1H), 5.809 (1H, s, C-12H), 3.709 (3H, s, OMe), 2.721 (1H, s, C-9H), 1.429, 1.410, 1.199, 1.184, 1.171, 1.164 and 0.837 (all 3H, s, CMe).

Example 7

Effects of Compounds of the Invention on Colon Cancer Cell Lines Cell Lines

Human colon carcinoma cell lines SW480 and HT29 were provided by Dr. Stan Hamilton, M.D. Anderson Cancer Center (Houston, Tex.); SW-480 and HT-29 cells were maintained in Dulbecco's modified Eagle's medium nutrient mixture with Ham's F-12 (DMEM/Ham's F-12; Sigma-Aldrich, St. Louis, Mo.) with phenol red supplemented with 0.22% sodium bicarbonate, 0.011% sodium pyruvate, and 5% fetal bovine serum and 10 ml/l 100× antibiotic antimycotic solution (Sigma-Aldrich). Cells were maintained at 37° C. in the presence of 5% $CO_2$.

Antibodies and Reagents

Antibodies for poly(ADP-ribose) polymerase, cyclin D1, p27, p21, caveolin 1, KLF4 and Grp78 were purchased from Santa Cruz Biotechnology, Inc. (Santa Cruz, Calif.). NAG-1 was from Upstate Biotechnology (Charlottesville, Va.). Monoclonal β-actin antibody was purchased from Sigma-Aldrich. Reporter lysis buffer and luciferase reagent for luciferase studies were supplied by Promega (Madison, Wis.). 13-Galactosidase (β-Gal) reagent was obtained from Tropix (Bedford, Mass.), and LipofectAMINE reagent was purchased from Invitrogen (Carlsbad, Calif.). Western Lightning chemiluminescence reagent was from PerkinElmer Life and Analytical Sciences (Boston, Mass.). The PPARγ antagonists 2-chloro-5-nitro-N-phenylbenzamide (GW9662) and N-(4'-aminopyridyl)-2-chloro-5-nitrobenzamide (T007) were synthesized using the method described in Chem. Biol. 1997, 4(12):909-918, and their identities and purity (>98%) were confirmed by gas chromatography-mass spectrometry.

Plasmids

The Gal4 reporter containing 5× Gal4 response elements (pGal4) was kindly provided by Dr. Marty Mayo (University of North Carolina, Chapel Hill, N.C.). Gal4 DBD-PPARγ construct (gPPARγ) was a gift of Dr. Jennifer L. Oberfield (GlaxoSmithKline Research and Development, Research Triangle Park, N.C.). PPRE$_3$-luc construct contains three tandem PPREs with a minimal TATA sequence in pGL2.

Transfection and Luciferase Assay

Colon Cancer cell lines SW480 and HT29 (1×10$^5$ cells/well) were plated in 12-well plates in DMEM/Ham's F-12 media supplemented with 2.5% charcoal-stripped FBS. After 16 h, various amounts of DNA [i.e., Gal4Luc (0.4 µg), β-Gal (0.04 µg), Gal4PPAR and PPRE$_3$-Luc (0.04 µg)] were transfected using LipofectAMINE™ reagent (Invitrogen) following the manufacturer's protocol. Five hours after transfection, the transfection mix was replaced with complete media containing either vehicle (DMSO) or the indicated ligand for 20 to 22 h. Cells were then lysed with 100 µl of 1× reporter lysis buffer, and 30 µl of cell extract was used for luciferase and β-Gal assays. A LumiCount™ luminometer (PerkinElmer Life and Analytical Sciences) was used to quantitate luciferase and β-Gal activities, and the luciferase activities were normalized to β-Gal activity. Results are expressed as means±S.E. for at least three replicate determinations for each treatment group Mammalian Two-Hybrid Assay SW480 and HT29 cell lines were plated in 12-well plates at 1×10$^5$ cells/well in DMEM/F-12 media supplemented with 2.5% charcoal-stripped fetal bovine serum. After growth for 16 h, various amounts of DNA, i.e. Gal4Luc (0.4 µg), β-gal (0.04 µg), VP-PPARγ (0.04 µg), pMSRC1 (0.04 µg), pMSRC2 (0.04 µg), pMSRC3 (0.04 µg), pMPGC-1 (0.04 µg), pMDRIP205 (0.04 µg), and pMCARM-1 (0.04 µg) were transfected by LipofectAMINE (Invitrogen) according to the manufacturer's protocol. After 5 h of transfection, the transfection mix was replaced with complete media containing either vehicle (DMSO) or the indicated ligand for 20-22 h. Cells were then lysed with 100 ml of 1× reporter lysis buffer, and 30 µl of cell extract was used for luciferase and β-galactosidase assays. Lumicount was used to quantitate luciferase and β-galactosidase activities, and the luciferase activities were normalized to β-galactosidase activity.

Cell Proliferation Assay

SW480 and HT 29 Cells (2×10$^4$) were plated in 12-well plates, and media were replaced the next day with DMEM/Ham's F-12 media containing 2.5% charcoal-stripped FBS and either vehicle (DMSO) or the indicated ligand and dissolved in DMSO. Fresh media and compounds were added every 48 h. Cells were counted at the indicated times using a Coulter Z1 cell counter. Each experiment was done in triplicate, and results are expressed as means±S.E. for each determination Western Blot Analysis SW-480 and HT-29 (3×10$^5$) cells were seeded in six-well plates in DMEM/Ham's F-12 media containing 2.5% charcoal-stripped FBS for 24 h and then treated with either the vehicle (DMSO) or the indicated compounds. Whole-cell lysates were obtained using high-salt buffer [50 mM HEPES, 500 mM NaCl, 1.5 mM MgCl$_2$, 1 mM EGTA, 10% glycerol, and 1% Triton X-100, pH 7.5, and 5 µl/ml Protease Inhibitor Cocktail (Sigma-Aldrich)]. Protein samples were incubated at 100° C. for 2 min, separated on 10% SDS-PAGE at 120 V for 3 to 4 h in 1× running buffer (25 mM Tris-base, 192 mM glycine, and 0.1% SDS, pH 8.3), and transferred to polyvinylidene difluoride membrane (PVDF; Bio-Rad, Hercules, Calif.) at 0.1 V for 16 h at 4° C. in 1× transfer buffer (48 mM Tris-HCl, 39 mM glycine, and 0.025% SDS). The PVDF membrane was blocked in 5% TBST-Blotto (10 mM Tris-HCl, 150 mM NaCl, pH 8.0, 0.05% Triton X-100, and 5% nonfat dry milk) with gentle shaking for 30 min and was incubated in fresh 5% TBST-Blotto with 1:1000 (for caveolin-1, p27, p21, cyclin D1, Grp78), 1:500 (for KLF4, NAG-1), 1:250 (for PARP), and 1:5000 (for β-actin) primary antibody overnight with gentle shaking at 4° C. After washing with TBST for 10 min, the PVDF membrane was incubated with secondary antibody (1:5000) in 5% TBST-Blotto for 90 min. The membrane was washed with TBST for 10 min, incubated with 10 ml of chemiluminescence substrate (PerkinElmer) for 1.0 min, and exposed to Kodak X-OMAT AR autoradiography film (Eastman Kodak, Rochester, N.Y.).

Results

Figure 2:
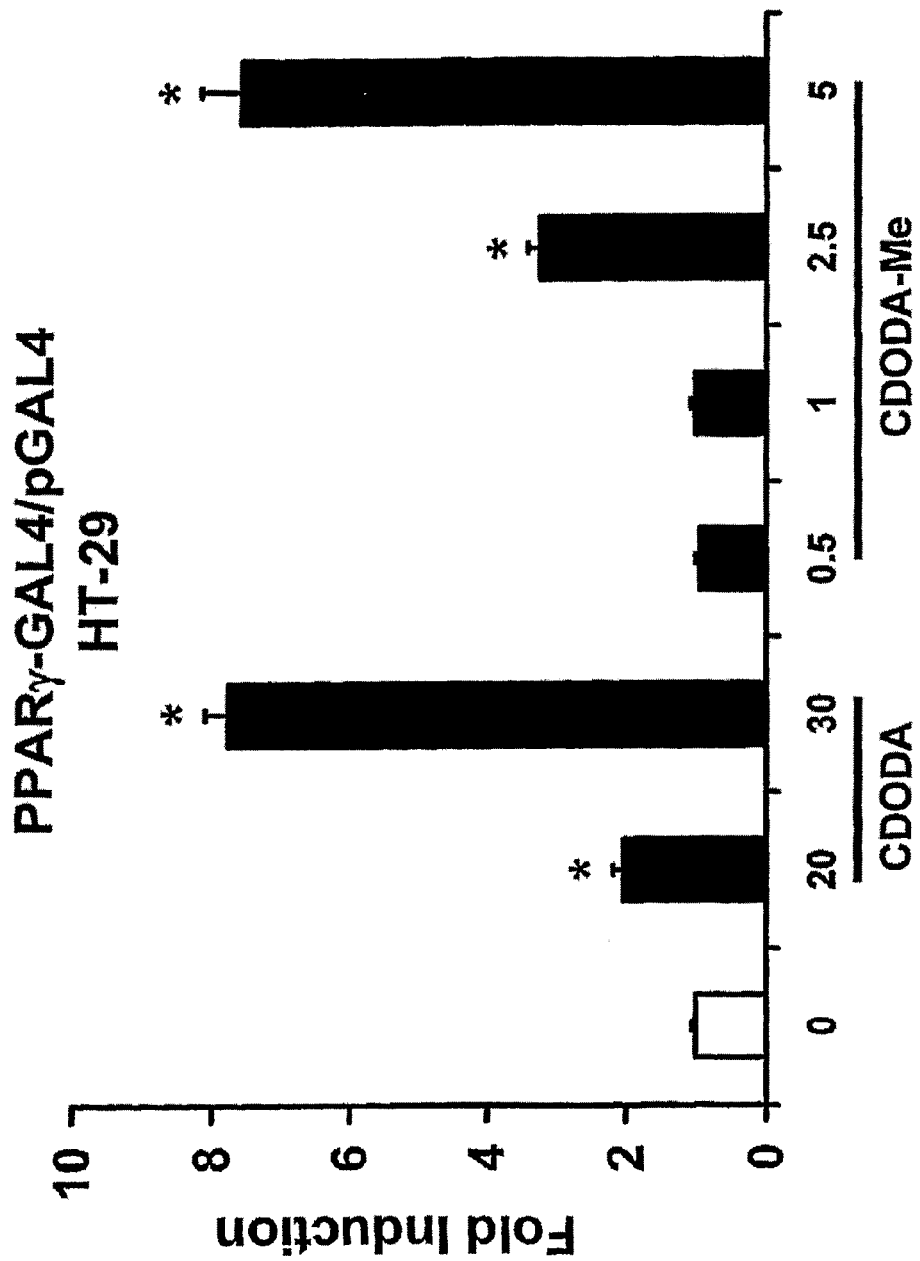
FIG. 2 shows ligand-dependent activation of PPARγ-GAL4/pGAL4 in HT-29 cells. Cells were transfected with PPARγ-GAL4/pGAL4, treated with different concentrations of the triterpenoids, and luciferase activity was determined as described in the Examples. Results of all transactivation studies in this Figure are presented as means±SE for at least 3 separate determinations for each treatment group and significant ($p<0.05$) induction compared to solvent (DMSO) control is indicated by an asterisk.
Figure 3:
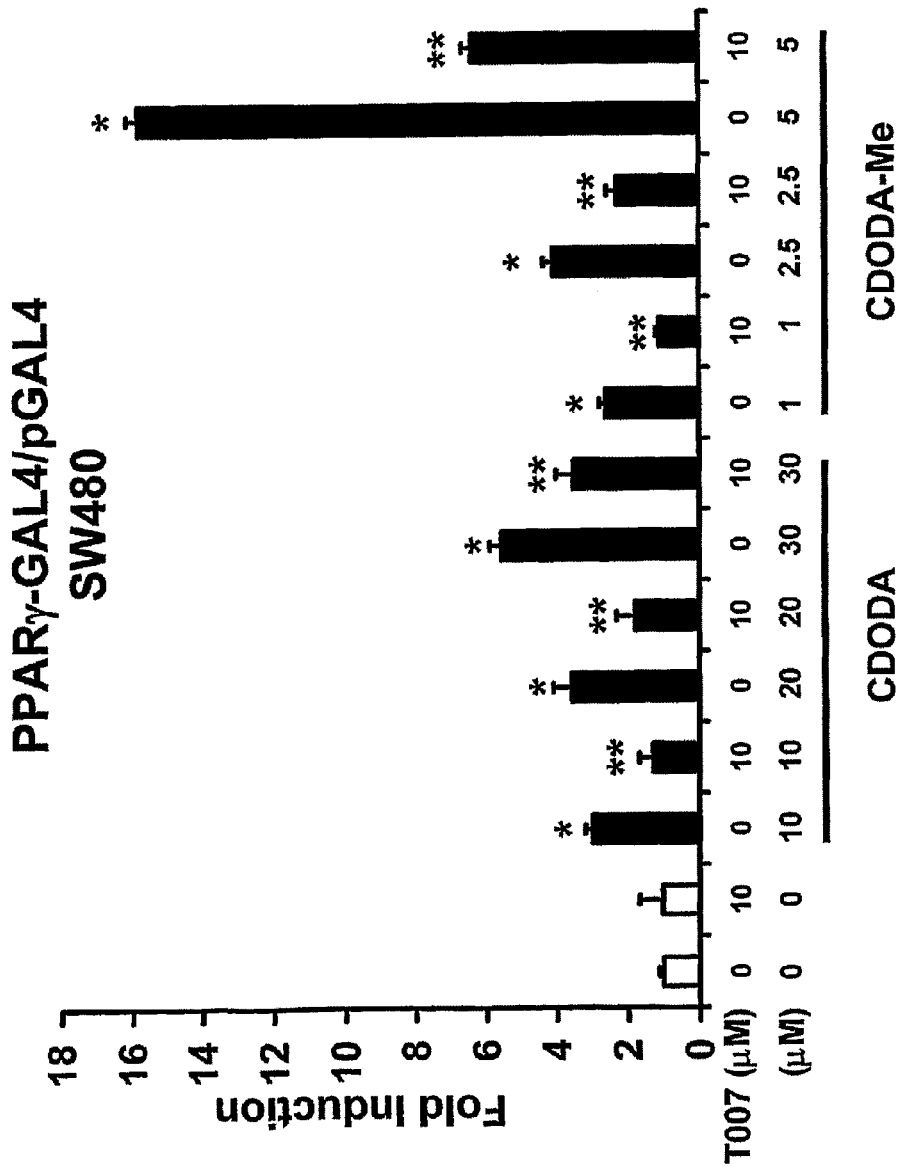
FIG. 3 shows inhibition of transactivation in SW480 cells transfected with PPARγ-GAL4/pGAL4 by PPARγ antagonists. Cells were transfected with PPARγ-GAL4/pGAL4, treated with different concentrations of CDODA or CDODA-Me alone or in combination with 10 μM T007, and luciferase activities were determined as described in FIG. 1. Significant ($p<0.05$) inhibition of induced transactivation by T007 is indicated (**).
Figure 4:
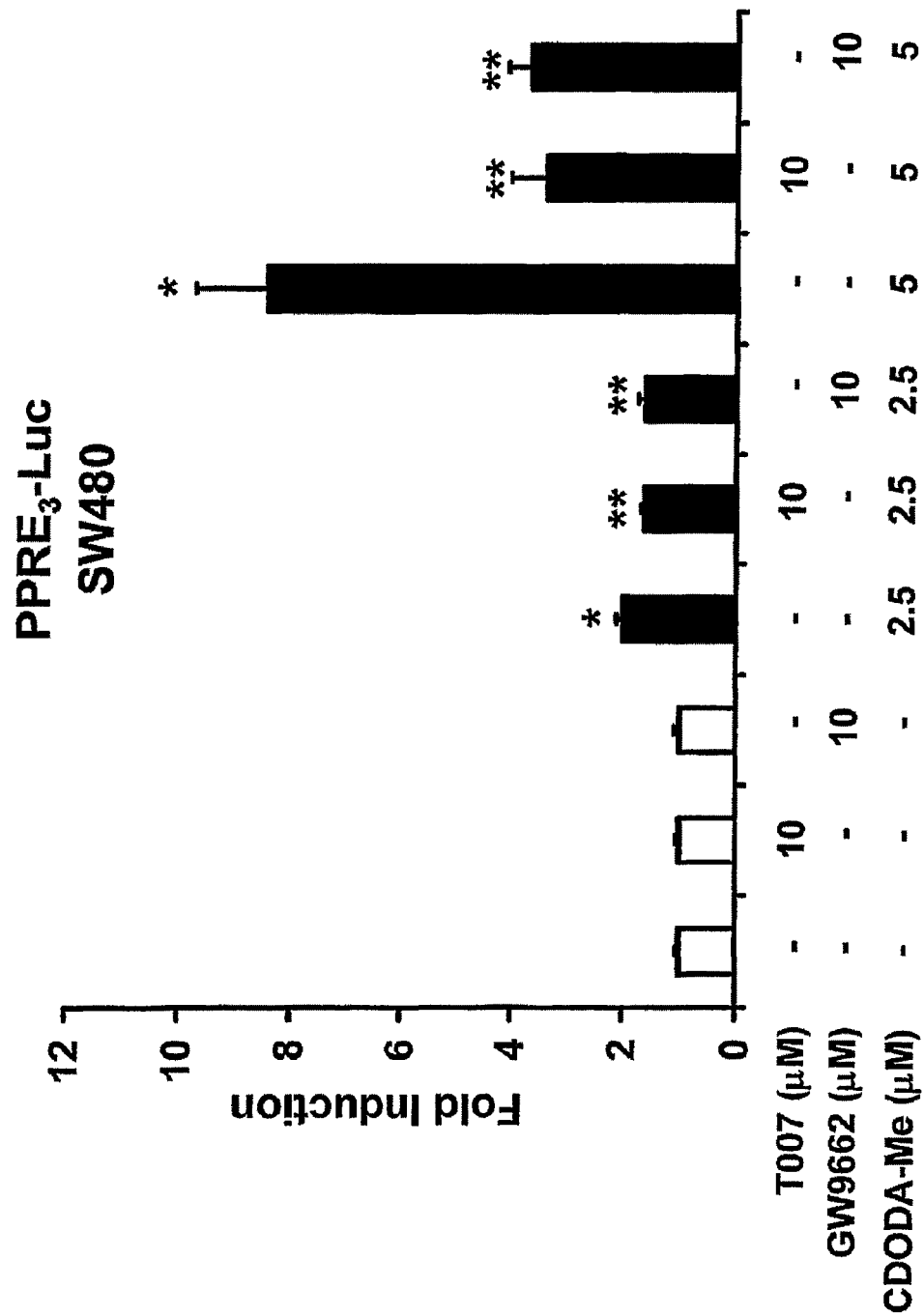
FIG. 4 shows inhibition of transactivation in SW480 cells transfected with PPRE$_3$-Luc by PPARγ antagonists. Cells were transfected with PPRE$_3$-Luc, treated with different concentrations of CDODA-Me alone or in combination with 10 μM GW9662 and/or T007, and luciferase activities were determined as described in FIG. 1. Significant ($p<0.05$) inhibition of induced transactivation by T007 or GW9662 is indicated (**).
Figure 5:
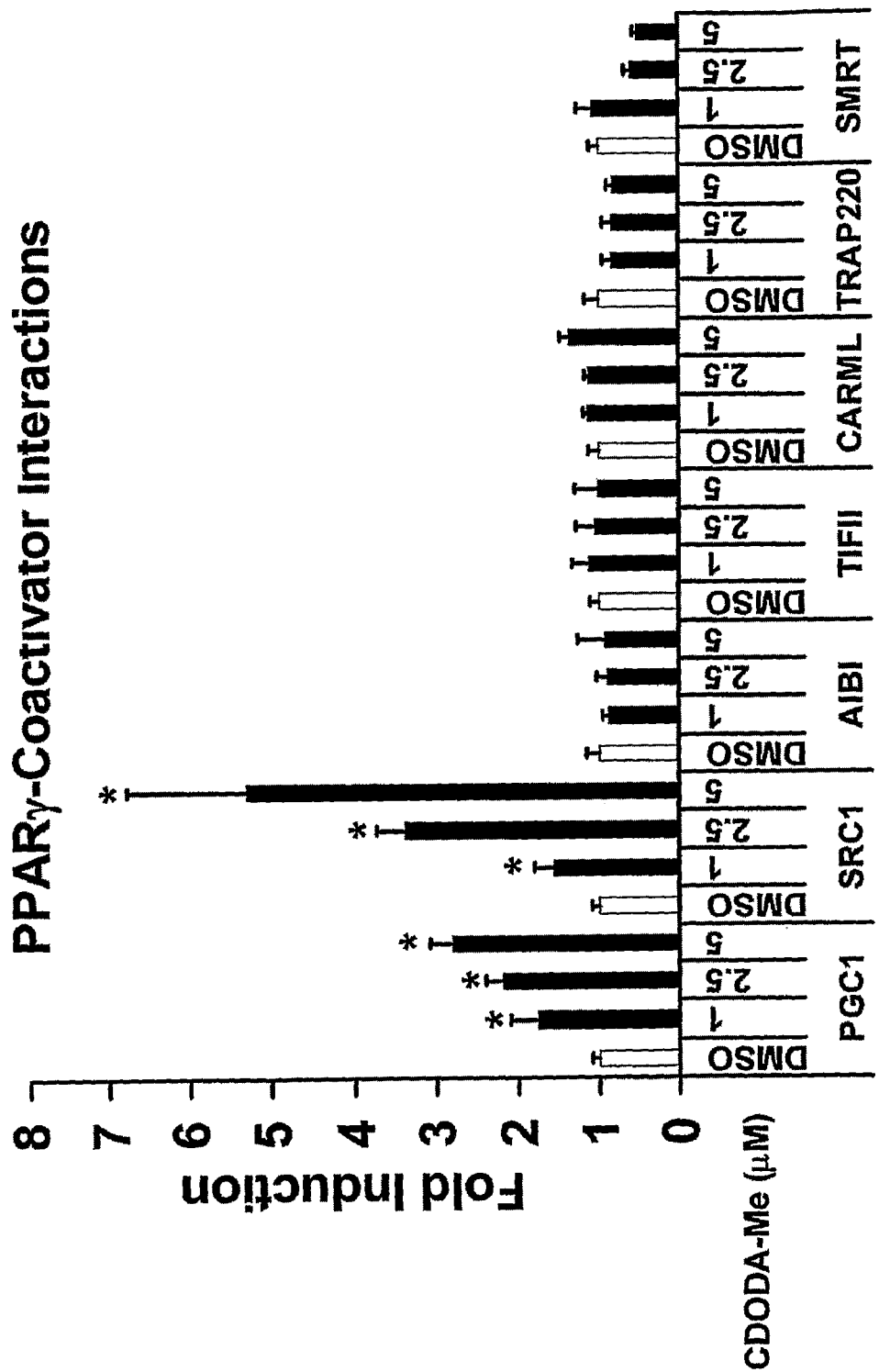
FIG. 5 shows ligand-induced PPARγ-coactivator interactions. SW480 cells were transfected with VP-PPARγ, coactivator-GAL4/pGAL4, treated with different concentrations of CDODA-Me, and luciferase activity was determined as described in the Examples. Results are expressed as means±SE for 3 replicate determinations for each treatment group, and significant ($p<0.05$) induction is indicated by an asterisk.

The growth inhibitory effects of β-DODA (Example 1(a)), β-CDODA (Example 3(a)) and their corresponding methyl ester derivatives (Examples 2(a) and 4(a)) were investigated in both HT-29 and SW480 colon cancer cell lines. The IC$_{50}$ values for β-DODA and β-DODA-Me were 25 and 10 µM respectively in SW480 cells and in HT-29 cells, IC$_{50}$ values were similar (20-30 and 5-10 µM) respectively). The 2-cyano substituted analogs were more potent inhibitors of SW480 cell proliferation with IC$_{50}$ values of 2.5-5.0 and 0.2 and 0.5 µM for β-CDODA and β-CDODA-Me respectively. The corresponding IC$_{50}$ values for β-CDODA and β-CDODA-Me in HT-29 cells were 1.0 and 0.2 to 0.5 µM respectively indicating that this cell line was more sensitive than SW480 cells to the growth inhibitory effects of β-CDODA. Previous studies showed that both CDDO and CDDO-Me induced luciferase activity in SW480 cells transfected with GAL4-PPARγ/GAL4-Luc (22) and the results in FIG. 1 summarize the activation of PPARγ by the GA derivatives of the present invention. β-CDODA-Me (1-5 µM) significantly activated PPARγ with a maximal 18-Fold induction of luciferase activity, whereas 20-30 µM β-CDODA induced a <4.5 fold increase in activity and up to 30 µM β-DODA and β-DODA-Me did not enhance transactivation. The fold inducibility of this PPARγ-dependent assay is lower in HT-29 cells however, results in FIG. 2 show that, like CDDO-Me (22), β-CDODA-Me and β-CDODA induced transactivation in this cell line transfected with GAL4-PPARγ/GAL4-Luc whereas the β-DODA and β-DODA-Me exhibited minimal activity. Using a similar transactivation system in the more responsive SW480 cells, the induction of luciferase activity by 1.0, 2.5 and 5.0 β-CDODA-Me and 10, 20 and 30 µM β-CDODA was inhibited after cotreatment with the PPARγ antagonist T007 (FIG. 3). It was also shown that both β-CDODA-Me and β-CDODA induced transactivation in SW480 cells transfected with PPRE$_3$-Luc and these responses were inhibited after cotreatment with the PPARγ antagonists T007 and GW9662 (FIG. 4). These results demonstrate that both β-CDODA and β-CDODA-Me but not DODA or DODA-Me activate PPARγ and this illustrates the beneficial effect of the 2-substituent (for example a 2-cyano substituent) for both the growth inhibition and PPARγ-dependent activities in these synthetic triterpenes. The effects of β-CDODA-Me on interactions between PPARγ and several coactivators/corepressors in a mammalian two-hybrid assay in SW480 cells transfected with GAL4-coactivator and VP-PPARγ (ligand binding domain) chimeras were also investigated. The results (FIG. 5) show that β-CDODA-Me induced transactivation only in cells transfected with GAL4-chimeras containing coactivators PGC-1 and SRC-1 whereas ligand-induced interactions of SRC-2, SRC-3, CARM1, TRAP220 and SMRT with PPARγ were not observed. These results clearly distinguish β-CDODA-Me from CDDO-Me since the latter compound induced interactions between VP-PPARγ and GAL4-coactivator/corepressor chimeras containing SRC1, SRC2, SRC3, PGC1, TRAP220, CARM1 and SMRT in the same cell line (22).

Figure 6:
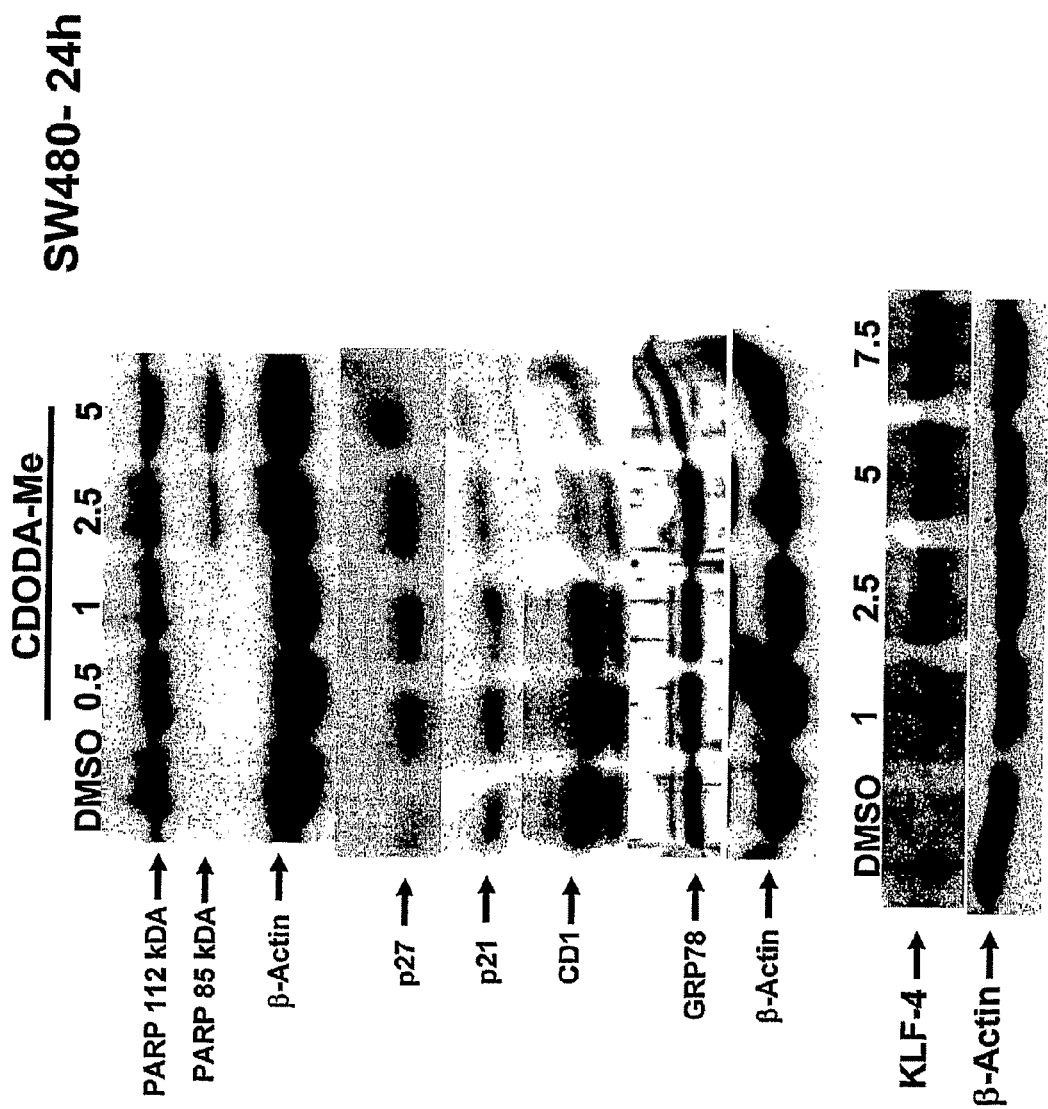
FIG. 6 shows the effects of CDODA-Me on cell cycle proteins, apoptosis and tumor suppressor genes. SW480 cells were treated with different concentrations of CDODA-Me for 24 hr and various proteins were analyzed by western immunoblot analysis as described in the Examples. (β-actin served as a loading control and results were observed in replicate (2 or more) experiments.
Figure 7:
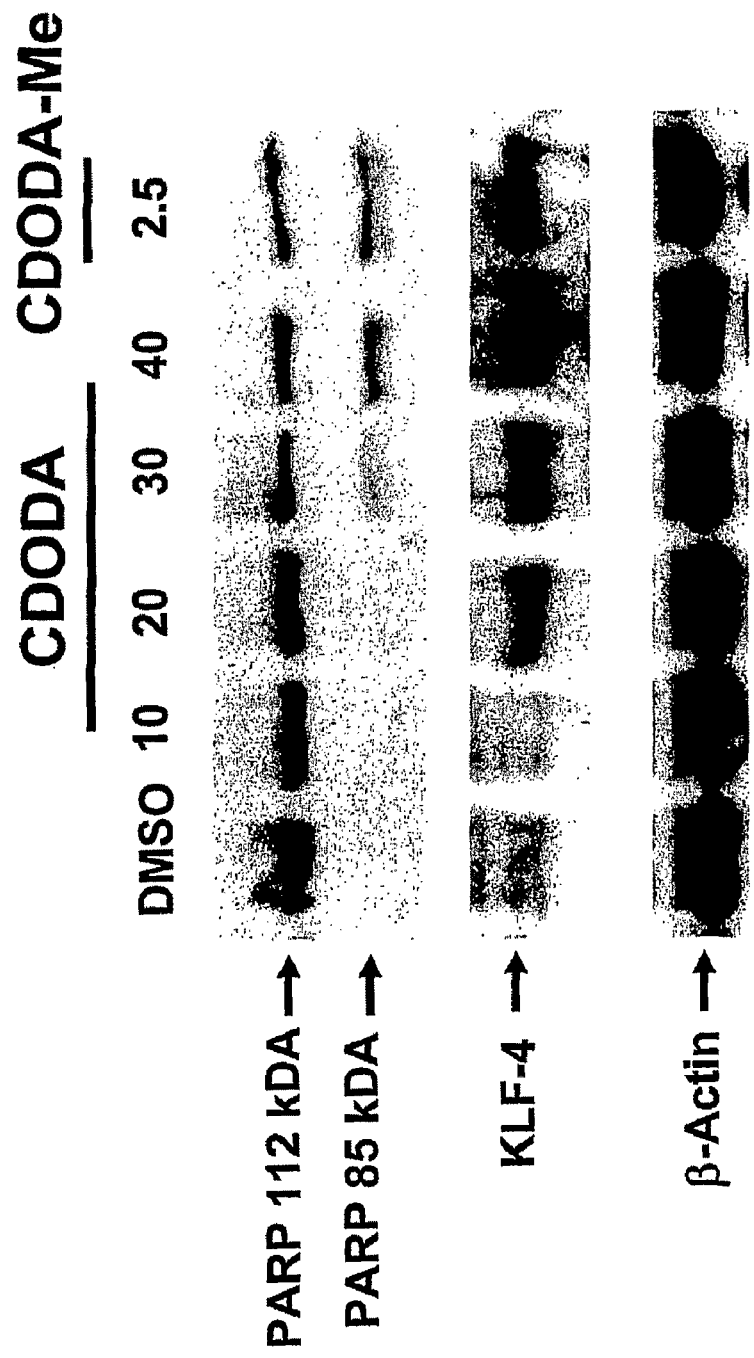
FIG. 7 shows the effects of CDODA-Me and CDODA on cell cycle proteins, apoptosis and tumor suppressor genes. SW480 cells were treated with different concentrations of CDODA-Me or CDODA for 24 and various proteins were analyzed by western immunoblot analysis as described in the Examples. β-actin served as a loading control and results were observed in replicate (2 or more) experiments.

The effects of β-CDODA-Me on various proteins associated with cell proliferation and apoptosis were also investigated in SW480 cells over a range of concentrations from 0.5-5.0 μM (FIG. 6). The pattern of protein expression was concentration-dependent as previously reported for CDDO-Me where PARP cleavage, an indicator of apoptosis, was only observed at higher concentrations (2.5 and 5.0 μM) and this was similar to the overall effects of β-CDODA-Me on SW480 cell proliferation. Cyclin D1 and p21 protein expression were unchanged after treatment with 0.5 or 1 μM β-CDODA-Me whereas expression of both proteins was decreased at the higher (2.5 and 5.0 μM) doses. In contrast, there was a dose-dependent increase of p27 protein over full range of concentrations whereas induction of GRP78 protein, an indicator of ER stress, was not observed. NAG-1, a tumor suppressor gene induced by some PPARγ agonist in colon cancer cells (23, 28-30) was not induced by β-CDODA-Me in SW480 cells. In addition the induction of the tumor suppressor gene KLF4 by 0.5-7.5 μM β-CDODA-Me was observed (FIG. 6). In a separate experiment at higher doses of β-CDODA (10-40 μM), PARP cleavage and induction of KLF4, which is only induced at concentrations greater than 10-20 μM, was observed (FIG. 7). Thus both β-CDODA and β-CDODA-Me induce KLF4 however the latter compound was clearly the more potent analog and was used in subsequent studies as the prototype for this class of PPARγ-active triterpenoids.

Figure 8:
FIG. 8 compares the effects of CDODA-Me and CDDO-Me on cell cycle proteins, apoptosis and tumor suppressor genes. SW480 cells were treated with different concentrations of CDODA-Me or CDDO-Me for 96 hr and various proteins were analyzed by western immunoblot analysis as described in the Examples. β-actin served as a loading control and results were observed in replicate (2 or more) experiments.

Previous studies showed that CDDO-Me and related compounds and other PPARγ agonists induced caveolin-1 in HT-29 and SW480 colon cancer cells (22). Caveolin-1 acts as a tumor suppressor gene in colon cancer cells and inhibits cell/tumor (in vivo) growth (76, 77). Caveolin-1 is only induced in colon cancer cells after prolonged treatment with PPARγ agonists and the results in FIG. 8 show that although both CDDO/CDDO-Me induce caveolin-1 protein after treatment for 3 days, β-CDODA-Me did not affect expression of caveolin-1 in SW480 cells. This was observed over several replicate experiments and clearly distinguished β-CDODA-Me from CDDO/CDDO-Me in SW480 cells.

Figure 9:
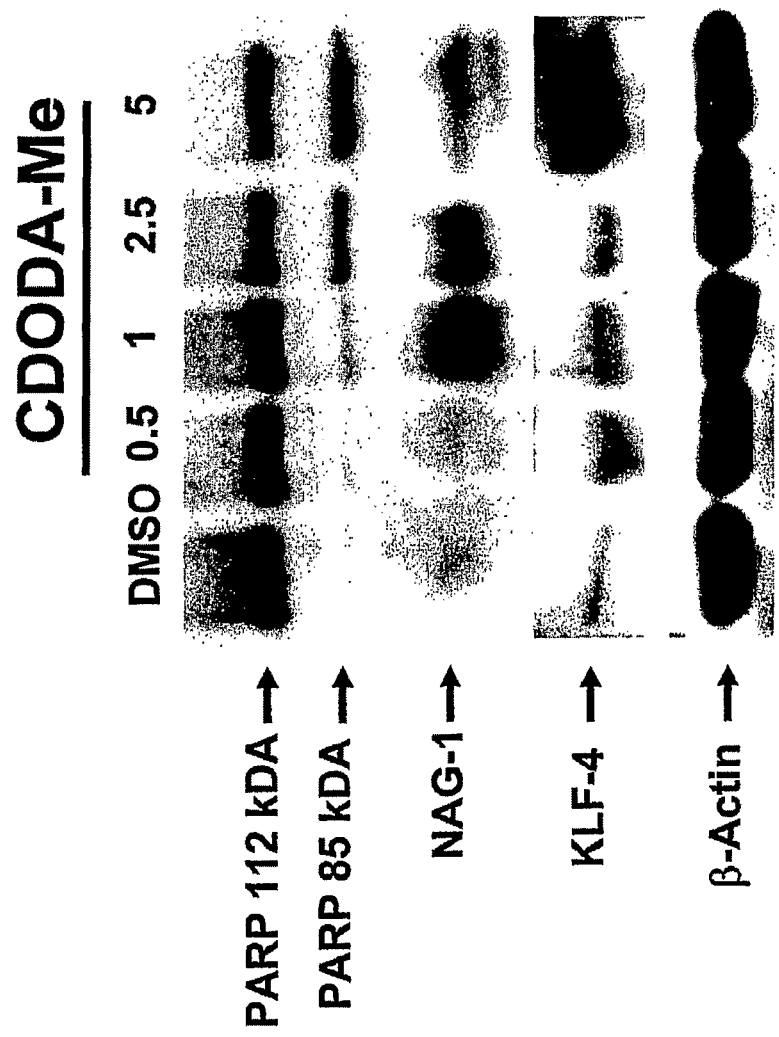
FIG. 9 shows the effects of CDODA-Me on cell cycle proteins, apoptosis and tumor suppressor genes. Treatment of HT-29 cells for 24 hr. Cells were treated and analyzed as described above (FIGS. 6-8) for PARP (112 kDa), PARP (85 kDa), NAG-1 and KLF-4. β-actin served as a loading control and results in were observed in replicate (2 or more) experiments.

The effects of β-CDODA-Me on apoptosis and induction of caveolin-1, NAG-1 and KLF4 was also investigated in HT-29 cells. The results (FIG. 9) show that after treatment with β-CDODA-Me for 24 hours there was induction of PARP cleavage which was accompanied by induction of NAG-1 and KLF4 proteins. It should be noted that induction of these tumor suppressor genes was concentration dependent and NAG-1 protein levels were decreased at higher (5 μM) concentrations. Moreover, treatment of HT-29 cells with β-CDODA-Me for 3 days also resulted in induction of caveolin-1. These results show that cell context was also an important factor in the activity of β-CDODA-Me where caveolin-1 was induced in HT-29 but not in SW480 colon cancer cells.

Figure 10:
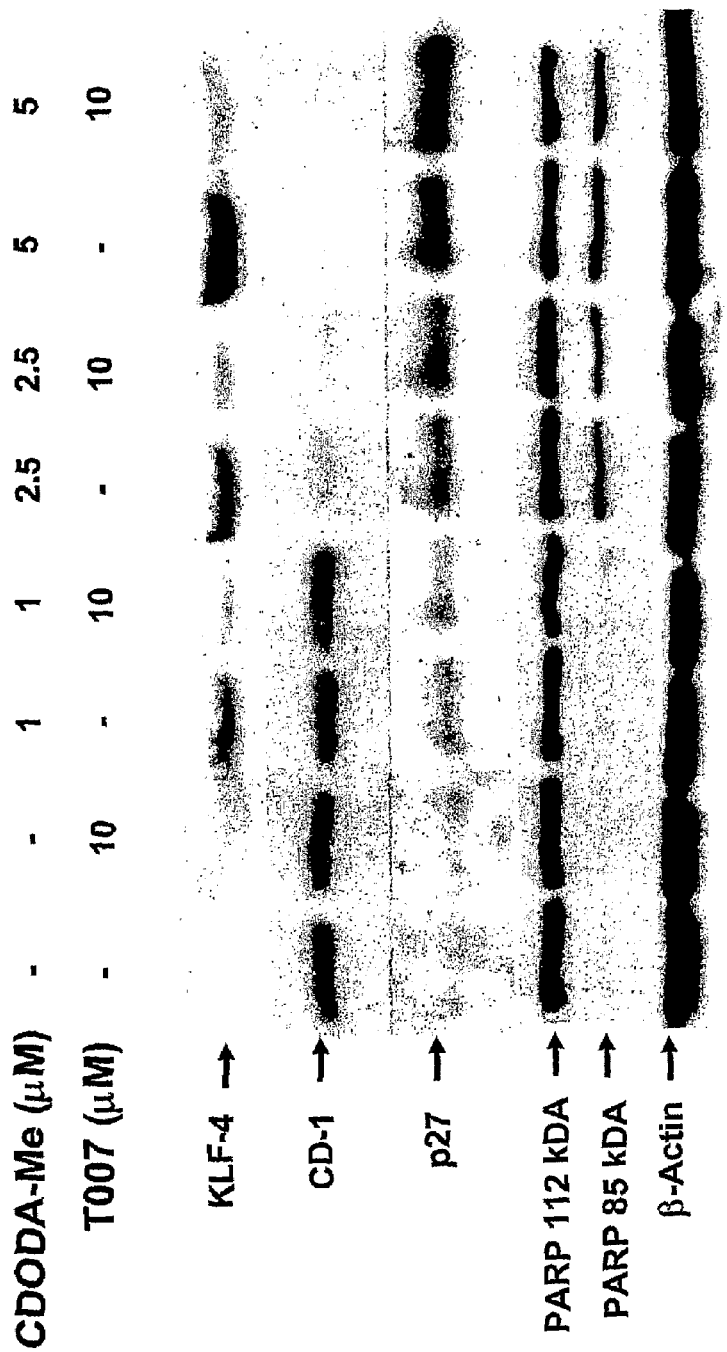
FIG. 10 shows the effects of PPARγ antagonists on CDODA-Me induced effects on protein expression or apoptosis. SW480 cells were treated for 24 hr with different concentrations of CDODA-Me alone or in combination with 10 μM T007 and PARP (112 kDa), PARP (85 kDa), CD-1, p27, NAG-1 and KLF-4 proteins were analyzed by western immunoblots as described in the Examples. β-actin served as a loading control and results were observed in replicate (2 or more) experiments.
Figure 11:
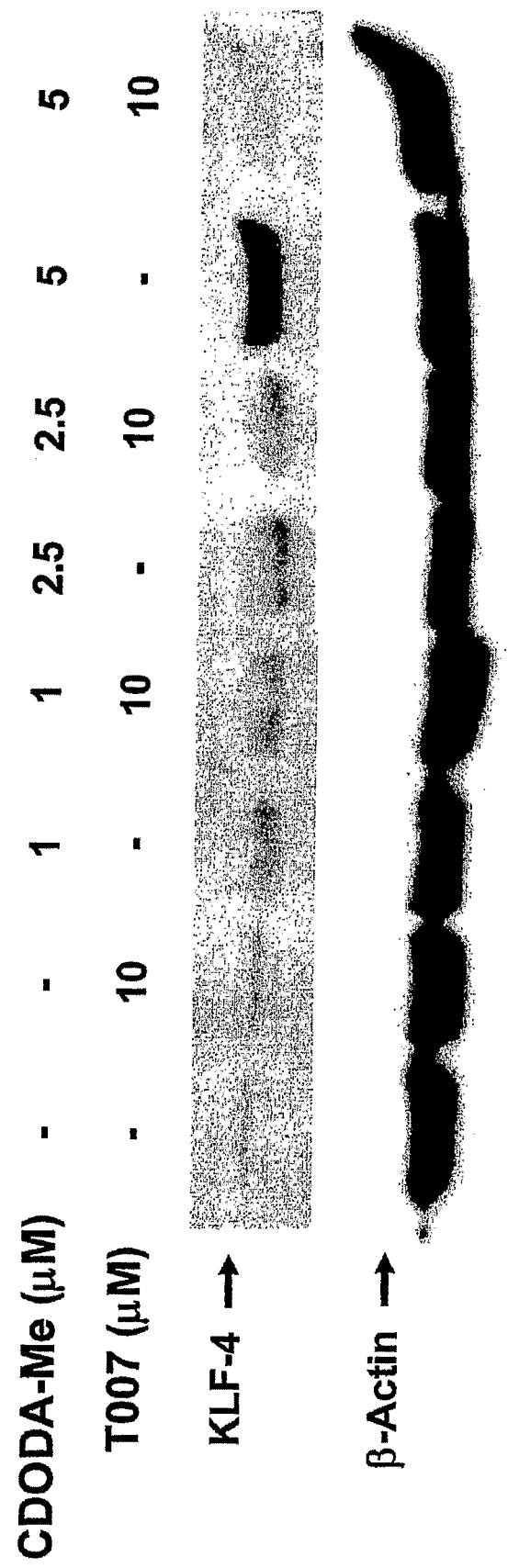
FIG. 11 shows the effects of PPARγ antagonists on CDODA-Me induced effects on protein expression or apoptosis. HT-29 cells were treated for 24 hr with different concentrations of CDODA-Me alone or in combination with 10 μM T007 and KLF-4 protein was analyzed by western immunoblots as described in the Examples. β-actin served as a loading control and results were observed in replicate (2 or more) experiments.
Figure 12:
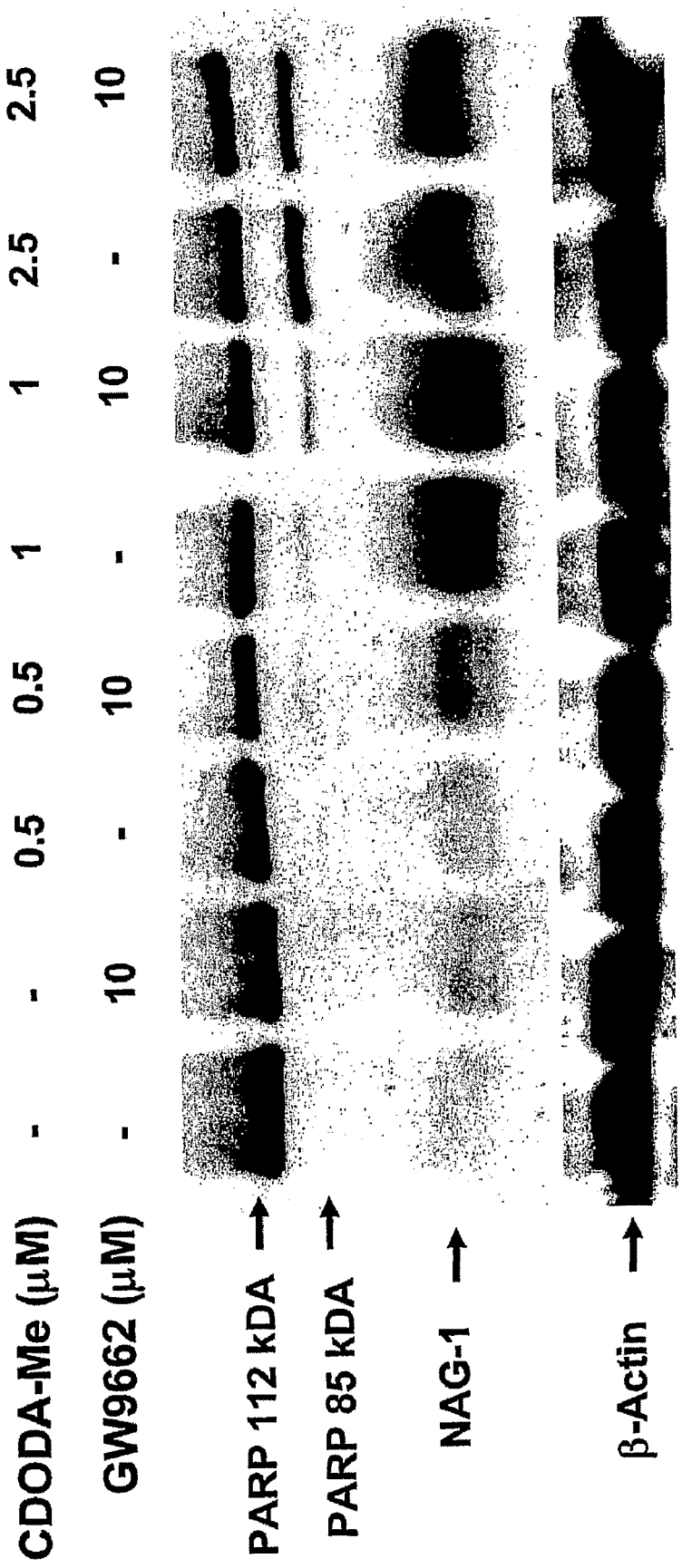
FIG. 12 shows the effects of PPARγ antagonists on CDODA-Me induced effects on protein expression or apoptosis. HT-29 cells were treat for 24 hr with different concentrations of CDODA-Me alone or in combination with 10 μM GW9662 and PARP (112 kDa), PARP (85 kDa) and NAG-1 proteins were analyzed by western immunoblots as described in the Examples. β-actin served as a loading control and results were observed in replicate (2 or more) experiments.
Figure 13:
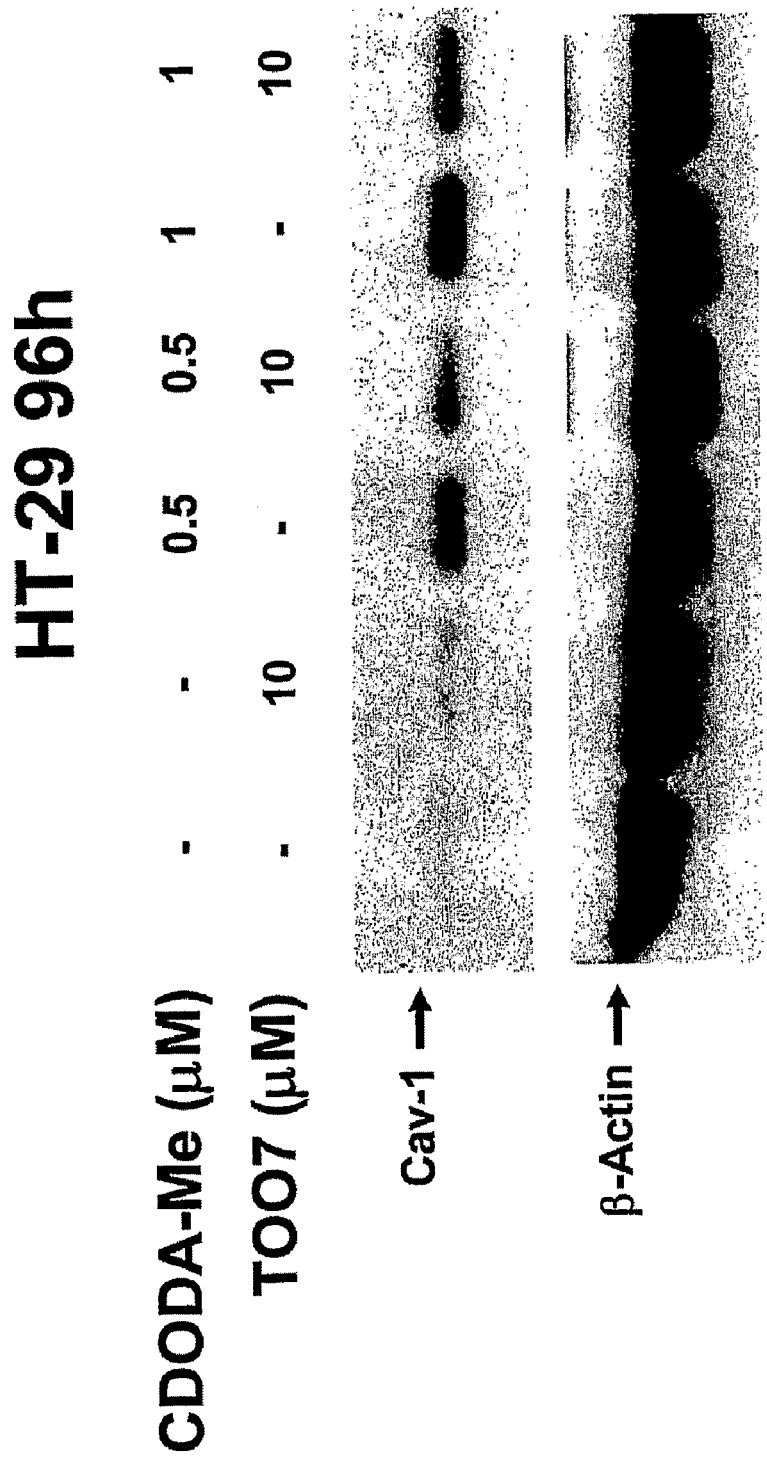
FIG. 13 shows the effects of PPARγ antagonists on CDODA-Me induced effects on protein expression or apoptosis. HT-29 cells were treated for 96 hr with different concentrations of CDODA-Me alone or in combination with 10 μM T007 and Cav-1 protein was analyzed by western immunoblots as described in the Examples. β-actin served as a loading control and results were observed in replicate (2 or more) experiments.

KLF4 is induced by β-CDODA-Me in both SW480 and HT-29 cells and a recent study reported that the PPARγ agonist 15-deoxy-Δ12, 14-Prostaglandin J2 (PGJ2) also induced KLF4 in HT-29. However induction of KLF4 by PGJ2 was PPARγ-independent and involved activation of mitogen-activated protein kinase (MAPK) (22). Results in FIGS. 10 and 11 show that treatment with β-CDODA-Me induces KLF-4 protein in SW480 and HT-29 cells and cotreatment with the PPARγ antagonist T007 blocks this induction response in both cell lines. In contrast, T007 does not affect β-CDODA-Me induced down regulation of cyclin D1, p27 or PARP cleavage in SW480 cells (FIG. 10) and the PPARγ-independent induction of apoptosis in SW480 cells has previously been reported for CDDO-Me in the same cell line (22). Result in FIG. 12 show that induction of NAG-1 and PARP cleavage in HT-29 cells was not affected after cotreatment with T007 whereas the induction of caveolin-1 by β-CDODA-Me was inhibited after cotreatment with T007 (FIG. 13). These results demonstrate that β-CDODA-Me like CDDO/CDDO-Me induces both receptor-dependent and independent growth inhibitory/apoptotic effects in colon cancer cells (22), however, despite their structural similarities these compounds induce both different and overlapping responses that are cell context-dependent and this is characteristic of selective PPARγ modulators.

Discussion

PPARγ and other members of the nuclear receptor superfamily are characterized by their modular structure which contains several regions and domains that are required for critical receptor-protein and receptor-DNA interactions (78-79). Nuclear receptors typically contain N- and C-terminal activation functions (AF1 and AF2 respectively), a DNA binding domain and a flexible hinge region. The addition of receptor ligand usually results in formation of a transcriptionally active nuclear receptor complex which binds cognate response elements in promoter regions of target genes and activates transcription. However, receptor-mediated transactivation is dependent on several factors including cell context-specific expression of coregulatory proteins (eg. coactivators), gene promoter accessibility and ligand structure (80). The complex pharmacology of receptor ligands is due, in part to their structure-dependent conformational changes in the bound receptor complex which may differentially interact with coregulatory factors and exhibit tissue-specific agonist and/or antagonist activity (80, 81). This has led to development of selective receptor modulators (SRMs) for several nuclear receptors which can selectively activate or block specific receptor-mediated responses.

There is evidence that different structural classes of PPARγ agonists are also SRMs and induce tissue-specific receptor-dependent and independent responses. For example induction of NAG-1 in HCT116 colon cancer cells by PGJ2 was PPARγ-dependent whereas both troglitazone and PPARγ-active 1,1-bis(3'-indolyl)-1-(p-substituted phenyl)methanes (C-DIMs) also enhanced NAG-1 expression through receptor-independent pathways in the same cell line (22, 82, 83). Differences between PGJ2 and rosiglitazone have also been observed in mammalian two hybrid assays in COS-1 cells transfected with VP-PPARγ and GAL4-coactivator chimeras and in colon cancer cells rosiglitazone and PPARγ-active C-DIMs also induced a different pattern of receptor-coactivator interactions (84, 85). Previous studies have demonstrated that the synthetic triterpenoids CDDO and CDDO-Me are potent anticancer drugs in multiple cell lines and these compounds act through PPARγ-dependent and independent pathways (20-22, 86-88). Moreover in SW480 and other colon cancer cell lines the receptor-dependent (caveolin-1 induction) and receptor independent (apoptosis) responses induced by CDDO and CDDO-Me were concentration-dependent and were observed at low and high doses respectively. In the present disclosure, the activity of β-CDODA and β-CDODA-Me, two synthetic compounds derived from glycyrrhetinic acids is reported. Although CDDO/CDDO-Me and β-CDODA/β-CDODA-Me are isomers which possess a pentacyclic oleanolane backbone, there are significant structural differences between the two sets of compounds. In β-CDODA and β-CDODA-Me the carboxyl substituent is at C-20 instead of C-17 for CDDO/CDDO-Me, the stereochemistry of the E-D ring fusion at C-18 and the α,β-unsaturated ketone moieties in the C-ring are also different in the GA derivatives compared to CDDO. Initial studies showed that β-CDODA and β-CDODA-Me inhibited growth of SW480 and HT-29 colon cancer cells and it was apparent that the addition of a substituent at the 2 position (for example a 2-cyano group) enhanced their growth inhibitory effects compared to their des-cyano analogs β-DODA and β-DODA-Me and this was more pronounced for β-CDODA-Me compared to β-CDODA. Like CDDO/CDDO-Me, both β-CDODA and β-CDOODA-Me also activated PPARγ in transactivation assays and the magnitude of the induction response by β-CDODA-Me and CDDO-Me were similar. CDDO-Me was active at lower doses than β-CDODA-Me in both the growth inhibition and transactivation assays in SW480 cells. β-CDODA was less potent than either β-CDODA-Me or CDDO in these same assays and therefore was primarily used for further studies.

β-CDODA-Me decreased SW480 and HT-29 cell growth and induced PPARγ-independent PARP cleavage in both cell lines. β-CDODA-Me was less potent than CDDO-Me in SW480 cells (22) nevertheless, the newly synthesized GA derivative was a potent anticancer agent in colon cancer cells with effects on cell survival and apoptosis in the higher nM and lower μM range. β-CDODA-Me induced the tumor suppressor gene KLF4 in both SW480 and HT-29 cells and this response was PPARγ-dependent and inhibited by T007. These results clearly distinguish between β-CDODA-Me and PGJ2 which also induced KLF4 in HT29 cells through a receptor-independent pathway (89). Differences between β-CDODA-Me and CDDO-Me in were observed SW480 cells. CDDO-Me but not β-CDODA-Me induces caveolin-1 in SW480 cells (22) (FIG. 8) whereas both compounds induce caveolin-1 in HT-29 cells (22) (FIG. 13) and induction of caveolin-1 was inhibited by GW9662. Thus differences between β-CDODA-Me and CDDO-Me in activation of caveolin-1 protein expression were also dependent on cell context. These results are consistent with the structural differences between the two set of PPARγ agonists derived from oleanolic acid and GA and also correlated with their effects on VP-PPARγ-GAL4-coactivator interactions in a mammalian two hybrid assay (FIG. 5). β-CDODA-Me induces interactions of PPARγ only with SRC-1 and PGC-1 whereas CDDO-Me induces interactions with all the coactivators shown in FIG. 5 (22). Thus results of this study demonstrate that CDODA-Me represents a new class of selective PPARγ modulators that induces both PPARγ-dependent and independent responses in colon cancer cells. A previous report showed that KLF4 expression in colon cancer cells was regulated by over expression of the adenomatous polyposis coli gene and by the tumor suppressor homeodomain protein CDX2 (42). Moreover, APC also enhanced CDX2 expression suggesting an APC-CDX2-KLF4 sequence for activation of KLF4. In the present study, it has now been demonstrated that KLF4 expression is also enhanced by β-CDODA-Me through a PPARγ-dependent pathway.

Example 8

Effects of Compounds of the Invention on Pancreatic Cell Lines

Figure 14:
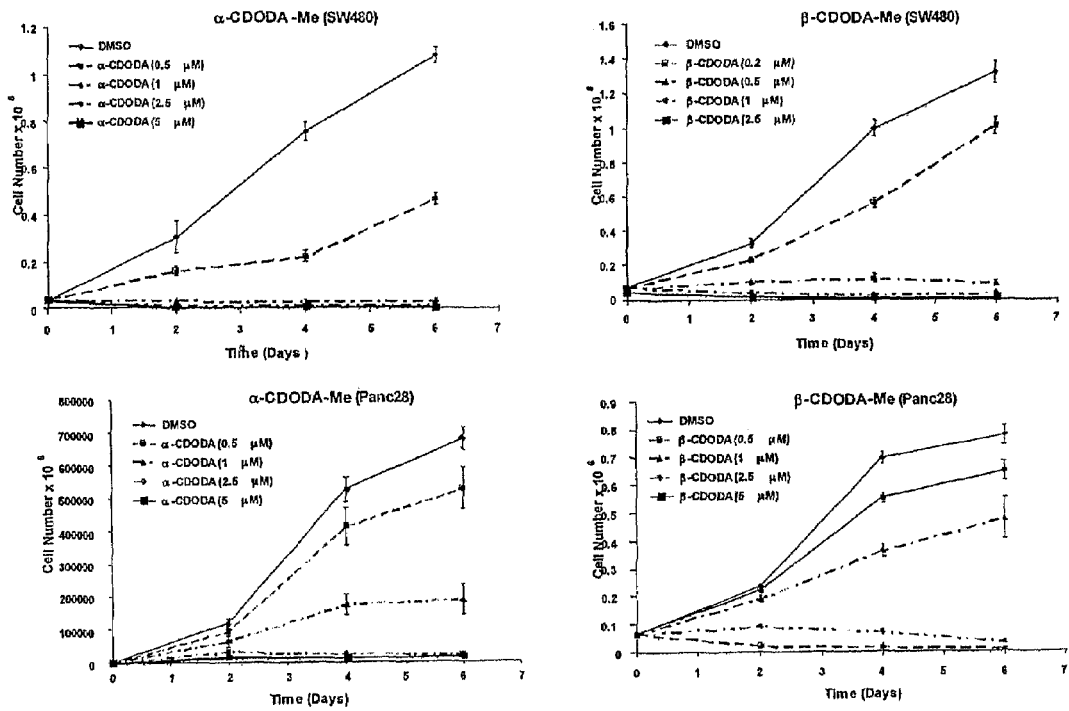
FIG. 14 shows the inhibition of colon (SW480, top) and pancreatic (Panc28, bottom) cancer cells by α- and β-CDODA-Me compounds.

The cytotoxicity α- and β-CDODA-Me isomers (Examples 4(b) and 4(a), respectively) pancreatic cancer cells was also investigated. FIG. 14 illustrates the growth inhibitory effects of α- and β-CDODA-Me in Panc28 pancreatic cancer cells, alongside SW580colon cancer cells for reference. The $IC_{50}$ values for α- and β-CDODA-Me were 0.5 and 0.2-0.5 μM, respectively, in SW480 cells and 0.5-1.0 and 1-2.5 μM in Panc28 pancreatic cancer cells. In contrast, the corresponding α-CDODA and β-CDODA (Examples 3(b) and 3(a), respectively) and analogs that do not contain cyano groups were 4-20 times less toxic than the α- and β-CDODA-Me isomers. These data, coupled with ongoing studies in other cancer cell lines demonstrate that $IC_{50}$ values vary from the high nM to low μM concentrations.

Example 9

Effects of Compounds of the Invention on Sp Protein Degradation

Figure 15:
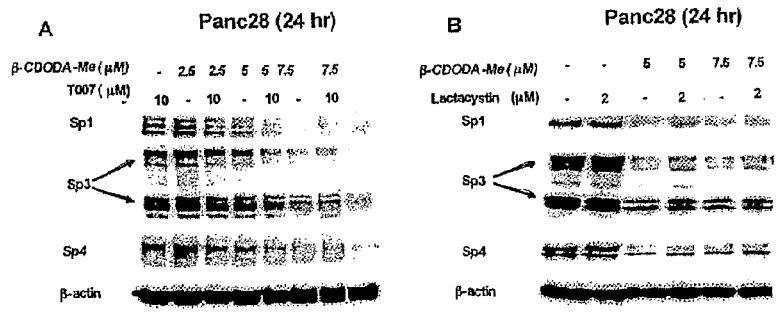
FIG. 15 includes gels showing that β-CDODA-Me induces Sp protein degradation in Panc28 cells. This response is not reversed by T007 (A) and only a minimal amount of reversal is observed with lactacystin (B).
Figure 16:
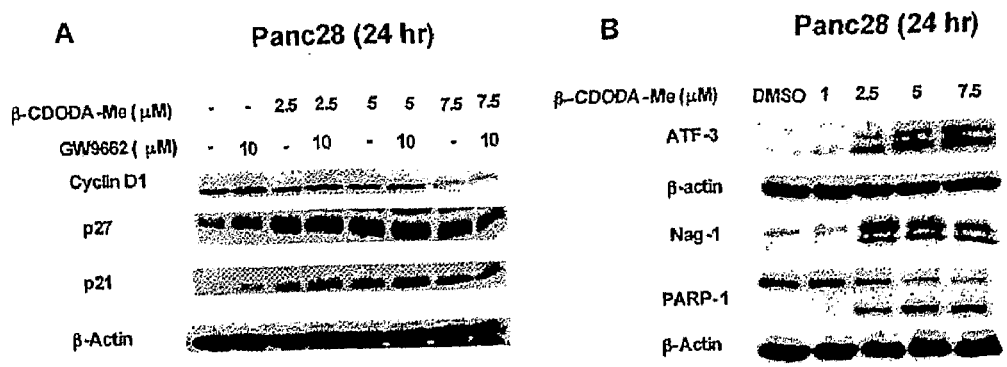
FIG. 16 includes gels showing the effects of β-CDODA-Me cell cycle proteins (A) and NAG-1/ATF-3 and PARP cleavage (B) in Panc28 cells.

Sp proteins such as Sp1, Sp3 and Sp4 are highly expressed in cancer cells, and Sp1 is overexpressed in multiple tumors compared to non-tumor tissue. Research has demonstrated by RNA interference experiments using small interfering RNAs for Sp1 (iSp1), Sp3 (iSp3) and Sp4 (iSp4) that these proteins are required for cell cycle progression, angiogenesis and survival (72, 67). Subsequent studies have identified the COX-2 inhibitors celecoxib, tolfenamic acid and structurally related NSAIDs, and the naturally occurring anticancer drug betulinic acid as agents that act through degradation of Sp proteins. For example, betulinic acid activates Sp protein degradation in prostate cancer cells and tumors and this is accompanied by decreased Sp-dependent expression of survivin (antiapoptotic), VEGF (angiogenic) and cell cycle genes. In other studies, it has been shown that VEGF receptor 1 (VEGFR1) and VEGFR2 expression is Sp-dependent and chemical-induced downregulation of Sp proteins results in decreased VEGFR1 and VEGFR2 levels in cancer cells. It is shown here that part of the underlying mechanism of action of β-CDODA-Me is also due to Sp protein degradation. Results in FIG. 15 show that after treatment of Panc28 cells with β-CDODA-Me, there was a concentration-dependent decrease in Sp1, Sp3 and Sp4 protein expression in Panc28 cells, and this was accompanied by a parallel decrease in VEGF expression and induction of caspase-dependent apoptosis (PARP cleavage) (FIG. 16). β-CDODA-Me-dependent effects on Sp protein expression in Panc28 cells were not blocked by PPARγ antagonists (FIG. 15A) or the proteasome inhibitor lactacystin (FIG. 15B). Betulinic acid induces proteasome-dependent degradation of Sp protein in prostate cancer cells/tumors; however, it was evident in these studies that in Panc28 cells, the effects of β-CDODA-Me on Sp proteins were proteasome-independent.

Figure 17:
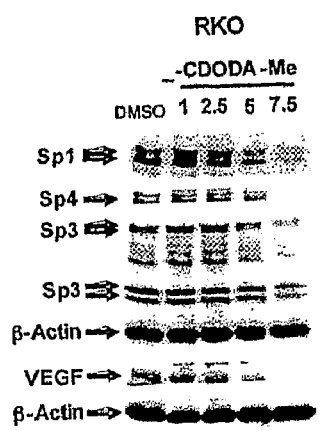
FIG. 17 includes a gel showing that β-CDODA-Me decreases Sp protein expression in RKO cells. These effects are not reversed by T007 or proteasome inhibitors.

The effects of β-CDODA-Me on Sp protein levels in RKO cells (FIG. 17) and the results were similar to those observed in Panc28 cells. β-CDODA-Me decreased Sp protein expression in these cells and this was accompanied by decreased VEGF protein expression. These results confirm that β-CDODA-Me also induces Sp1, Sp3 and Sp4 protein loss in both colon and pancreatic cancer cells and thereby exhibits activity similar to that reported for betulunic acid and tolfenamic acid. However, in both RKO and Panc28 cells, Sp protein expression was decreased through proteasome-independent pathways. Therefore, one of the mechanisms by which the compounds of the present invention inhibit cancer cell and tumor growth is through Sp protein expression, resulting in growth inhibition, decreased cell survival, and induction of antiangiogenic pathways through targeting Sp-dependent gene expression.

Example 9

Effects of the Compounds of the Invention on Prostate Cancer Cell Lines

Materials and Methods
Cell lines: LNCaP human prostate carcinoma cells were obtained from American Type Culture Collection (Manassas, Va.). Fetal bovine serum was obtained from JRH Biosciences, Lenexa, Kans. LNCaP cells were maintained in RPMI 1640 (Sigma Chemical, St. Louis, Mo.) supplemented with 0.22% sodium bicarbonate, 0.011% sodium pyruvate, 0.45% glucose, 0.24% HEPES, 10% FBS, and 10 mL/L of 100× antibiotic/antimycotic solution (Sigma). Cells were maintained at 37° C. in the presence of 5% $CO_2$.

Antibodies and Reagents: Antibodies for poly(ADP-ribose) polymerase, cyclin D1, p27, FKBP51, AR, ATF3, Akt and caveolin-1 were purchased from Santa Cruz Biotechnology, Inc. (Santa Cruz, Calif.). PSA was obtained from Dako Denmark A/S (Glostrup, Denmark); NAG-1 was purchased from Upstate Biotechnology (Charlottesville, Va.); and EGR-1, pAKT, pERK, ERK, pJNK, JNK were obtained from Cell Signaling Technology Inc. (Danvers, Mass.). Monoclonal β-actin antibody and dihydrotesterone were purchased from Sigma-Aldrich. Reporter lysis buffer and luciferase reagent for luciferase studies were purchased from Promega (Madison, Wis.). β-Galactosidase (β-Gal) reagent was obtained from Tropix (Bedford, Mass.), and lipofectamine reagents were supplied by Invitrogen (Carlsbad, Calif.). Western Lightning chemiluminescence reagents were from Perkin-Elmer Life Sciences (Boston, Mass.). The PPARγ antagonist N-(4'-aminopyridyl)-2-chloro-5-nitrobenzamide (T007) was prepared in this laboratory and the synthesis of the GA derivatives has previously described (90).

Cell Proliferation and DNA Fragmentation Assays: LNCaP prostate cancer cells ($2 \times 10^4$ per well) were added to 12-well plates and allowed to attach for 24 hr. The medium was then changed to DMEM/Ham's F-12 media containing 2.5% charcoal-stripped FBS, and either vehicle (DMSO) or the indicated C-DIMs were added. Fresh medium and indicated compounds were added every 48 hr, and cells were then trypsinized and counted after 2, 4, and 6 days using a Coulter Z1 cell counter (Beckman Coulter, Fullerton, Calif.). Each experiment was done in triplicate, and results are expressed as means±S.E. for each set of three experiments. The DNA fragmentation assay was performed using a BioVision Apoptotic DNA ladder extraction kit (BioVision, Mountain View, Calif.) according to the manufacturer's protocol.

Transfections: The Gal4 reporter construct containing 5× Gal4 response elements (pGal4) was kindly provided by Dr. Marty Mayo (University of North Carolina, Chapel Hill, N.C.). The Gal4 DBD-PPARγ construct was a gift of Dr. Jennifer L. Oberfield (Glaxo Wellcome Research and Development, Research Triangle Park, N.C.). The PPRE-luc construct contains three tandem PPREs with a minimal TATA sequence linked to the luciferase gene in pGL2. The AR-luc construct containing the −5400 to +580 region of the androgen receptor promoter was provided by Dr. Donald J. Tindall (Mayo Clinic, Rochester, Minn.), and the PSA-luc construct containing the 5.8-kilobase region of the PSA promoter was provided by Dr. Hong-Wu Cheng (University of California, Davis, Calif.). LNCaP cells ($1 \times 10^5$) were seeded in 12-well plates in DMEM/Ham's F-12 media supplemented with 2.5% charcoal-stripped FBS and grown overnight. Transient transfections were performed using Lipofectamine reagent (Invitrogen) according to the protocol provided by the manufacturer. Transfection studies were performed using 0.4 μg of Gal4Luc, 0.04 μg of β-galactosidase, 0.04 μg of Gal4 DBD-PPARγ, 0.4 μg of AR-luc, and 0.3 μg of PSA-luc. Six hr after transfection, the transfection mix was replaced with complete media containing either vehicle (DMSO) or the indicated ligand for 20 to 22 hr. Cells were then lysed with 100 μl of 1× reporter lysis buffer, and 30 μl of cell extract was used for luciferase and β-galactosidase assays. A Lumicount luminometer (PerkinElmer Life and Analytical Sciences) was used to quantify luciferase and β-galactosidase activities, and the luciferase activities were normalized to β-galactosidase activity.

Real-Time PCR: Total RNA was isolated using the RNeasy Protect Mini kit (QIAGEN, Valencia, Calif.) according to the manufacturer's protocol. RNA was eluted with 30 μl of RNasefree water and stored at −80° C. RNA was reverse transcribed using Superscript II reverse transcriptase (Invitrogen) according to the manufacturer's protocol. cDNA was prepared from the LNCaP cell line using a combination of oligodeoxythymidylic acid and dNTP mix (Applied Biosystems, Foster City, Calif.) and Superscript II (Invitrogen). Each PCR was carried out in triplicate in a 25-μl volume using SYBR Green Master mix (Applied Biosystems) for 15 min at 95° C. for initial denaturing, followed by 40 cycles of 95° C. for 30 s and 60° C. for 1 min in the ABI Prism 7700 sequence detection system (Applied Biosystems). The ABI Dissociation Curves software was used after a brief thermal protocol (95° C. 15 s and 60° C. 20 s, followed by a slow ramp to 95° C.) to control for multiple species in each PCR amplification. The comparative CT method was used for relative quantitation of samples. Values for each gene were normalized to expression levels of TATA-binding protein. Primers were purchased from Integrated DNA Technologies (Coralville, Iowa). The sequences of the primers used for reverse transcription-PCR were as follows: AR forward, 5'-GTA CCC TGG CGG CAT GGT-3' [SEQ ID NO: 1] and AR reverse, 5'-CCC ATT TCG CTT TTG ACA CA-3' [SEQ ID NO: 2]; PSA forward, 5'-GCA TTG AAC CAG AGG AGT TCT TG-3' [SEQ ID NO: 3] and PSA reverse, 5'-TTG CGC ACA CAC GTC ATT G-3' [SEQ ID NO: 4]; and TATA-binding protein forward, 5'-TGC ACA GGA GCC AAG AGT GAA-3' [SEQ ID NO: 5] and reverse, 5'-CAC ATC ACA GCT CCC CAC CA-3' [SEQ ID NO: 6].

Western Blot Analysis: Cells were seeded in DMEM:Ham's F-12 media containing 2.5% charcoal-stripped FBS for 24 hr and then treated with either the vehicle (DMSO) or the indicated compounds. Cells were collected by scraping in 150 μl high salt lysis buffer (50 mM HEPES, 0.5 M NaCl, 1.5 mM MgCl2, 1 mM EGTA, 10% (v/v) glycerol, 1% (v/v) Triton-X-100 and 5 μL/ml of Protease Inhibitor Cocktail (Sigma). The lysates were incubated on ice for 1 hr with intermittent vortexing followed by centrifugation at 20,000 g for 10 min at 4° C. Before electrophoresis, samples were boiled for 3 min at 100° C.; the amount of protein was determined and 60 μg protein applied per lane. Samples were subjected to SDS-PAGE on 10% gel at 120 V for 3 to 4 hr. Proteins were transferred on to polyvinylidene difluoride membrane (PVDF; Bio-Rad, Hercules, Calif.) at 0.9 amp for 90 min at 4° C. in 1× transfer buffer (48 mM Tris-HCl, 39 mM glycine, and 0.025% SDS). The membranes were blocked for 30 min with 5% TBST-Blotto (10 mM Tris-HCl, 150 mM NaCl (pH 8.0), 0.05% Triton X-100 and 5% non-fat dry milk) and incubated in fresh 5% TBST-Blotto with primary antibody overnight with gentle shaking at 4° C. After washing with TBST for 10 min, the PVDF membrane was incubated with secondary antibody (1:5000) in 5% TBST-Blotto for 2-3 hr. The membrane was washed with TBST for 10 min and incubated with 10 ml of chemiluminescence substrate (PerkinElmer Life Sciences) for 1.0 min and exposed to ImageTeK-H medical imaging film (Eastman American X-ray Supply, Inc.).

Statistical Analysis: Statistical differences between different groups were determined by ANOVA and Scheffe's test for significance. The data are presented as mean±S.E. for at least three separate determinations for each treatment group.

Figure 18:
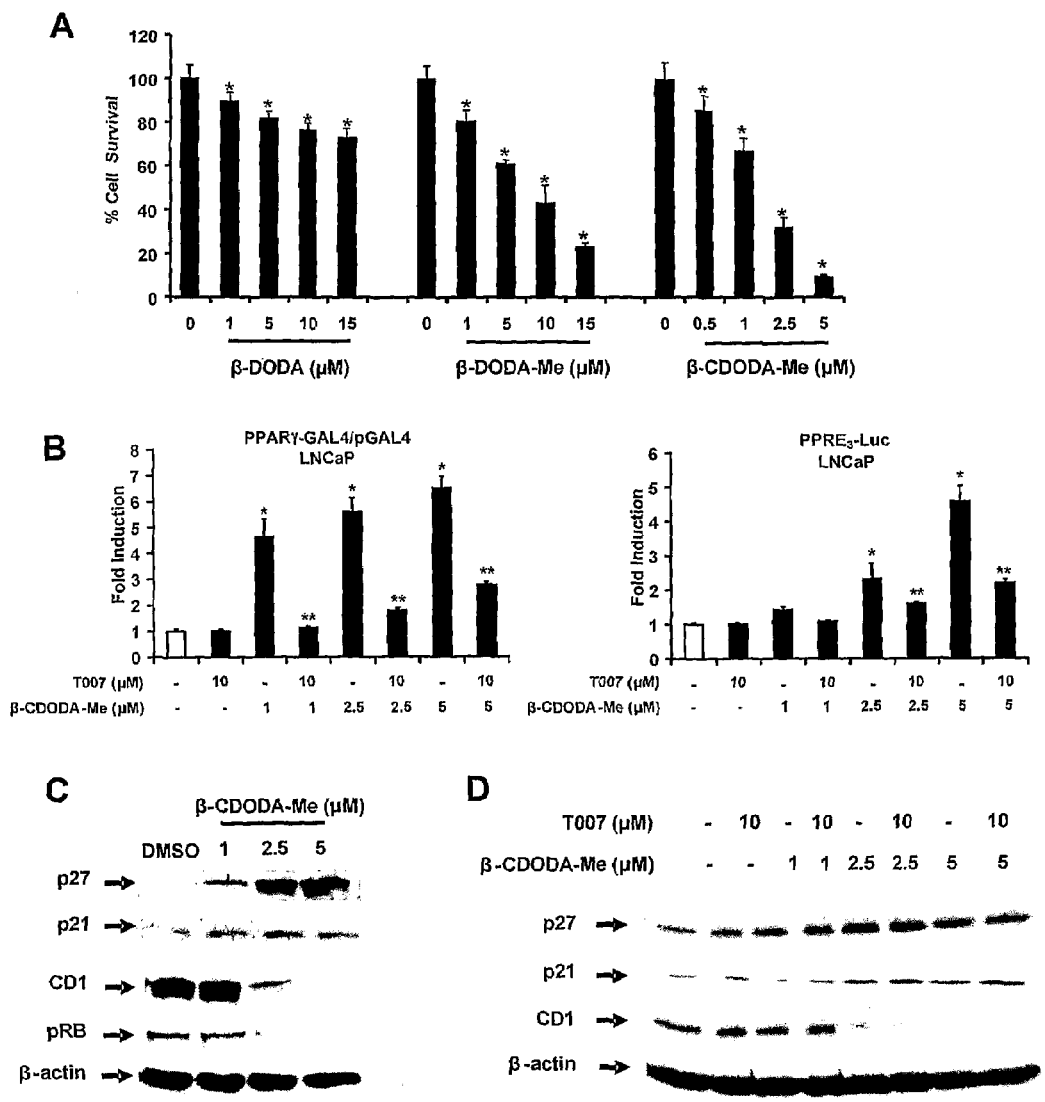
FIG. 18 shows the effects of β-CDODA-Me and related compounds on LNCaP cell survival, activation of PPARγ, and modulation of cell cycle genes. (A) Cell survival. LNCaP cells were treated with different concentrations of β-DODA, β-DODA-Me or β-CDODA-Me for 96 hr, and the % cell survival relative to DMSO (solvent control set at 100%) was determined as described in the Examples. Results are expressed as means±SE for three separate determinations for each treatment group, and significantly (p<0.05) decreased survival is indicated (*). (B) β-CDODA-Me activates PPARγ. LNCaP cells were treated with β-CDODA, T007 or their combination, transfected with PPARγ-GAL4/pGAL4 or PPRE-luc, and luciferase activity determined as described in the Examples. Results are expressed as means±SE for three replicate determinations for each treatment group, and significant (p<0.05) induction by β-CDODA-Me (*) and inhibition after cotreatment with T007 (**) are indicated. Modulation of cell cycle genes by β-CDODA-Me alone (C) and in combination with T007 (D). Cells were treated as indicated for 24 hr, and whole cell lysates were analyzed by Western blot analysis as described in the Examples.

Results a) Cell Proliferation and Activation of PPARγ

β-DODA (Example 1(a)) exhibited minimal inhibition of LNCaP cell growth with a $IC_{50}$ value >15 μM whereas the $IC_{50}$ for the corresponding methyl ester derivative (Example 2a) was between 10-15 μM (FIG. 18A). Introduction of a 2-cyano group to give β-CDODA-Me (Example 4(a)) increased the cytotoxicity by at least an order of magnitude and the $IC_{50}$ was approximately 1 μM in LNCaP cells (FIG. 18A). These results were similar to those observed in colon cancer cells (Example 7) and demonstrate the importance of 2-substitution in mediating the cytotoxicity of GA derivatives. The induction of PPARγ-dependent transactivation by β-CDODA-Me was also investigated in LNCaP cells transfected with PPARγ-GAL4/GAL4-Luc or $PPRE_3$-Luc constructs and treated with 1-5 μM concentrations. β-CDODA-Me significantly induced luciferase activity (FIG. 18B) and in cells cotreated with β-CDODA-Me plus 10 μM T007 (a PPARγ antagonist), there was significant inhibition of induced transactivation. In contrast, β-DODA-Me and β-1-DODA-Me (Example 5) did not activate PPARγ. PPARγ agonists typically modulate expression of one or more of the cell cycle proteins p27, p21 and cyclin D1, and FIG. 18C illustrates the effects of 1-5 μM β-CDODA-Me on expression of these proteins in LNCaP cells. There was a concentration-dependent induction of p27 and p21 and a decrease in cyclin D1 proteins and Rb phosphorylation in cells treated with β-CDODA-Me alone, and similar results were observed in cells cotreated with the PPARγ antagonist T007 and β-CDODA-Me (FIG. 18D) suggesting that these responses were PPARγ-independent.

b) Induction of Proapoptotic Responses by β-CDODA-Me.

Figure 19:
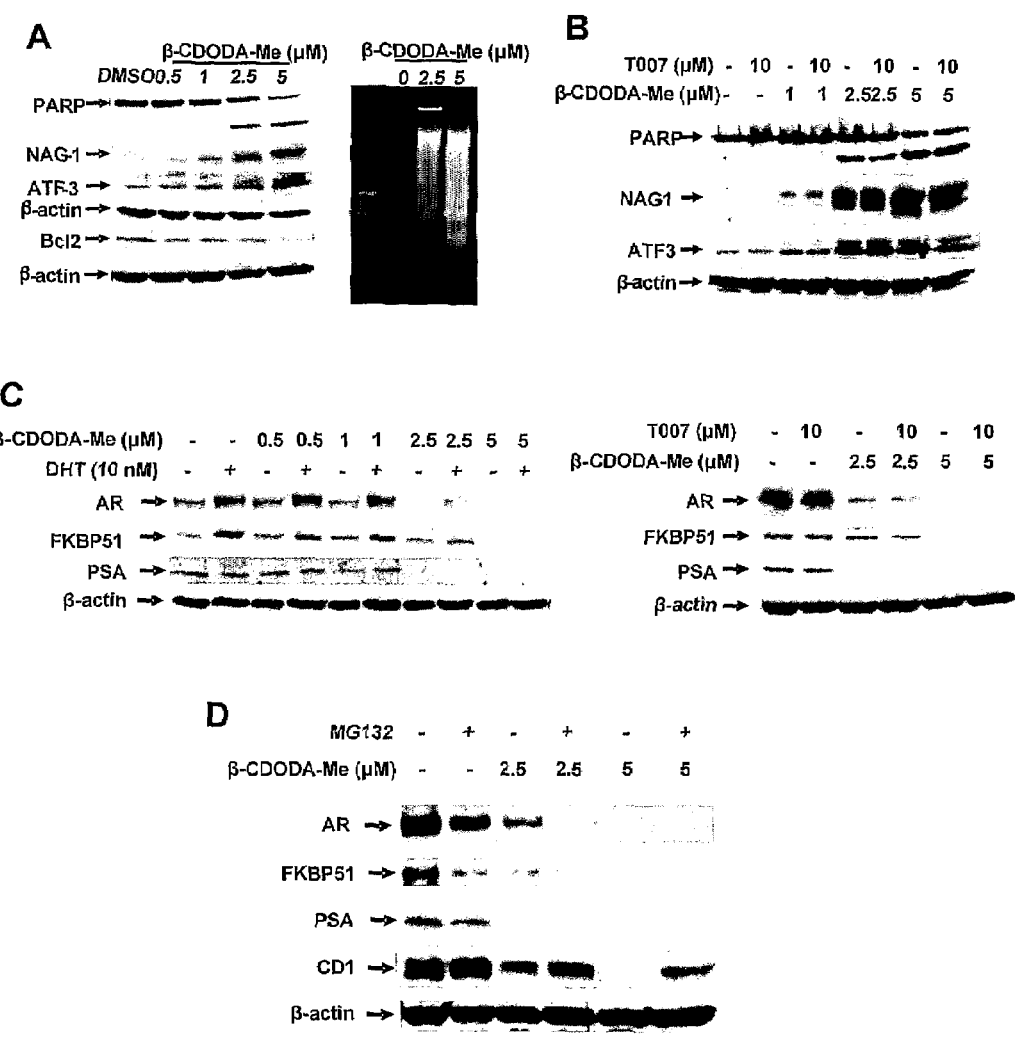
FIG. 19 shows that β-CDODA induces apoptotic pathways and decreases androgen-responsiveness in LNCaP cells. β-CDODA-Me alone (A) and in combination with T007 (B) induces proapoptotic pathways. LNCaP cells were treated as indicated for 24 hr, and whole cell lysates were analyzed by Western blot analysis as described in the Examples. β-CDODA-Me-induced DNA fragmentation (A) was also determined as described. Effects of β-CDODA-Me alone and in combination with DHT or T007 (C) or MG132 (D), and whole cell lysates were analyzed by Western blot analysis as described in the Examples.
Figure 20:
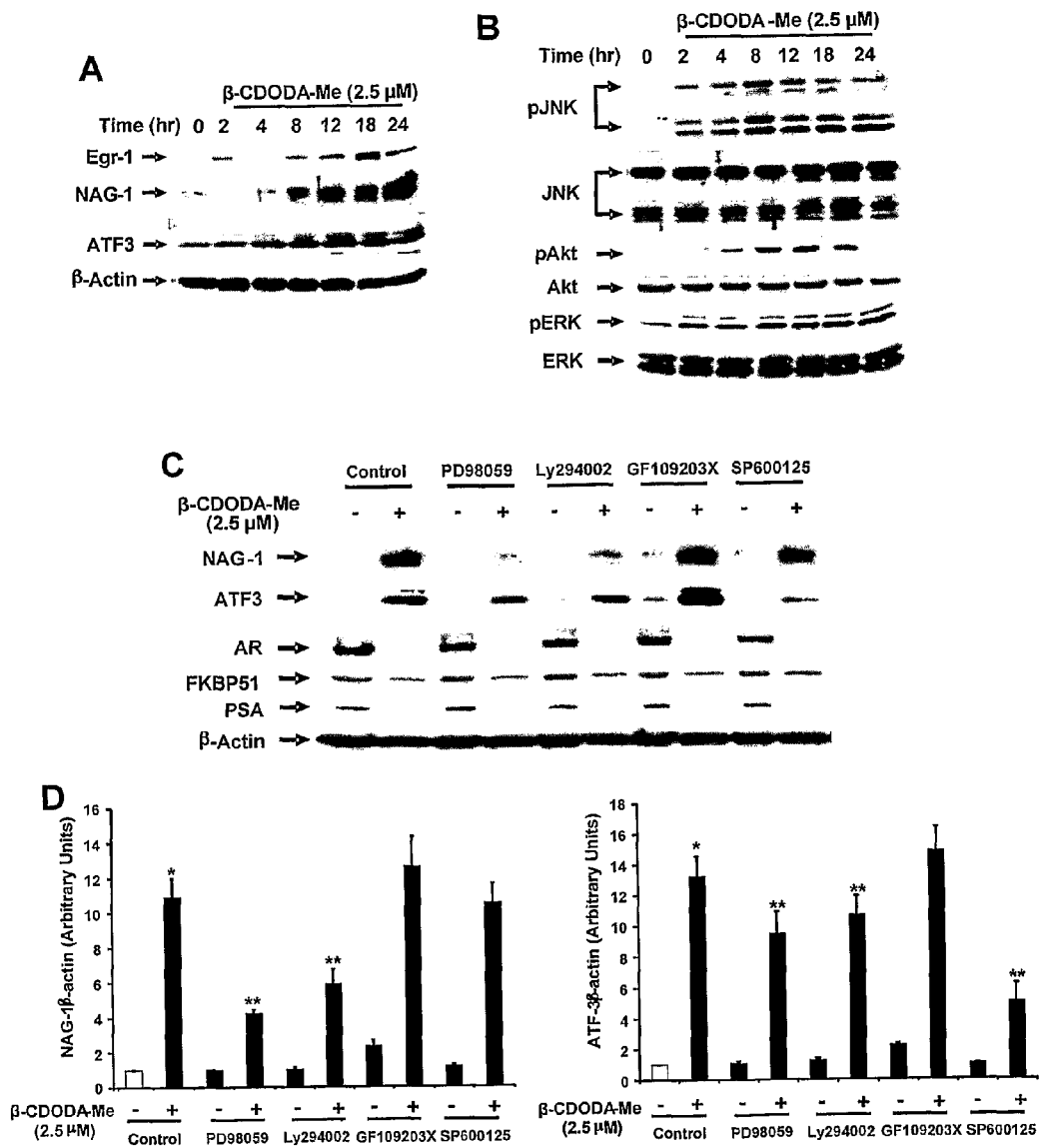
FIG. 20 shows that β-CDODA-Me induces proapoptotic proteins and kinases. Induction of NAG-1, ATF-3 and Egr-1 (A) and kinases (B) by β-CDODA-Me. LNCaP cells were treated with 2.5 μM β-CDODA-Me, and whole cell lysates isolated at different times after treatment were analyzed by Western blot analysis as described in the Examples. Effects of kinase inhibitors on proapoptotic responses (C) and quantitation of NAG-1 and ATF-3 expression (D). LNCaP cells were treated with 2.5 μM β-CDODA alone or in combination with various kinase inhibitors and after 24 hr, whole cell lysates were analyzed by Western blot analysis. Levels of NAG-1 and ATF-3 proteins (normalized to β-actin) (D) are means±SE for three separate determinations for each treatment group and significantly (p<0.05) decreased levels after cotreatment with a kinase inhibitor are indicated (**).

NAG-1 and ATF-3 are proapoptotic proteins induced by PPARγ agonists and results in FIG. 19 show that 1-5 μM β-CDODA-Me induced NAG-1 and ATF-3 which are often co-induced and this was accompanied by caspase-dependent PARP cleavage, DNA fragmentation, and decreased bcl2 expression in LNCaP cells. In LNCaP cells cotreated with β-CDODA-Me plus T007 (FIG. 19B), the induced responses were not inhibited by the PPARγ antagonist indicating that induction of these proapototic responses was receptor-independent. Previous studies show that different structural classes of PPARγ agonists downregulate AR expression in LNCaP cells and this response can also result in activation of apoptosis (91, 92). FIG. 19C summarizes the effects of β-CDODA-Me on AR expression in the presence or absence of 10 nM DHT and also on the expression of FKBP51 and PSA, two androgen-responsive genes in LNCaP cells. DHT increases expression of AR due to stabilization of the receptor and also induces both androgen-responsive FKBP51 and PSA genes and, in cells treated with 1-5 μM β-CDODA-Me, there was a concentration-dependent decrease in AR, PSA and FKBP51 expression in the presence or absence of DHT. In addition, downregulation of AR, PSA and FKBP51 proteins in LNCaP cells treated with β-CDODA-Me was not affected by cotreatment with the PPARγ antagonist T007 (FIG. 19D) or the proteasome inhibitor MG132 (FIG. 19E). In contrast, β-CDODA-Me-dependent degradation of cyclin D1 was inhibited after cotreatment with MG132 and these observations are similar to those reported for other PPARγ agonists that induce proteasome-dependent degradation of cyclin D1 (22, 94-96). These results clearly show that β-CDODA-Me decreases expression of androgen-responsive genes and AR through PPARγ-independent pathways. The downregulation of AR in cells treated with β-CDODA-Me is consistent with the induction of apoptosis by this compound since decreased AR expression by small inhibitory RNAs in LNCaP cells also induces apoptosis (93).

c) β-CDODA-Me Induces Kinase-Dependent Activation of Proapoptotic/Growth Inhibitory Pathways Previous studies show that NAG-1 is induced by some PPARγ agonists and other cytotoxic compounds in colon cancer cells (94, 97, 98-100) through PI3K-dependent activation of EGR-1 which acts as a trans-acting factor to induce NAG-1 expression. FIG. 20A summarizes the time-dependent induction of EGR-1, ATF-3 and NAG-1 by 2.5 μM β-CDODA-Me and the induction responses followed a similar time course, whereas EGR-1 dependent induction of NAG-1 in colon cancer cells is associated with the increased expression of EGR-1 prior to induction of NAG-1 (94, 100). Previous studies show that NAG-1 induction is kinase-dependent (94, 100), and results in FIG. 20B show that 2.5 μM β-CDODA-Me induces activation of the JNK (p-JNK), PI3K (p-Akt) and MAPK (p-Erk) pathways. Maximal activation of JNK and PI3K was observed after 8 and 8-12 hr, respectively, whereas p-Erk activation remained elevated for 24 hr. The effects of inhibitors of MAPK (PD98059), PI3K (LY294002), protein kinase C (GF109203X) and JNK (SP600125) on induction of NAG-1 and ATF3 and decreased expression of AR, PSA and FKBP51 was also investigated in LNCaP cells treated with 2.5 μM β-CDODA-Me (FIG. 20C). Both PD98059 and LY294002 inhibited induction of NAG-1 by β-CDODA-Me. These inhibitors also blocked induction of ATF-3; however, the JNK inhibitor SP600125 was the most potent inhibitor of ATF-3 induction (FIGS. 20C and 20D). In contrast, decreased expression of AR, PSA and FKBP51 in LNCaP cells treated with β-CDODA-Me was unaffected by kinase inhibitors.

Figure 21:
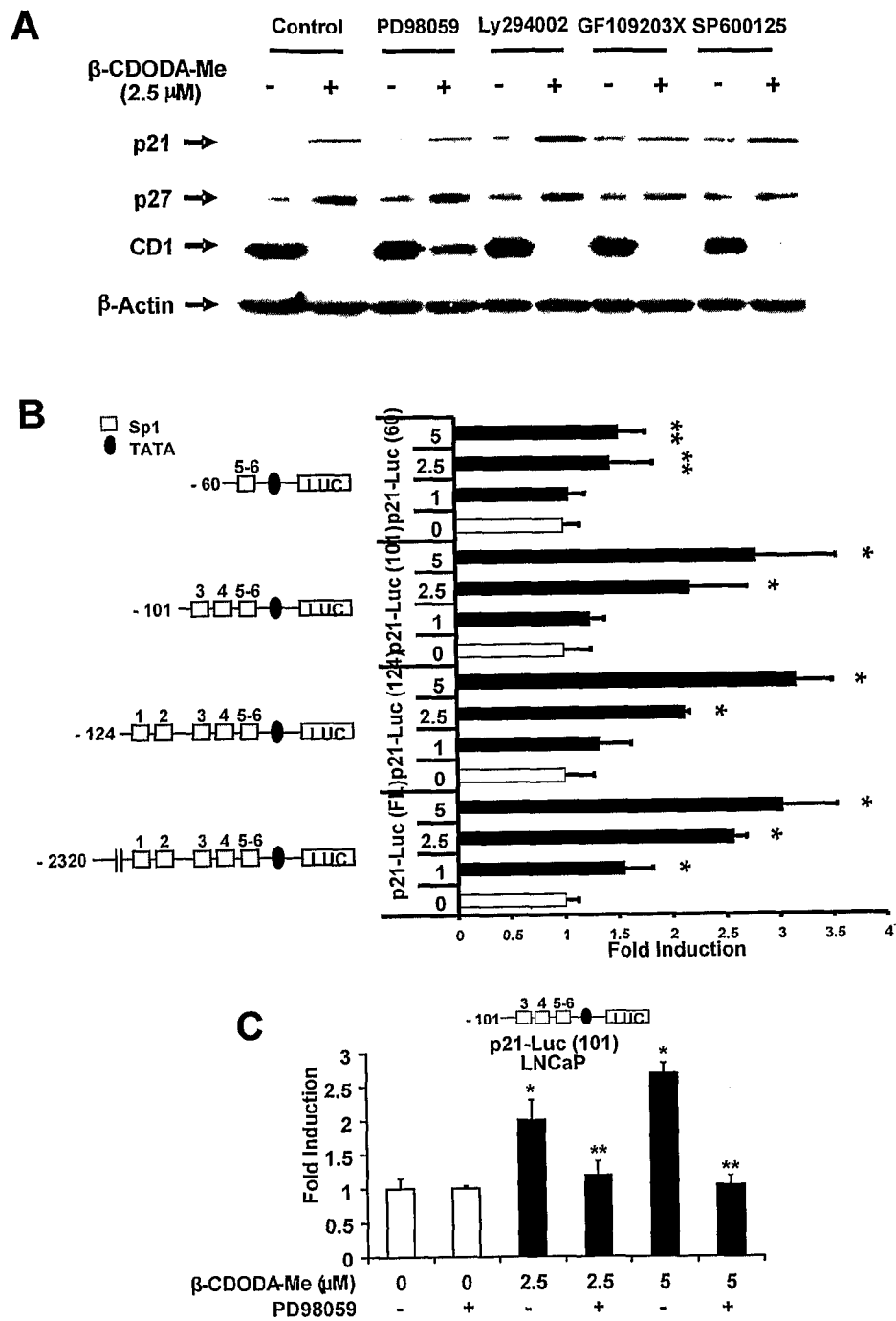
FIG. 21 shows that β-CDODA-Me induction of p21 is MAPK-dependent. (A) Effects of kinase inhibitors on induction of p21. LNCaP cells were treated with DMSO, 2.5 μM β-CDODA-Me alone or in combination with kinase inhibitors for 24 hr, and whole cell lysates were analyzed by Western blot analysis as described in the Examples. (B) β-CDODA-Me activates p21 promoter constructs. LNCaP cells were transfected with p21 promoter constructs, treated with DMSO or different concentrations of β-CDODA-Me, and luciferase activity was determined as described in the Examples. Results are means±SE for three separate determinations for each treatment group, and significant (p<0.05) induction of activity is indicated (*). (C) Inhibition by PD98059. Cells were transfected with p21-luc(101), treated with DMSO, β-CDODA-Me alone or in combination with 10 μM PD98059. Results are expressed as means±SE for three separate determinations for each treatment group, and significant (p<0.05) induction by β-CDODA-Me (*) and inhibition after cotreatment with PD98059 (**) are indicated.
Figure 22:
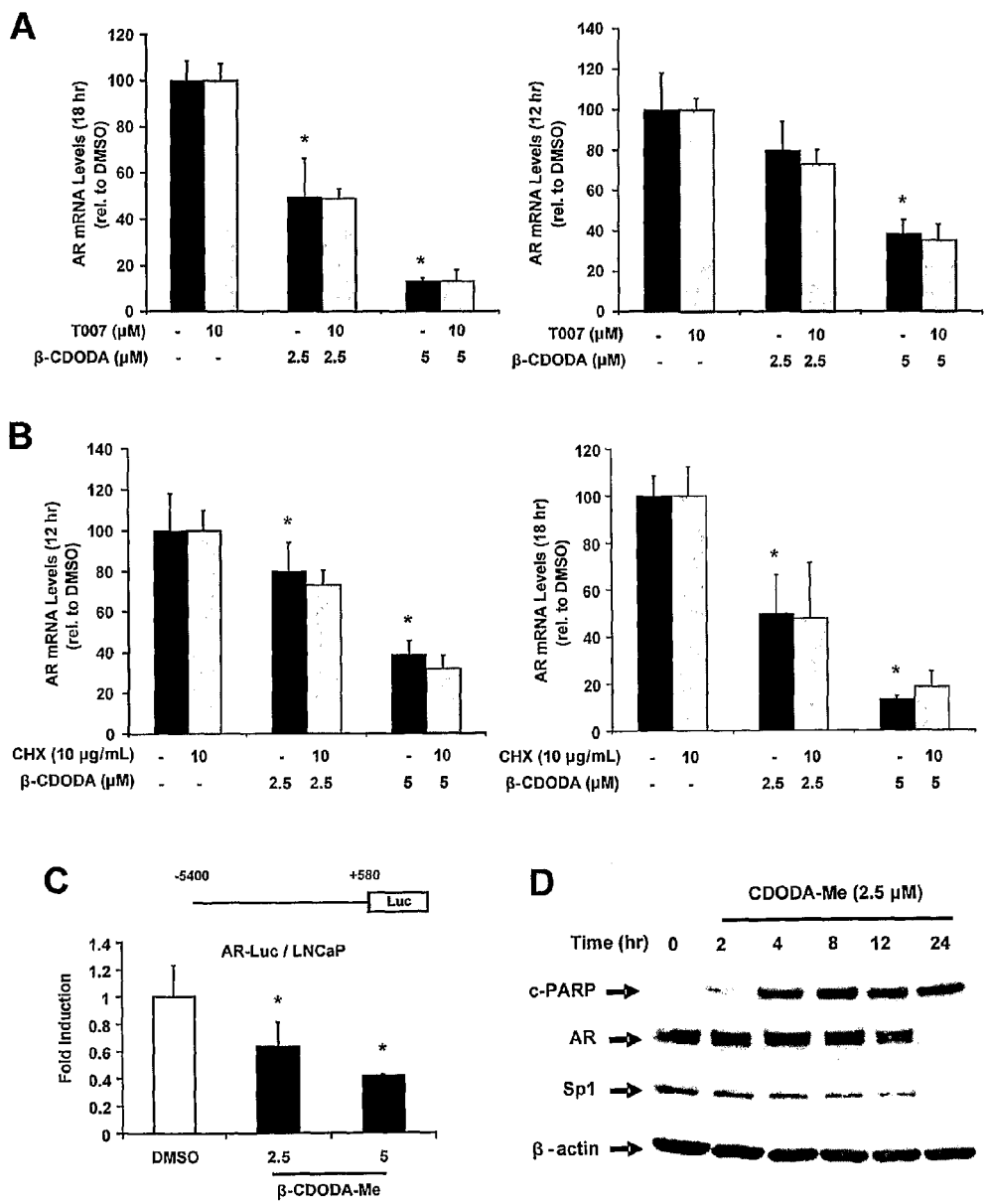
FIG. 22 shows that β-CDODA-Me decreases AR gene expression. Effects of T007 (A) and cycloheximide (B) on β-CDODA-Me-dependent effects on AR gene expression. LNCaP cells were treated with β-CDODA-Me alone or in combination with T007 or cycloheximide for 12 or 18 hr, and AR mRNA levels were determined by real time PCR as described in the Examples. (C) β-CDODA-Me decreases AR promoter activity. LNCaP cells were transfected with AR-luc, treated with DMSO or β-CDODA-Me, and luciferase activity determined as described in the Examples. Results are means±SE for three separate experiments for each treatment group and a significant (p<0.05) decrease in activity is indicated (*). (D) Time-dependent effects of β-CDODA-Me on AR, Sp1 and PARP (cleaved). LNCaP cells were treated with DMSO or β-CDODA-Me for up to 24 hr, and whole cell lysates were analyzed by Western blot analysis as described in the Examples.

While not wishing to be limited by theory, these results suggest that the underlying pathways associated with the growth inhibitory/proapoptotic pathways induced by β-CDODA-Me in LNCaP cells are due in part to activation of kinases. Therefore, the effects of kinase inhibitors on modulation of cell cycle proteins by β-CDODA-Me were also investigated and the downregulation of cyclin D1 and induction of p21 were partially blocked in cells cotreated with the MAPK inhibitor PD98059 (FIG. 21A), and MAPK-dependent activation of p21 has previously been observed in embryonal rhabdomyosarcoma cell lines treated with TPA (101). Results in FIG. 21B show that the 1-5 μM β-CDODA-Me also induces luciferase activity in LNCaP cells transfected with constructs containing −2325 to +8 [p21-Luc(FI)], −124 to +8 [p21-Luc (−124)], −101 to +8 [p21-Luc (−101)], and −60 to +8 [p21-Luc (−60)] p21 promoter inserts. The latter 3 constructs contain the 6 proximal GC rich site (VI-I) and the results of the transfection studies suggest that these GC-rich sites are necessary for β-CDODA-Me-induced transactivation. Deletion analysis of the p21 promoter indicates that loss of inducibility [i.e. p21-luc(60)] is associated with loss of GC-rich sites IV and III which are essential for MAPK-dependent activation of p21 by β-CDODA-Me. The role of MAPK in activation of the p21 promoter was confirmed in LNCaP cells transfected with p21-luc(101); β-CDODA-Me induced luciferase activity and cotreatment with the MAPK inhibitor PD98059 inhibited this response (FIG. 21C). These results show that the induction of p21 and the proapototic NAG-1 protein by β-CDODA-Me were related to the activation of MAPK and PI3K but were independent of PPARγ (FIGS. 18D and 19B).

d) β-CDODA-Me Differentially Decreases AR and PSA Gene Expression in LNCaP Cells.

β-CDODA-Me decreases expression of AR, PSA and FKBP51 protein levels through proteasome and PPARγ-independent pathways (FIGS. 19C-19E) and these responses are also not modulated by kinase inhibitors (FIG. 20B). The results in FIG. 22A show that β-CDODA-Me also decreases AR mRNA levels after treatment for 12 and 18 hr, and cotreatment with the PPARγ antagonist T007 did not affect mRNA levels confirming the β-CDODA-Me-induced downregulation of AR mRNA levels was also PPARγ-independent. Similar results were obtained in LNCaP cells treated with β-CDODA-Me alone or in the presence of the protein synthesis inhibitor cycloheximide (10 µg/ml) (FIG. 22B); cycloheximide did not modulate the effects of β-CDODA-Me, suggesting that an induced inhibitory protein(s) does not mediate the effects of β-CDODA-Me on AR mRNA expression. β-CDODA-Me also decreased luciferase activity in LNCaP cells transfected with the AR-Luc construct that contains the −5400 to +580 region of the AR promoter linked to the luciferase genes (FIG. 22C). The results indicate that β-CDODA-Me inhibits AR transcription without the parallel induction of inhibitory trans-acting factors. Recent studies suggest that AR downregulation of a PPARγ-inactive thiazolidinedione analog was due to downregulation of Sp protein (102). Results in FIG. 22D show that β-CDODA-Me induces a time-dependent induction of PARP cleavage and a decrease of both AR and Sp1, suggesting that decreased expression of AR may be Sp1-dependent as previously reported (102)

Figure 23:
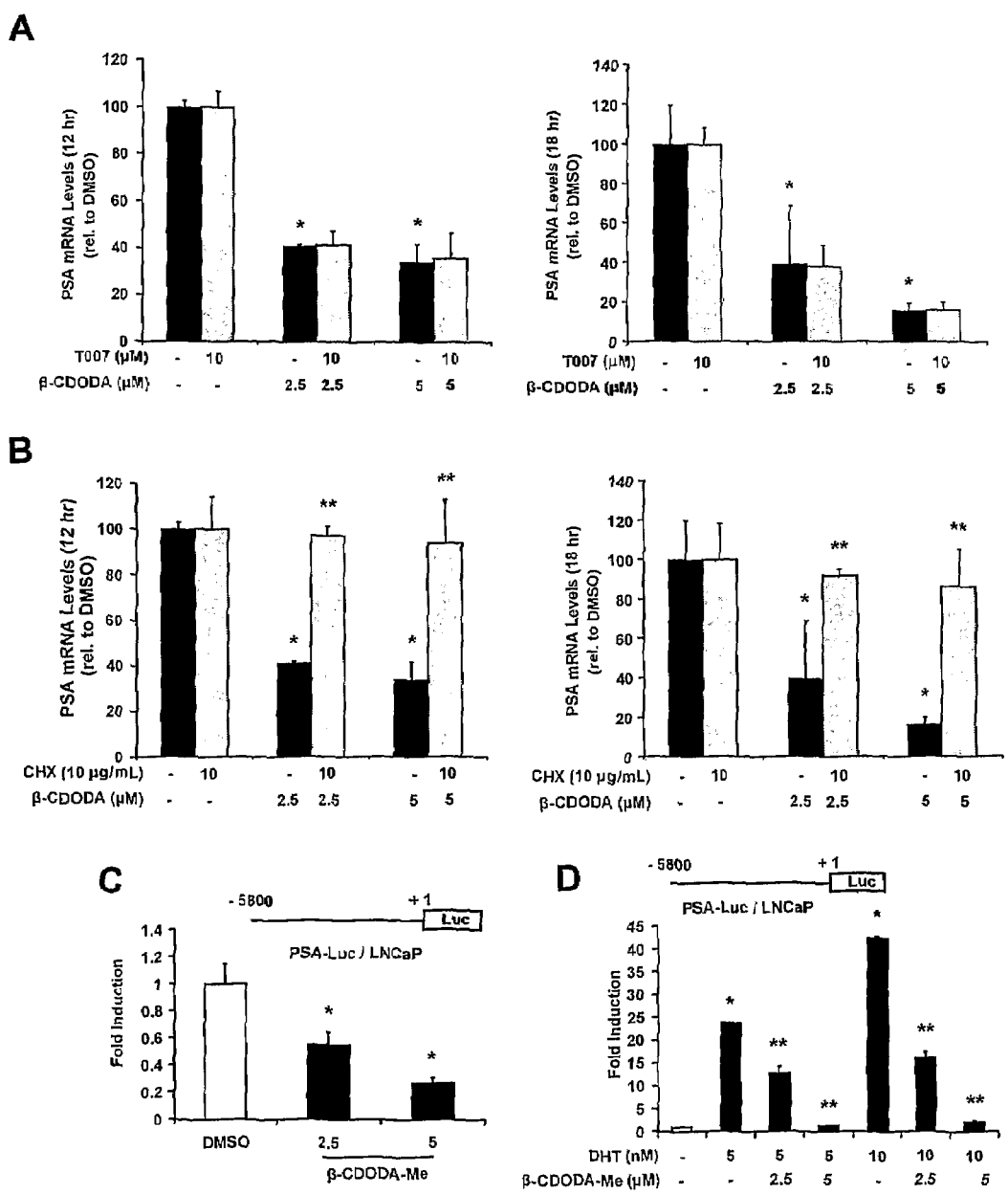
FIG. 23 shows that β-CDODA-Me decreases PSA expression. Effects of T007 (A) and cycloheximide (B) on β-CDODA-Me-dependent effects on PSA gene expression. LNCaP cells were treated with β-CDODA-Me alone or in combination with T007 or cycloheximide for 12 or 18 hr, and PSA mRNA levels were determined by real time PCR as described in the Examples. β-CDODA-Me decreases PSA promoter (C) and DHT-induced (D) PSA promoter activity. LNCaP cells were transfected with PSA-luc, treated with DMSO, β-CDODA-Me, DHT and β-CDODA-Me plus DHT (combined), and luciferase activity determined as described in the Examples. Results are means±SE for three replicate determinations for each treatment group, and significantly (p<0.05) decreased basal or DHT-induced luciferase activity by β-CDODA-Me is indicated (*).

PSA protein expression is also decreased in LNCaP cells treated with β-CDODA-Me (FIG. 19C) and similar effects were observed for PSA mRNA levels after treatment for 12 or 18 hr, and these responses were not inhibited after cotreatment with the PPARγ antagonist T007 (FIG. 23A). However, β-CDODA-Me-induced downregulation of PSA mRNA levels after treatment for 12 or 18 hr was significantly inhibited after cotreatment with cycloheximide (FIG. 23B). In addition, β-CDODA-Me inhibited transactivation in LNCaP cells transfected with the PSA-Luc construct (contains 5.85 kb of the PSA promoter insert) (FIG. 23C) and similar results were obtained for DHT-induced luciferase activity (FIG. 23D). Thus, in contrast to results obtained for AR, β-CDODA-Me inhibits PSA expression through induction of inhibitory trans-acting factors.

Discussion

In this example, the growth inhibitory and proapoptotic effects of β-CDODA-Me in LNCaP cells and the role of PPARγ in mediating these responses was investigated. β-CDODA-Me was a more potent inhibitor of LNCaP cell growth than analogs (β-DODA and β-DODA-Me) that did not contain a 2-substituent Moreover, β-CDODA-Me also activated PPARγ-dependent transactivation in transient transfection studies in LNCaP cells, and compounds without the 2-substituent were inactive as reported above for these analogs in colon cancer cells. β-CDODA-Me induced p27 expression and downregulated levels of cyclin D1 protein. β-CDODA-Me induced p21 protein in LNCaP cells and this response was not inhibited after cotreatment with PPARγ antagonist T007. β-CDODA-Me induction of p21 in LNCaP cells was due to activation of MAPK signaling which was required for induction of p21 protein and activation of the p21 promoter. This is a novel pathway for induction of p21 in LNCaP cells; however, previous studies in other cell lines also demonstrated MAPK-dependent induction of p21 expression (101, 103, 104).

NAG-1 and ATF3 are growth inhibitory and proapoptotic proteins (48, 49), and previous studies with PPARγ agonists report both receptor-dependent and -independent induction of NAG-1 (22, 94, 98, 99). Induction of NAG-1 and ATF3 by β-CDODA-Me in LNCaP cells was also PPARγ-independent. However, both PI3K and MAPK inhibitors blocked induction of NAG-1 and ATF-3; however, the JNK inhibitor SP600125 was the most potent inhibitor of ATF-3 (but not NAG-1) induction and this is consistent with previous studies showing that homocysteine also induces ATF3 in vascular cells through activation of JNK which activates c-jun and ATF-3 through an AP-1 site in the promoter (105). The kinase-dependent induction of NAG-1 has previously been reported and these effects are both structure and cell context-dependent. In the present study, the time-dependent induction of both EGR-1 and NAG-1 are similar in LNCaP cells, and inhibition of NAG-1 expression is observed with both PI3K and MAPK inhibitors.

Two recent reports show that in LNCaP cells AR knockdown by RNA interference results in apoptosis (93) and stable knockdown using short hairpin RNAs for AR results in decreased AR and PSA expression and inhibition of tumor growth in vivo (106). β-CDODA-Me decreases AR and PSA expression in LNCaP cells over a narrow range of concentrations (1-2.5 µM). Moreover, cycloheximide reversed the β-CDODA-Me-dependent downregulation of PSA but not AR mRNA levels. A recent report indicated that decreased AR expression in LNCaP cells treated with a PPARγ-inactive thiazolidinedione derivative was due to proteasome-dependent degradation of Sp1 (102) and the present results also show a parallel decrease in AR and Sp1 in LNCaP cells treated with β-CDODA-Me. However, in contrast to the previous report, this effect on AR was not reversed by a proteasome inhibitor. Moreover, results in FIG. 22D also show that 2.5 µM β-CDODA-Me rapidly induces PARP cleavage and apoptosis in LNCaP cells prior to decreased AR expression demonstrating that apoptotic pathways other than loss of AR are activated by β-CDODA-Me in LNCaP cells.

Results of the present study demonstrate that 2-substituted 1,2-dehydro 3-oxo GA analogs are potent inhibitors of LNCaP cell growth and induces proapoptotic responses through activation of kinases or affecting expression of other genes including NAG-1, ATF-3, AR and PSA. β-CDODA-Me's proapoptotic and growth inhibitory effects were PPARγ-independent.

Example 10

In Vivo Models

The compounds of the present invention decrease expression of Sp1, Sp3 and Sp3 in colon and pancreatic cancer cells. This correlates with the cytotoxicity, antiangiogenic and proapoptotic effects of these agents. Moreover, β-CDODA-Me is also a PPARγ agonist and at least in HCT-15 colon cancer cells, there is evidence that activation of this pathway is important for the observed anticancer activity. Therefore, the compounds of the present invention appear to inhibit growth of colon, pancreatic and prostate tumor growth through activation of PPARγ and/or degradation of Sp1, Sp3 and Sp4 in tumors. The anticancer activity and the tumor and tissue/cell specificity of Sp protein knockdown of the compounds of the invention can be further demonstrated in animal models.

The experimental design utilizes the athymic nude mouse xenograft and orthotopic models for prostate, colon and pancreatic cancer, the Min mouse model for colon cancer and the TRAMP model for prostate cancer. SW480, RKO, Panc1, PC3 and LNCaP cancer cells (xenograft) and L3.6pl pancreatic cancer cells (xenograft and orthotopic) are used in athymic nude mice and the antitumorigenic effects of the compounds of the invention are investigated. The Min mouse model for colon cancer and the TRAMP model for prostate cancer are used to assay the effects of the compounds of the invention on tumor formation and growth and the determination of selected proapoptotic/antiangiogenic markers are compared to those investigated in the xenografts/orthotopic experiments.

(a) Xenograph and Orthotopic Tumor Studies for Colon and Pancreatic Cancer (i) Animal treatment: Male athymic nude mice are obtained from commercial sources and their use approved by the Institutional Animal Care and Use Committee. The mice are housed under specific conditions and in facilities approved by the American Association for Accreditation of Laboratory Animal Care at LARR facilities in College Station, Tex., and the corresponding facilities at IBT in Houston, Tex. Ten animals are used for each treatment group. SW480, RKO and Panc1 cells are used in the xenograft study and L3.6pl pancreatic cancer cells are used in the orthotopic model as previously described (66, 67). Cells are harvested by exposure to trypsin and resuspended in serum-free Hanks' balanced salt solution (HBSS). Viability is assessed by trypan blue exclusion, and only single-cell suspensions exhibiting greater than 95% viability are used. For subcutaneous tumors, tumor cells ($1 \times 10^6$ cells) suspended in a volume of 200 µL are implanted subcutaneously in the flank of nude male animals using a 27-gauge needle. Tumors are allowed to grow unperturbed for 10-14 days and when palpable tumors (200 mm$^3$) first appear, mice are randomly assigned to treatment or control groups. Mice are treated (10 per treatment group) with placebo or a compound of the invention (2, 10, or 20 mg/kg/d) (in corn oil) administered every second day for 4 to 6 weeks (depending on appearance and size of control tumors). The doses of the compounds of the invention are estimated from relative potency data. A similar does regiment is used for the orthotopic model for pancreatic cancer using L3.6pl cells as previously described (86). Seven days after implantation of tumor cells into the pancreas of each mouse, 5 mice are sacrificed to confirm the presence of tumor lesions. Compounds are administered three times weekly (i.p. injection). Mice are sacrificed on day 35 and body weights, determined. Primary tumors in the pancreas are excised, measured and weighed. For IHC and H&E staining procedures, one part of the tumor tissue is fixed in formalin and embedded in paraffin, and another part is embedded in OCT compound, rapidly frozen in liquid nitrogen, and stored at −70° C. Visible liver metastases is counted with the aid of a dissecting microscope, and the tissues processed for H&E staining.

(ii) Immunohistochemical and Western blot analysis: Tumor sections from compound- and corn oil-treated animals are also prepared for in situ hybridization and immunohistochemical analysis of proteins and in situ hybridization (for mRNAs), including proapoptotic (survivin, PARP and caspase 3 cleavage) and angiogenic (VEGF, VEGFR1 and VEGFR2) genes/proteins or responses. In addition, immunostaining for Sp1, Sp3 and Sp4 is done and many of these responses have been determined in previous studies (66, 67, 69-72). In addition, Western blot analysis of Sp proteins, proapoptotic and antiangiogenic responses are determined on whole cell lysates from compound- and corn oil (vehicle)-treated tumors as previously described (66, 67). Where possible (depending on the amount of protein extracted), the effects of compound versus corn oil on expression of these proteins is quantitated and statistically analyzed. In addition, the effects of the compounds of the invention on Sp protein expression in non-target tissue (e.g. bone marrow, liver and kidney) is also determined. Activation of PPARγ-dependent genes/proteins such as caveolin-1 and KLF-4 is also determined by in situ hybridization/immunostaining and by Western blot analysis of tumor lysates.

(b) Min Mouse Model of Colon Cancer.

A recent study showed that relatively low doses of pioglitazone inhibited intestinal tumor formation in mice expressing an inactive truncated Apc gene (39). This antitumorigenic response for pioglitazone has now been observed in C57BL/6-Apc$^{Min/+}$ (Min mice) which are available from Jackson Laboratory (107). Therefore, Min mice are used to examine intestinal polyp formation and hyperlipidemia essentially as described in (107). Six-week old male Min mice are administered corn oil (control) and different doses of a compound of the invention. Doses of 2, 10 and 20 mg/kg in corn oil are administered orally by gavage every second day for 14 weeks. At least ten animals are used in each treatment group, and after the last dose, blood is taken and the following parameters determined in a diagnostic laboratory: AST, ALP, LDH, BUN, creatinine, triglycerides, glucose, and total protein. The suppression of lipid levels is a measure of the hyperlipidemic effects which are typically observed for PPARγ agonists. The intestines are dissected into proximal, middle and distal sections, and examined for polyp formation by a veterinary pathologist. In addition, expression of Sp proteins and Sp-dependent genes are determined in intestinal tissues/polyps to determine the role of Sp protein degradation in mediating the anticancer responses observed in the Min mouse model.

(c) Xenograft Studies for Prostate Cancer (i) Animal treatment: Male athymic nude mice are obtained from commercial sources and their use approved by the Institutional Animal Care and Use Committee. Ten animals are used for each treatment group and based on consultation with biostatisticians, this number is sufficient for determining statistical significance between treatment groups (41, 42). At least one AR-positive (LNCaP/22Rv1) and AR-negative (PC3/DU145) prostate cancer cell line is used in the xenograft study. Cells are harvested by exposure to trypsin and resuspended in serum-free Hanks' balanced salt solution (HBSS). Viability is assessed by trypan blue exclusion, and only single-cell suspensions exhibiting greater than 95% viability are used. Tumor cells ($1 \times 10^6$ cells) suspended in a volume of 200 µL are implanted subcutaneously in the flank of nude male animals using a 27-gauge needle. Tumors are allowed to grow unperturbed for 10-14 days and when palpable tumors (200 mm$^3$) first appear, mice are randomly assigned to treatment or control groups. Mice are treated (10 per treatment group) with placebo or a compound of the invention (2, 10, or 20 mg/kg/d) (in corn oil) administered every second day for 4 to 6 weeks (depending on appearance and size of control tumors).

(ii) Immunohistochemical and Western blot analysis: Tumor sections from compound- and corn oil-treated animals are also prepared for in situ hybridization and immunohistochemical analysis of proteins and in situ hybridization (for mRNAs), including proapoptotic (survivin, PARP and caspase 3 cleavage) and angiogenic (VEGF, VEGFR1 and VEGFR2) genes/proteins or responses. In addition, immunostaining for Sp1, Sp3 and Sp4, is done as previously described (41, 42). In addition, Western blot analysis of Sp proteins, proapoptotic and antiangiogenic responses is determined on whole cell lysates from compound- and corn oil (vehicle)-treated tumors. Where possible (depending on the amount of protein extracted), the effects of the compound versus corn oil on expression of these proteins is quantitated and statistically analyzed. In addition, the effects of the compound on Sp protein expression in non-target tissue (e.g. liver and kidney) is determined. Preliminary results indicate that Sp1, Sp3 and Sp4 are minimally expressed in liver and are unaffected by β-CDODA-Me/β-IDODA-Me.

(d) TRAMP Mouse Model (i) Animal treatment: The TRAMP mouse model is ideal for testing the antitumorigenic activity of the compounds of the invention. Compounds in corn oil are administered every second day from the age of 16 weeks until they are 28 weeks of age when TRAMP mice exhibit approximately 100% primary prostate tumors and metastases.

(ii) Prostate tumor formation and metastasis: Treated and control (corn oil) TRAMP mice are sacrificed at 28 weeks of age and prostate tumor weights, and other organ and whole body weights are recorded; lymph nodes, lung, kidney and adrenal glands are examined histopathologically for tumor metastasis and the prostate tumor grade is also assessed.

(iii) Immunohistochemical and Western blot analysis: Tumor sections from the treated and untreated TRAMP mice are prepared for immunohistochemical analysis, and whole cell lysates from tumor sections are also obtained for Western blot analysis. Immunostaining for Sp1, Sp3 and Sp4 and for angiogenic (VEGF, VEGFR1 and VEGFR2) and apoptotic (cleaved PARP, activated caspase 3, survivin and TUNEL) proteins/responses are determined as described above.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE SPECIFICATION

1. Armanini D, Fiore C, Mattarello M J, Bielenberg J and Palermo M (2002) History of the endocrine effects of licorice. *Exp Clin Endocrinol Diabetes* 110:257-261.
2. Thyagarajan S, Jayaram S, Gopalakrishnan V, Hari R, Jeyakumar P and Sripathi M (2002) Herbal medicines for liver diseases in India. *J Gastroenterol Hepatol* 17 Suppl 3:S370-S376.
3. Armanini D, Fiore C, Bielenberg J and Ragazzi E (2005a) Licorice (*Glycyrrhiza glabra*), in *Encyclopedia of Dietary Supplements*, (Coates P ed) pp 371-399, Marcel Dekker, New York.
4. Fiore C, Eisenhut M, Ragazzi E, Zanchin G and Armanini D (2005) A history of the therapeutic use of liquorice in Europe. *J Ethnopharmacol* 99:317-324.
5. Whorwood C B, Sheppard M C and Stewart P M (1993) Licorice inhibits 11b-hydroxysteroid dehydrogenase messenger ribonucleic acid levels and potentiates glucocorticoid hormone action. *Endocrinology* 132:2287-2292.
6. Horigome H, Homma M, Hirano T and Oka K (2001) Glycyrrhetinic acid induced apoptosis in murine splenocytes. *Biol Pharm Bull* 24:54-58.
7. Horigome H, Horigome A, Homma M, Hirano T and Oka K (1999) Glycyrrhetinic acid-induced apoptosis in thymocytes: impact of 11b-hydroxysteroid dehydrogenase inhibition. *Am J Physiol* 277:E624-E630.
8. Armanini D, De Palo C B, Mattarello M J, Spinella P, Zaccaria M, Ermolao A, Palermo M, Fiore C, Sartorato P, Francini-Pesenti F and Karbowiak I (2003) Effect of licorice on the reduction of body fat mass in healthy subjects. *J Endocrinol Invest* 26:646-650.
9. Armanini D, Nacamulli D, Francini-Pesenti F, Battagin G, Ragazzi E and Fiore C (2005b) Glycyrrhetinic acid, the active principle of licorice, can reduce the thickness of subcutaneous thigh fat through topical application. *Steroids* 70:538-542.
10. Salvi M, Fiore C, Armanini D and Toninello A (2003) Glycyrrhetinic acid-induced permeability transition in rat liver mitochondria. *Biochem Pharmacol* 66:2375-2379.
11. Fiore C, Salvi M, Palermo M, Sinigaglia G, Armanini D and Toninello A (2004) On the mechanism of mitochondrial permeability transition induction by glycyrrhetinic acid. *Biochim Biophys Acta* 1658:195-201.
12. Salvi M, Fiore C, Battaglia V, Palermo M, Armanini D and Toninello A (2005) Carbenoxolone induces oxidative stress in liver mitochondria, which is responsible for transition pore opening. *Endocrinology* 146:2306-2312.
13. Baltina L A (2003) Chemical modification of glycyrrhizic acid as a route to new bioactive compounds for medicine. *Curr Med Chem* 10:155-171.
14. Ablise M, Leininger-Muller B, Wong C D, Siest G, Loppinet V and Visvikis S (2004) Synthesis and in vitro antioxidant activity of glycyrrhetinic acid derivatives tested with the cytochrome P450/NADPH system. *Chem Pharm Bull* (Tokyo) 52:1436-1439.
15. Honda T, Finlay H J, Gribble G W, Suh N and Sporn M B (1997) New enone derivatives of oleanolic acid and ursolic acid as inhibitors of nitric oxide production in mouse macrophages. *Bioorg Med Chem Lett* 7:1623-1628.
16. Honda T, Gribble G W, Suh N, Finlay H J, Rounds B V, Bore L, Favaloro F G, Jr., Wang Y and Sporn M B (2000) Novel synthetic oleanane and ursane triterpenoids with various enone functionalities in ring A as inhibitors of nitric oxide production in mouse macrophages. *J Med Chem* 43:1866-1877.
17. Honda T, Rounds B V, Gribble G W, Suh N, Wang Y and Sporn M B (1998) Design and synthesis of 2-cyano-3,12-dioxoolean-1,9-dien-28-oic acid, a novel and highly active inhibitor of nitric oxide production in mouse macrophages. *Bioorg Med Chem Lett* 8:2711-2714.
18. Couch R D, Browning R G, Honda T, Gribble G W, Wright D L, Sporn M B and Anderson A C (2005) Studies on the reactivity of CDDO, a promising new chemopreventive and chemotherapeutic agent: implications for a molecular mechanism of action. *Bioorg Med Chem Lett* 15:2215-2219.
19. Dinkova-Kostova A T, Liby K T, Stephenson K K, Holtzclaw W D, Gao X, Suh N, Williams C, Risingsong R, Honda T, Gribble G W, Sporn M B and Talalay P (2005) Extremely potent triterpenoid inducers of the phase 2 response: correlations of protection against oxidant and inflammatory stress. *Proc Natl Acad Sci USA* 102:4584-4589.
20. Wang Y, Porter W W, Suh N, Honda T, Gribble G W, Leesnitzer L M, Plunket K D, Mangelsdorf D J, Blanchard S G, Willson T M and Sporn M B (2000) A synthetic triterpenoid, 2-cyano-3,12-dioxooleana-1,9-dien-28-oic acid (CDDO), is a ligand for the peroxisome proliferator-activated receptor g. *Mol Endocrinol* 14:1550-1556.
21. Lapillonne H, Konopleva M, Tsao T, Gold D, McQueen T, Sutherland R L, Madden T and Andreeff M (2003) Activation of peroxisome proliferator-activated receptor g by a novel synthetic triterpenoid 2-cyano-3,12-dioxooleana-1, 9-dien-28-oic acid induces growth arrest and apoptosis in breast cancer cells. *Cancer Res* 63:5926-5939.

22. Chintharlapalli S, Papineni S, Konopleva M, Andreef M, Samudio I and Safe S (2005) 2-Cyano-3,12-dioxoolean-1,9-dien-28-oic acid and related compounds inhibit growth of colon cancer cells through peroxisome proliferator-activated receptor g-dependent and -independent pathways. *Mol Pharmacol* 68:119-128.

23. Lee, C. H., Olson, P. and Evans, R. M. Minireview: lipid metabolism, metabolic diseases, and peroxisome proliferator-activated receptors. *Endocrinology* 144:2201-2207, 2003.

24. Desvergne, B., Michalik, L. and Wahli, W. Be fit or be sick: peroxisome proliferator-activated receptors are down the road. *Mol. Endocrinol.* 18:1321-1332, 2004.

25. Barish, G. D. and Evans, R. M. PPARs and LXRs: atherosclerosis goes nuclear. *Trends Endocrinol. Metab* 15:158-165, 2004.

26. Lazar, M. A. PPAR gamma, 10 years later. *Biochimie* 87:9-13, 2005.

27. Grommes, C., Landreth, G. E. and Heneka, M. T. Antineoplastic effects of peroxisome proliferator-activated receptor g agonists. *Lancet Oncol.* 5:419-429, 2004.

28. Ikezoe, T., Miller, C. W., Kawano, S., Heaney, A., Williamson, E. A., Hisatake, J., Green, E., Hofmann, W., Taguchi, H. and Koeffler, H. P. Mutational analysis of the peroxisome proliferator-activated receptor g gene in human malignancies. *Cancer Res.* 61:5307-5310, 2001.

29. Gupta, R. A., Brockman, J. A., Sarraf, P., Willson, T. M. and DuBois, R. N. Target genes of peroxisome proliferator-activated receptor g in colorectal cancer cells. *J. Biol. Chem.* 276:29681-29687, 2001.

30. Itami, A., Watanabe, G., Shimada, Y., Hashimoto, Y., Kawamura, J., Kato, M., Hosotani, R. and Imamura, M. Ligands for peroxisome proliferator-activated receptor g inhibit growth of pancreatic cancers both in vitro and in vivo. *Int. J. Cancer* 94:370-376, 2001.

31. Motomura, W., Okumura, T., Takahashi, N., Obara, T. and Kohgo, Y. Activation of peroxisome proliferator-activated receptor gamma by troglitazone inhibits cell growth through the increase of $p27^{KiP1}$ in human pancreatic carcinoma cells. *Cancer Res.* 60:5558-5564, 2000.

32. Wächtershäuser, A., Loitsch, S. M. and Stein, J. PPAR-g is selectively upregulated in Caco-2 cells by butyrate. *Biochem. Biophys. Res. Commun.* 272:380-385, 2000.

33. Elnemr, A., Ohta, T., Iwata, K., Ninomia, I., Fushida, S., Nishimura, G., Kitagawa, H., Kayahara, M., Yamamoto, M., Terada, T. and Miwa, K. PPARg ligand (thiazolidinedione) induces growth arrest and differentiation markers of human pancreatic cancer cells. *Int. J. Oncol.* 17:1157-1164, 2000.

34. Kitamura, S., Miyazaki, Y., Shinomura, Y., Kondo, S., Kanayama, S. and Matsuzawa, Y. Peroxisome proliferator-activated receptor g induces growth arrest and differentiation markers of human colon cancer cells. *Jpn. J. Cancer Res.* 90:75-80, 1999.

35. Brockman, J. A., Gupta, R. A. and DuBois, R. N. Activation of PPARg leads to inhibition of anchorage independent growth of human colorectal cancer cells. *Gastroenterology* 115:1049-1055, 1998.

36. Ohta, T., Elnemr, A., Yamamoto, M., Ninomiya, I., Fushida, S., Nishimura, G., Fujimura, T., Kitagawa, H., Kayahara, M., Shimizu, K., Yi, S. and Miwa, K. Thiazolidinedione, a peroxisome proliferator-activated receptor-g ligand, modulates the E-cadherin/b-catenin system in a human pancreatic cancer cell line, BxPC-3. *Int. J. Oncol.* 21:37-42, 2002.

37. Motomura, W., Tanno, S., Takahashi, N., Nagamine, M., Fukuda, M., Kohgo, Y. and Okumura, T. Involvement of MEK-ERK signaling pathway in the inhibition of cell growth by troglitazone in human pancreatic cancer cells. *Biochem. Biophys. Res. Commun.* 332:89-94, 2005.

38. Hashimoto, K., Farrow, B. J. and Evers, B. M. Activation and role of MAP kinases in 15d-PGJ2-induced apoptosis in the human pancreatic cancer cell line MIA PaCa-2. *Pancreas* 28:153-159, 2004.

39. Niho, N., Takahashi, M., Kitamura, T., Shoji, Y., Itoh, M., Noda, T., Sugimura, T. and Wakabayashi, K. Concomitant suppression of hyperlipidemia and intestinal polyp formation in Apc-deficient mice by peroxisome proliferator-activated receptor ligands. *Cancer Res.* 63:6090-6095, 2003.

40. Girnun, G. D., Smith, W. M., Drori, S., Sarraf, P., Mueller, E., Eng, C., Nambiar, P., Rosenberg, D. W., Bronson, R. T., Edelmann, W., Kucherlapati, R., Gonzalez, F. J. and Spiegelman, B. M. APC-dependent suppression of colon carcinogenesis by PPARg. *Proc. Natl. Acad. Sci. U.S.A.* 99:13771-13776, 2002.

41. Osawa, E., Nakajima, A., Wada, K., Ishimine, S., Fujisawa, N., Kawamori, T., Matsuhashi, N., Kadowaki, T., Ochiai, M., Sekihara, H. and Nakagama, H. Peroxisome proliferator-activated receptor g ligands suppress colon carcinogenesis induced by azoxymethane in mice. *Gastroenterology* 124:361-367, 2003.

42. Tanaka, T., Kohno, H., Yoshitani, S., Takashima, S., Okumura, A., Murakami, A. and Hosokawa, M. Ligands for peroxisome proliferator-activated receptors a and g inhibit chemically induced colitis and formation of aberrant crypt foci in rats. *Cancer Res.* 61:2424-2428, 2001.

43. Kohno, H., Yoshitani, S., Takashima, S., Okumura, A., Hosokawa, M., Yamaguchi, N. and Tanaka, T. Troglitazone, a ligand for peroxisome proliferator-activated receptor g, inhibits chemically-induced aberrant crypt foci in rats. *Jpn. J. Cancer Res.* 92:396-403, 2001.

44. Abdelrahim, M., Newman, K., Vanderlaag, K., Samudio, I. and Safe, S. 3,3'-Diindolylmethane (DIM) and derivatives induce apoptosis in pancreatic cancer cells through endoplasmic reticulum stress-dependent upregulation of DR5. *Carcinogenesis* 27:717-728, 2006.

45. Hong, J., Samudio, I., Liu, S., Abdelrahim, M. and Safe, S. Peroxisome proliferator-activated receptor g-dependent activation of p21 in Panc-28 pancreatic cancer cells involves Sp1 and Sp4 proteins. *Endocrinology* 145:5774-5785, 2004.

46. Samudio, I., Konopleva, M., Hail, N., Jr., Shi, Y. X., McQueen, T., Hsu, T., Evans, R., Honda, T., Gribble, G. W., Sporn, M., Gilbert, H. F., Safe, S. and Andreeff, M. 2-Cyano-3,12 dioxooleana-1,9 diene-28-imidazolide (CDDO-lm) directly targets mitochondrial glutathione to induce apoptosis in pancreatic cancer. *J. Biol. Chem.* 280:36273-36282, 2005.

47. Chintharlapalli, S., Papineni, S., Baek, S. J., Liu, S. and Safe, S. 1,1-Bis(3'-indolyl)-1-(p-substitutedphenyl)methanes are peroxisome proliferator-activated receptor gamma agonists but decrease HCT-116 colon cancer cell survival through receptor-independent activation of early growth response-1 and NAG-1. *Mol. Pharmacol.* 68:1782-1792, 2005.

48. Chintharlapalli, S., Papineni, S., Konopleva, M., Andreef, M., Samudio, I. and Safe, S. 2-Cyano-3,12-dioxoolean-1,9-dien-28-oic acid and related compounds inhibit growth of colon cancer cells through peroxisome proliferator-activated receptor g-dependent and -independent pathways. *Mol. Pharmacol.* 68:119-128, 2005.

49. Chintharlapalli, S., Papineni, S. and Safe, S. 1,1-Bis(3'-indolyl)-1-(p-substituted phenyl)methanes inhibit colon cancer cell and tumor growth through PPARg-dependent and PPARg-independent pathways. *Mol. Cancer. Ther.* 5:1362-1370, 2006.

50. Chintharlapalli, S., Smith III, R., Samudio, I., Zhang, W. and Safe, S. 1,1-Bis(3'-indolyl)-1-(p-substitutedphenyl)methanes induce peroxisome proliferator-activated receptor g-mediated growth inhibition, transactivation and differentiation markers in colon cancer cells. *Cancer Res.* 64:5994-6001, 2004.

51. Dynan, W. S. and Tjian, R. The promoter-specific transcription factor Sp1 binds to upstream sequences in the SV40 early promoter. *Cell* 35:79-87, 1983.

52. Philipsen, S. and Suske, G. A tale of three fingers: the family of mammalian Sp/XKLF transcription factors. *Nucleic Acids Res.* 27:2991-3000, 1999.

53. Black, A. R., Black, J. D. and Azizkhan-Clifford, J. Sp1 and Krüppel-like factor family of transcription factors in cell growth regulation and cancer. *J. Cell. Physiol.* 188:143-160, 2001.

54. Suske, G. The Sp-family of transcription factors. *Gene* 238:291-300, 1999.

55. Suske, G., Bruford, E. and Philipsen, S. Mammalian SP/KLF transcription factors: bring in the family. *Genomics* 85:551-556, 2005.

56. Safe, S. and Abdelrahim, M. Sp transcription factor family and its role in cancer. *Eur. J. Cancer* 41:2438-2448, 2005.

57. Marin, M., Karis, A., Visser, P., Grosveld, F. and Phillipsen, S. Transcription factor Sp1 is essential for early embryonic development but dispensable for cell growth and differentiation. *Cell* 89:619-628, 1997.

58. Bouwman, P., Gollner, H., Elsasser, H.-P., Eckhoff, G., Karis, A., Grosveld, F., Philipsen, S. and Suske, G. Transcription factor Sp3 is essential for post-natal survival and late tooth development. *EMBO J.* 19:655-661, 2000.

59. Gollner, H., Dani, C., Phillips, B., Philipsen, S. and Suske, G. Impaired ossification in mice lacking the transcription factor Sp3. *Mech. Dev.* 106:77-83, 2001.

60. Wang, L., Wei, D., Huang, S., Peng, Z., Le, X., Wu, T. T., Yao, J., Ajani, J. and Xie, K. Transcription factor Sp1 expression is a significant predictor of survival in human gastric cancer. *Clin. Cancer Res.* 9:6371-6380, 2003.

61. Yao, J. C., Wang, L., Wei, D., Gong, W., Hassan, M., Wu, T. T., Mansfield, P., Ajani, J. and Xie, K. Association between expression of transcription factor Sp1 and increased vascular endothelial growth factor expression, advanced stage, and poor survival in patients with resected gastric cancer. *Clin. Cancer Res.* 10:4109-4117, 2004.

62. Shi, Q., Le, X., Abbruzzese, J. L., Peng, Z., Qian, C. N., Tang, H., Xiong, Q., Wang, B., Li, X. C. and Xie, K. Constitutive Sp1 activity is essential for differential constitutive expression of vascular endothelial growth factor in human pancreatic adenocarcinoma. *Cancer Res.* 61:4143-4154, 2001.

63. Zannetti, A., Del, V. S., Carriero, M. V., Fonti, R., Franco, P., Botti, G., D'Aiuto, G., Stoppelli, M. P. and Salvatore, M. Coordinate up-regulation of Sp1 DNA-binding activity and urokinase receptor expression in breast carcinoma. *Cancer Res.* 60:1546-1551, 2000.

64. Chiefari, E., Brunetti, A., Arturi, F., Bidart, J. M., Russo, D., Schlumberger, M. and Filetti, S. Increased expression of AP2 and Sp1 transcription factors in human thyroid tumors: a role in NIS expression regulation? *BMC. Cancer* 2:352002.

65. Hosoi, Y., Watanabe, T., Nakagawa, K., Matsumoto, Y., Enomoto, A., Morita, A., Nagawa, H. and Suzuki, N. Up-regulation of DNA-dependent protein kinase activity and Sp1 in colorectal cancer. *Int. J. Oncol.* 25:461-468, 2004.

66. Abdelrahim, M., Baker, C. H., Abbruzzese, J. L. and Safe, S. Tolfenamic acid and pancreatic cancer growth, angiogenesis, and Sp protein degradation. *J. Natl. Cancer Inst.* 98:855-868, 2006.

67. Chintharlapalli, S., Papineni, S., Ramaiah, S. K. and Safe, S. Betulinic acid inhibits prostate cancer growth through inhibition of specificity protein transcription factors. *Cancer Res.* in press, 2007.

68. Lou, Z., O'Reilly, S., Liang, H., Maher, V. M., Sleight, S. D. and Mccormick, J. J. Down-regulation of overexpressed Sp1 protein in human fibrosarcoma cell lines inhibits tumor formation. *Cancer Res.* 65:1007-1017, 2005.

69. Abdelrahim, M. and Safe, S. Cyclooxygenase-2 inhibitors decrease vascular endothelial growth factor expression in colon cancer cells by enhanced degradation of Sp1 and Sp4 proteins. *Mol. Pharmacol.* 68:317-329, 2005.

70. Higgins, K. J., Abdelrahim, M., Liu, S., Yoon, K. and Safe, S. Regulation of vascular endothelial growth factor receptor-2 expression in pancreatic cancer cells by Sp proteins. *Biochem. Biophys. Res. Commun.* 345:292-301, 2006.

71. Abdelrahim, M., Smith III, R., Burghardt, R. and Safe, S. Role of Sp proteins in regulation of vascular endothelial growth factor expression and proliferation of pancreatic cancer cells. *Cancer Res.* 64:6740-6749, 2004.

72. Abdelrahim, M., Baker, C. H., Abbruzzese, J. L., Sheikh-Hamad, D., Liu, S., Cho, S. D., Yoon, K. and Safe, S. Regulation of vascular endothelial growth factor receptor-1 (VEGFR1) expression by specificity proteins 1, 3 and 4 in pancreatic cancer cells. *Cancer Res.* in revision, 2007.

73. Wei, D., Wang, L., He, Y., Xiong, H. Q., Abbruzzese, J. L. and Xie, K. Celecoxib inhibits vascular endothelial growth factor expression in and reduces angiogenesis and metastasis of human pancreatic cancer via suppression of Sp1 transcription factor activity. *Cancer Res.* 64:2030-2038, 2004.

74. K. C. Nicolaou, T. Montagnon, P. S. Baran and Y.-L. Zhong, *J. Am. Chem. Soc.*, 2002, 124, 2245-2258.

75. Neumann H C (1980) Pharmaceutical compositions containing polycyclic cyanoketones. Application No. EP19790103739. Patent No. EP0009801. International Classification C07D261/20.

76. Bender F C, Reymond M A, Bron C and Quest A F, (2000), Caveolin-1 levels are down-regulated in human colon tumors, and ectopic expression of caveolin-1 in colon carcinoma cell lines reduces cell tumorigenicity. *Cancer Res,* 60:5870-5878.

77. Burgermeister E, Tencer L and Liscovitch M, (2003), Peroxisome proliferator-activated receptor-γ upregulates caveolin-1 and caveolin-2 expression in human carcinoma cells. *Oncogene,* 22:3888-3900.

78. Desvergne B and Wahli W, (1999), Peroxisome proliferator-activated receptors: nuclear control of metabolism, *Endocr. Rev.* 20:649-688.

79. Escher P and Wahli W, (2000), Peroxisome proliferator-activated receptors: insight into multiple cellular functions. *Mutat Res,* 448:121-138.

80. Smith, C L, O'Malley, B W, (2004), Coregulator function: A key to understanding tissue specificity of selected receptor modulators. *Endocr. Rev.* 25:45-71.

81. Katzenellenbogen J A, O'Malley B W and Katzenellenbogen B S, (1996), Tripartite steroid hormone receptor pharmacology—interaction with multiple effector sites as a basis for the cell- and promoter-specific action of these hormones. *Endocrinol*, 10:119-131.

82. Baek S J, Wilson L C and Eling T E, (2003), Troglitazone, a peroxisome proliferator-activated receptor γ (PPARγ) ligand, selectively induces the early growth response-1 gene independently of PPARγ. A novel mechanism for its anti-tumorigenic activity. *J Biol Chem*, 278:5845-5853.

83. Baek S J, Kim J S, Nixon J B, DiAugustine R P and Eling T E, (2004), Expression of NAG-1, a transforming growth factor-β superfamily member, by troglitazone requires the early growth response gene EGR-1. *J Biol Chem*, 279: 6883-6892.

84. Kodera Y, Takeyama K, Murayama A, Suzawa M, Masuhiro Y and Kato S, (2000), Ligand type-specific interactions of peroxisome proliferator-activated receptor γ with transcriptional coactivators. *J Biol Chem*, 275:33201-33204.

85. Chintharlapalli S, Smith III R, Samudio I, Zhang W and Safe S, (2004), 1,1-Bis(3'-indolyl)-1-(p-substituedphenyl) methanes induce peroxisome proliferator-activated receptor γ-mediated growth inhibition, transactiviation and differentiation markers in colon cancer cells. *Cancer Res*, 64:5994-6001.

86. Samudio I, Konopleva M, Hail N, Jr, Shi Y X, McQueen T, Hsu T, Evans R, Honda T, Gribble G W, Sporn M, Gilbert H F, Safe S and Andreeff M, (2005), 2-Cyano-3,12 dioxoolean-1,9 diene-28-imidazolide (CDDO-lm) directly targets mitochondrial glutathione to induce apoptosis in pancreatic cancer. *J Biol Chem*, 280:36273-36282

87. Konopleva M, Elstner E, McQueen T J, Tsao T, Sudarikov A, Hu W, Schober W D, Wang R Y, Chism D, Kornblau S M, Younes A, Collins S J, Koeffler H P and Andreeff M, (2004), Peroxisome proliferator-activated receptor γ and retinoid X receptor ligands are potent inducers of differentiation and apoptosis in leukemias. *Mol. Cancer. Ther,* 3:1249-1262.

88. Ito Y, Pandey P, Place A, Sporn M B, Gribble G W, Honda T, Kharbanda S and Kufe D, (2000), The novel triterpenoid 2-cyano-3,12-dioxoolean-1,9-dien-28-oic acid induces apoptosis of human myeloid leukaemia cells by a caspase-8-dependent mechanism. *Cell Growth Differ,* 11:261-267.

89. Chen Z Y and Tseng C C, (2005), 15-deoxy-$\Delta^{12,14}$ prostaglandin $J_2$ up-regulates Krüppel-like factor 4 expression independently of peroxisome proliferator-activated receptor γ by activating the mitogen-activated protein kinase kinase/extracellular signal-regulated kinase signal transduction pathway in HT-29 colon cancer cells. *Mol Pharmacol,* 68:1203-1213.

90. Chintharlapalli S, Papineni S, Jutooru I, McAlees A, Safe S. Structure-dependent activity of glycyrrhetinic acid derivatives as peroxisome proliferator-activated receptor g (PPARg) agonists in colon cancer cells. Mol Cancer Therap 2007; In Press.

91. Chintharlapalli S, Papineni S, Safe S H. 1,1-Bis(3'-indolyl)-1-(p-substitutedphenyl)methanes inhibit growth, induce apoptosis, and decrease the androgen receptor in LNCaP prostate cancer cells through PPARg-independent pathways. Mol Pharmacol 2007; 71:558-69.

92. Yang C C, Ku C Y, Wei S, et al. Peroxisome proliferator-activated receptor g-independent repression of prostate-specific antigen expression by thiazolidinediones in prostate cancer cells. Mol Pharmacol 2006; 69:1564-70.

93. Liao X, Tang S, Thrasher J B, Griebling T L, Li B. Small-interfering RNA-induced androgen receptor silencing leads to apoptotic cell death in prostate cancer. Mol Cancer Ther 2005; 4:505-15.

94. Chintharlapalli S, Papineni S, Baek S J, Liu S, Safe S. 1,1-Bis(3'-indolyl)-1-(p-substitutedphenyl)methanes are peroxisome proliferator-activated receptor gamma agonists but decrease HCT-116 colon cancer cell survival through receptor-independent activation of early growth response-1 and NAG-1. Mol Pharmacol 2005; 68:1782-92.

95. Chintharlapalli S, Smith III R, Samudio I, Zhang W, Safe S. 1,1-Bis(3'-indolyl)-1-(p-substitutedphenyl)methanes induce peroxisome proliferator-activated receptor g-mediated growth inhibition, transactivation and differentiation markers in colon cancer cells. Cancer Res 2004; 64:5994-6001.

96. Chintharlapalli S, Papineni S, Safe S. 1,1-Bis(3'-indolyl)-1-(p-substituted phenyl)methanes inhibit colon cancer cell and tumor growth through PPARg-dependent and PPARg-independent pathways. Mol Cancer Ther 2006; 5:1362-70.

97. Lei P, Abdelrahim M, Safe S. 1,1-Bis(3'-indolyl)-1-(p-substituted phenyl)methanes inhibit ovarian cancer cell growth through peroxisome proliferator-activated receptor-dependent and independent pathways. Mol Cancer Ther 2006; 5:2324-36.

98. Baek S J, Kim J S, Nixon J B, DiAugustine R P, Eling T E. Expression of NAG-1, a transforming growth factor-b superfamily member, by troglitazone requires the early growth response gene EGR-1. J Biol Chem 2004; 279: 6883-92.

99. Baek S J, Wilson L C, Hsi L C, Eling T E. Troglitazone, a peroxisome proliferator-activated receptor g (PPARg) ligand, selectively induces the early growth response-1 gene independently of PPARg. A novel mechanism for its anti-tumorigenic activity. J Biol Chem 2003; 278:5845-53.

100. Baek S J, Kim J S, Moore S M, Lee S H, Martinez J, Eling T E. Cyclooxygenase inhibitors induce the expression of the tumor suppressor gene EGR-1, which results in the up-regulation of NAG-1, an antitumorigenic protein. Mol Pharmacol 2005; 67:356-64.

101. Ciccarelli C, Marampon F, Scoglio A, et al. $p21^{WAF1}$ expression induced by MEK/ERK pathway activation or inhibition correlates with growth arrest, myogenic differentiation and onco-phenotype reversal in rhabdomyosarcoma cells. Mol Cancer 2005; 4:41.

102. Yang C C, Wang Y C, Wei S, et al. Peroxisome proliferator-activated receptor gamma-independent suppression of androgen receptor expression by troglitazone mechanism and pharmacologic exploitation. Cancer Res 2007; 67:3229-38.

103. Facchinetti M M, De S A, Toskos D, Senderowicz A M. UCN-01-induced cell cycle arrest requires the transcriptional induction of $p21^{waf1/cip1}$ by activation of mitogen-activated protein/extracellular signal-regulated kinase kinase/extracellular signal-regulated kinase pathway. Cancer Res 2004; 64:3629-37.

104. De Siervi A., Marinissen M, Diggs J, Wang X F, Pages G, Senderowicz A. Transcriptional activation of $p21^{waf1/cip1}$ by alkylphospholipids: role of the mitogen-activated protein kinase pathway in the transactivation of the human $p21^{waf1/cip1}$ promoter by Sp1. Cancer Res 2004; 64:743-50.

105. Cheng H, Snoek R, Ghaidi F, Cox M E, Rennie P S. Short hairpin RNA knockdown of the androgen receptor attenuates ligand-independent activation and delays tumor progression. Cancer Res 2006; 66:10613-20.

106. Cai Y, Zhang C, Nawa T, et al. Homocysteine-responsive ATF3 gene expression in human vascular endothelial cells: activation of c-Jun $NH_2$-terminal kinase and promoter response element. Blood 2000; 96:2140-8.

107. Niho, N., Takahashi, M., Shoji, Y., Takeuchi, Y., Matsubara, S., Sugimura, T. and Wakabayashi, K. Dose-dependent suppression of hyperlipidemia and intestinal polyp formation in Min mice by pioglitazone, a PPARg ligand. *Cancer Sci.* 94:960-964, 2003.

We claim:
1. A compound selected from a compound of Formula (I):

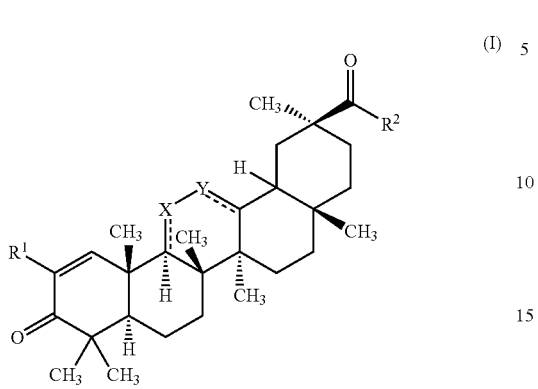

wherein
- $R^1$ is selected from CN, halo, $NO_2$, $CO_2R^3$, $C_{1-6}$alkyl, fluoro-substituted $C_{1-6}$alkyl, $C_{2-6}$alkenyl, $C_{2-6}$alkynyl, $OR^3$, $SR^3$, $SOR^3$, $SO_2R^3$, $NR^3R^4$, $C(O)NR^3R^4$, $C(O)R^3$, $OC(O)R^3$, $NHC(O)R^3$, $P(O)R^3R^4$, —C≡C—$R^3$, —$CR^3$=$CR^4R^5$, aryl and heteroaryl;
- $R^2$ is selected from $OC_{1-6}$alkyl, fluoro-substituted $OC_{1-6}$alkyl, $NH_2$, $NHC_{1-6}$alkyl, $N(C_{1-6}$alkyl)$(C_{1-6}$alkyl), SH and $SC_{1-6}$alkyl;
- $R^3$, $R^4$ and $R^5$ are independently selected from H, $C_{1-6}$alkyl, fluoro-substituted $C_{1-6}$alkyl, aryl and heteroaryl; and
- one of X and Y is C=O while the other is $CH_2$, and if X is C=O then - - - adjacent to X represents a single bond and - - - adjacent to Y represents a double bond and if Y is C=O then - - - adjacent to Y represents a single bond and - - - adjacent to X represents a double bond;

and pharmaceutically acceptable salts and solvates thereof, and mixtures thereof in any ratio,
with the proviso that $R^1$ is not —OH or —$OCH_3$.

2. The compound according to claim 1, wherein $R^1$ is selected from CN, halo, $NO_2$, $CO_2H$, $CO_2C_{1-4}$alkyl, $C_{1-4}$alkyl, fluoro-substituted $C_{1-4}$alkyl, $C_{2-4}$alkenyl, $C_{2-4}$alkynyl, $OC_{1-4}$alkyl, fluoro-substituted $OC_{1-4}$alkyl, OH, SH, $SC_{1-4}$alkyl, $SOC_{1-4}$alkyl, $SO_2C_{1-4}$alkyl, $NH_2$, $NHC_{1-4}$alkyl, $N(C_{1-4}$alkyl)$(C_{1-4}$alkyl), $C(O)NH_2$, $C(O)NHC_{1-4}$alkyl, $C(O)N(C_{1-4}$alkyl)$(C_{1-4}$alkyl), $C(O)C_{1-4}$alkyl, $OC(O)C_{1-4}$alkyl and $NHC(O)C_{1-4}$alkyl.

3. The compound according to claim 2, wherein $R^1$ is selected from CN, halo, $CO_2H$, $CO_2C_{1-4}$alkyl, $C_{1-4}$alkyl, fluoro-substituted $C_{1-4}$alkyl, $OC_{1-4}$alkyl, fluoro-substituted $OC_{1-4}$alkyl and OH.

4. The compound according to claim 3, wherein $R^1$ is selected from CN, Cl, Br, I, F, $CO_2H$, $CO_2CH_3$, $CH_3$, $CF_3$, $OCH_3$, $OCF_3$ and OH.

5. The compound according to claim 4, wherein $R^1$ is CN, $CF_3$ or I.

6. The compound according to claim 1, wherein $R^2$ is selected from $OC_{1-4}$alkyl, fluoro-substituted $OC_{1-4}$alkyl, $NH_2$, $NHC_{1-4}$alkyl, $N(C_{1-4}$alkyl)$(C_{1-4}$alkyl), SH and $SC_{1-4}$alkyl.

7. The compound according to claim 6, wherein $R^2$ is selected from $OC_{1-4}$alkyl and fluoro-substituted $OC_{1-4}$alkyl.

8. The compound according to claim 7, wherein $R^2$ is selected from $OCH_2CH_3$, $OCH_3$ and $OCF_3$.

9. The compound according to claim 8, wherein $R^2$ is $OCH_3$.

10. The compound according to claim 1, wherein X is C=O, Y is $CH_2$, - - - adjacent to X represents a single bond and - - - adjacent to Y represents a double bond to provide a compound of the formula:

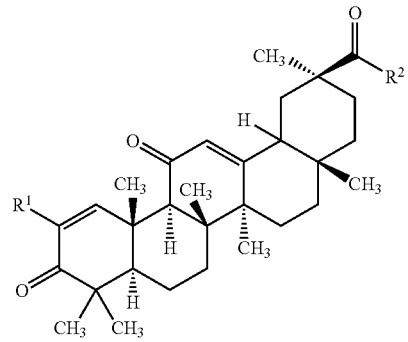

wherein $R^1$ and $R^2$ are as defined in claim 1, and pharmaceutically acceptable salts and solvates thereof.

11. A compound selected from a compound of the Formula 18α and 18β:

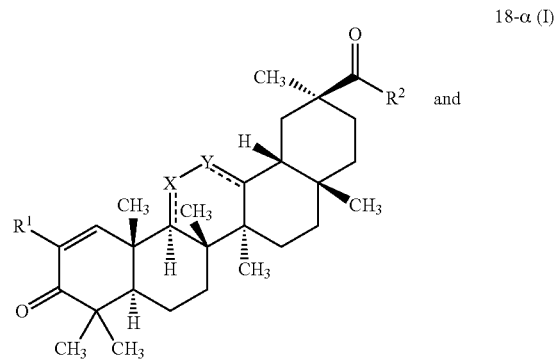

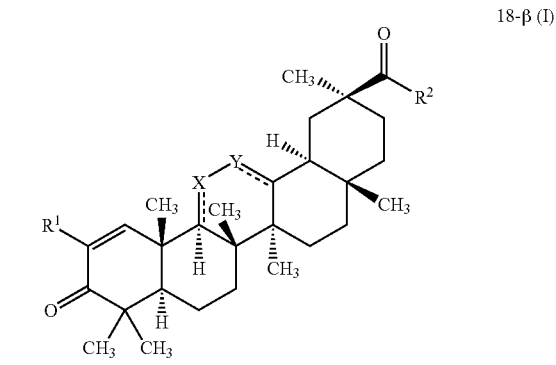

wherein $R^1$, $R^2$, X and Y are as defined in claim 1, and pharmaceutically acceptable salts and solvates thereof, and mixtures thereof in any ratio, with the proviso that $R^1$ is not —OH or —$OCH_3$.

12. The compound according to claim 1 selected from:
- 2-cyano-3,11-dioxo-18β-oleana-1,12-dien-30-oic acid methyl ester;
- 2-cyano-3,11-dioxo-18α-oleana-1,12-dien-30-oic acid methyl ester;
- 2-iodo-3,11-dioxo-18β-oleana-1,12-dien-30-oic acid methyl ester;
- 2-iodo-3,11-dioxo-18α-oleana-1,12-dien-30-oic acid methyl ester;
- 2-trifluoromethyl-3,11-dioxo-18β-oleana-1,12-dien-30-oic acid methyl ester; and
- 2-trifluoromethyl-3,11-dioxo-18α-oleana-1,12-dien-30-oic acid methyl ester, and pharmaceutically acceptable salts and solvates thereof, and mixtures thereof in any ratio.

13. 2-Cyano-3,11-dioxo-18β-oleana-1,12-dien-30-oic acid methyl ester, and pharmaceutically acceptable salts and solvates thereof, and mixtures thereof in any ratio.

14. A pharmaceutical composition comprising a compound of Formula (I):

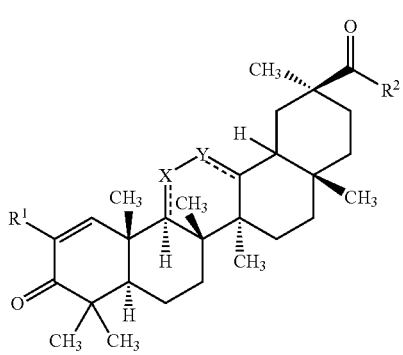

wherein $R^1$ is selected from CN, halo, $NO_2$, $CO_2R^3$, $C_{1-6}$alkyl, fluoro-substituted $C_{1-6}$alkyl, $C_{2-6}$alkenyl, $C_{2-6}$alkynyl, $OR^3$, $SR^3$, $SOR^3$, $SO_2R^3$, $NR^3R^4$, $C(O)NR^3R^4$, $C(O)R^3$, $OC(O)R^3$, $NHC(O)R^3$, $P(O)R^3R^4$, —C≡C—$R^3$, —$CR^3$=$CR^4R^5$, aryl and heteroaryl;

$R^2$ is selected from $OC_{1-6}$alkyl, fluoro-substituted $OC_{1-6}$alkyl, $NH_2$, $NHC_{1-6}$alkyl, $N(C_{1-6}$alkyl$)(C_{1-6}$alkyl$)$, SH and $SC_{1-6}$alkyl;

$R^3$, $R^4$ and $R^5$ are independently selected from H, $C_{1-6}$alkyl, fluoro-substituted $C_{1-6}$alkyl, aryl and heteroaryl; and one of X and Y is C=O while the other is $CH_2$, and if X is C=O then - - - adjacent to X represents a single bond and - - - adjacent to Y represents a double bond and if Y is C=O then - - - adjacent to Y represents a single bond and - - - adjacent to X represents a double bond;

or pharmaceutically acceptable salts and solvates thereof; and a pharmaceutically acceptable carrier, with the proviso that $R^1$ is not —OH or —$OCH_3$.

* * * * *